(12) United States Patent
Kishore et al.

(10) Patent No.: US 9,913,831 B2
(45) Date of Patent: *Mar. 13, 2018

(54) METHODS AND COMPOSITIONS FOR TREATING NEPHROGENIC DIABETES INSIPIDUS

(71) Applicant: UNIVERSITY OF UTAH RESEARCH FOUNDATION, Salt Lake City, UT (US)

(72) Inventors: Bellamkonda K. Kishore, Sandy, UT (US); Noel G. Carlson, Salt Lake City, UT (US); Yue Zhang, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/184,526

(22) Filed: Jun. 16, 2016

(65) Prior Publication Data

US 2016/0296504 A1 Oct. 13, 2016

Related U.S. Application Data

(63) Continuation of application No. 14/241,720, filed as application No. PCT/US2012/052819 on Aug. 29, 2012, now Pat. No. 9,539,246.

(60) Provisional application No. 61/529,227, filed on Aug. 30, 2011.

(51) Int. Cl.
| A61K 31/44 | (2006.01) |
| A61K 33/00 | (2006.01) |
| A61K 31/4365 | (2006.01) |
| A61K 31/519 | (2006.01) |
| A61K 45/06 | (2006.01) |
| A61K 31/64 | (2006.01) |
| A61K 31/7076 | (2006.01) |

(52) U.S. Cl.
CPC ........ A61K 31/4365 (2013.01); A61K 31/519 (2013.01); A61K 31/64 (2013.01); A61K 31/7076 (2013.01); A61K 33/00 (2013.01); A61K 45/06 (2013.01)

(58) Field of Classification Search
CPC .. A61K 31/4365; A61K 31/519; A61K 31/64; A61K 31/7076; A61K 33/00; A61K 45/06
USPC .......................................... 514/301; 424/722
See application file for complete search history.

(56) References Cited

U.S. PATENT DOCUMENTS

| 4,529,596 | A | 7/1985 | Aubert et al. |
| 5,288,726 | A | 2/1994 | Koike et al. |
| 7,101,860 | B2 | 9/2006 | Boyer et al. |
| 7,132,408 | B2 | 11/2006 | Boyer et al. |
| 7,368,438 | B2 | 5/2008 | Plourde, Jr. et al. |
| 7,452,870 | B2 | 11/2008 | Boyer et al. |
| 7,488,739 | B2 | 2/2009 | Watanuki et al. |
| 7,504,497 | B2 | 3/2009 | Douglass, III et al. |
| 7,618,949 | B2 | 11/2009 | Boyer et al. |
| 7,696,168 | B2 | 4/2010 | Kuliopulos et al. |
| 7,749,981 | B2 | 7/2010 | Boyer et al. |
| 7,879,878 | B2 | 2/2011 | Watanuki et al. |
| 7,910,576 | B2 | 3/2011 | Klingler et al. |
| 7,932,376 | B2 | 4/2011 | Douglass, III et al. |
| 7,943,760 | B2 | 5/2011 | Plourde, Jr. et al. |
| 9,539,246 | B2 * | 1/2017 | Kishore ............. A61K 31/4365 |
| 2005/0159388 | A1 | 7/2005 | Plourde et al. |
| 2005/0267134 | A1 | 12/2005 | Plourde et al. |
| 2006/0121086 | A1 | 6/2006 | Boyer et al. |
| 2006/0122143 | A1 | 6/2006 | Boyer et al. |
| 2006/0148806 | A1 | 7/2006 | Watanuki et al. |
| 2006/0258614 | A1 | 11/2006 | Douglass et al. |
| 2007/0093446 | A1 | 4/2007 | Douglass et al. |
| 2007/0244088 | A1 | 10/2007 | Brickmann et al. |
| 2008/0009523 | A1 | 1/2008 | Johansson |
| 2008/0027103 | A1 | 1/2008 | Sigfridsson |
| 2008/0027104 | A1 | 1/2008 | Andersen et al. |
| 2008/0032992 | A1 | 2/2008 | Brickmann et al. |
| 2008/0039437 | A1 | 2/2008 | Antonsson et al. |
| 2008/0045494 | A1 | 2/2008 | Giordanetto et al. |
| 2008/0103304 | A1 | 5/2008 | Plourde et al. |
| 2008/0171732 | A1 | 7/2008 | Antonsson et al. |
| 2008/0176827 | A1 | 7/2008 | Antonsson et al. |
| 2008/0194576 | A1 | 8/2008 | Caroff et al. |
| 2008/0200448 | A1 | 8/2008 | Antonsson et al. |
| 2008/0287671 | A1 | 11/2008 | Boyer et al. |
| 2008/0312208 | A1 | 12/2008 | Andersen et al. |
| 2009/0018166 | A1 | 1/2009 | Amin et al. |
| 2009/0042852 | A1 | 2/2009 | Bach et al. |
| 2009/0124617 | A1 | 5/2009 | Watanuki et al. |
| 2009/0186876 | A1 | 7/2009 | Brickmann et al. |

(Continued)

FOREIGN PATENT DOCUMENTS

| EP | 12828322.3 | 8/2012 |
| WO | WO-2005/076007 A2 | 8/2005 |

(Continued)

OTHER PUBLICATIONS

U.S. Appl. No. 14/241,720, filed Jul. 29, 2014, Kishore.
Extended European Search Report dated Feb. 5, 2015 for application EP 12828322.3, filed on Aug. 29, 2012, and published as EP 2750676 on Jan. 9, 2014 (Applicant—Kishore, et al. // Applicant—U. of Utah Research Foundation) (6 pages).
International Preliminary Report on Patentability dated Mar. 4, 2014 for International Application No. PCT/US2012/052819, which was filed on Aug. 29, 2012 and published as WO2013/033178 on Mar. 7, 2013. (Inventor—Kishore; Applicant—University of Utah Research Foundation) (pp. 1-7).
International Search Report dated Oct. 24, 2012 for International Application No. PCT/US2012/052819, which was filed on Aug. 29, 2012 and published as WO2013/033178 on Mar. 7, 2013. (Inventor—Kishore; Applicant—University of Utah Research Foundation) (pp. 1-3).

(Continued)

Primary Examiner — Raymond J Henley, III
(74) Attorney, Agent, or Firm — Ballard Spahr LLP

(57) ABSTRACT

Disclosed is a treatment of diabetes insipidus. Methods of treating diabetes insipidus disorders associated with P2Y receptors using the compounds and compositions are also disclosed.

21 Claims, 12 Drawing Sheets

(56) References Cited

U.S. PATENT DOCUMENTS

| | | |
|---|---|---|
| 2009/0197834 A1 | 8/2009 | Koga et al. |
| 2009/0227555 A2 | 9/2009 | Bach et al. |
| 2009/0286834 A1 | 11/2009 | Giordanetto et al. |
| 2009/0291962 A1 | 11/2009 | Caroff et al. |
| 2009/0297497 A1 | 12/2009 | Kishore et al. |
| 2009/0312368 A1 | 12/2009 | Johansson |
| 2009/0318464 A1 | 12/2009 | Brickmann et al. |
| 2010/0035895 A1 | 2/2010 | Caroff et al. |
| 2010/0069350 A1 | 3/2010 | Antonsson et al. |
| 2010/0113391 A1 | 5/2010 | Koga et al. |
| 2010/0135999 A1 | 6/2010 | Nazare et al. |
| 2010/0137277 A1 | 6/2010 | Antonsson et al. |
| 2010/0197913 A1 | 8/2010 | Plourde, Jr. et al. |
| 2010/0210654 A1 | 8/2010 | Muller et al. |
| 2010/0226918 A1 | 9/2010 | Klingler et al. |
| 2010/0261678 A1 | 10/2010 | Caroff et al. |
| 2010/0298350 A1 | 11/2010 | Michel |
| 2011/0021537 A1 | 1/2011 | Nazare et al. |
| 2011/0028484 A1 | 2/2011 | Caroff et al. |
| 2011/0039829 A1 | 2/2011 | Nazare et al. |
| 2011/0046089 A1 | 2/2011 | Caroff et al. |
| 2011/0059981 A9 | 3/2011 | Brickmann et al. |
| 2014/0377380 A1 | 12/2014 | Kishore et al. |

FOREIGN PATENT DOCUMENTS

| | | |
|---|---|---|
| WO | WO-2010/075861 A2 | 7/2010 |
| WO | PCT/US2012/052819 | 8/2012 |

OTHER PUBLICATIONS

Written Opinion dated Oct. 24, 2012 for International Application No. PCT/US2012/052819, which was filed on Aug. 29, 2012 and published as WO2013/033178 on Mar. 7, 2013. (Inventor—Kishore; Applicant—University of Utah Research Foundation) (pp. 1-5).

"Could Clopidogrel bisulfate cause urine output increase[]?" eHealthMe.com, 2012 (pp. 1-5).

"Could Plavix cause urine output decrease[]?", eHealthMe.com, 2012 (pp. 1-8).

"Urine output decreased in the use of Clopidogrel Bisulfate, who, when, how?", eHealthMe, 2011 (pp. 1-7).

Abbraccchio, M. P., et al., "International union of pharmacology LVIII: update on the P2Y G protein-coupled nucleotide receptors: from molecular mechanisms and pathophysiology to therapy," Pharmacol. Rev., 58(3), 281-341, 2006.

Agre, Peter, Aquaporin Water Channels in Kidney, J. Am. Soc. Nehrol. AA; 764-777, 2000.

Almarsson, O. & Zaworotko, M. J., "Crystal Engineering of the Composition of Pharmaceutical Phases. Do Pharmaceutical Co-crystals represent a new path to improved medicines?", Chem Commun (Camb), 17, 1889-96, 2004.

Baldessarini, R. J., et al., "Is lithium still worth using? An update of selected recent research," Harv. Rev. Psych., 10, 59-75, 2002.

Begley, C. D., et al., "The lifetime cost of bipolar disorder in the US: an estimate for new cases in 1998," Pharmacoeconomics, 19, 483-495, 2001.

Birch, N. J., et al., "The distribution of lithium and its effects on the distribution and excretion of other ions in the rat," Br. J. Pharmacol., 47, 586-594, 1973.

Boone, M. & Deen, P.M., "Physiology and pathphysiology of the vasopressin-regulated renal water reabsorption," Pflugers Arch., 456, 1005-24, 2008.

Boton, R., et al., "Prevalence, pathogenesis, and treatment of renal dysfunction associated with chrnoic lithium therapy," Am. J. Kid. Dis. 10, 329-345, 1987.

Bowden, C., "Efficacy of lithium in mania and maintenance therapy of biploar disorder," J. Clin. Psych. 61 (Suppl 9), 35-40, 2000.

Breyer, Matthew D., et al., Prostaglandin E receptors and the kidney, Am J Phsiol Renal Physiol, 279: F12-F23, 2000.

Chen, G., et al., "Enhancement of hippocampal neurogenesis by lithium," J. Neurochem., 75, 1729-1734, 2000.

Christensen, S., et al., "Pathogenesis of nephrogenic diabetes insipidus due to chronic administration of lithium in rats," J. Clin. Invest., 75, 1869-1879, 1985.

Devasamtia, et al., "Drug-associated renal dysfunction and injury", Nature Clinical Practice Nephrology, Nature Publishing Group, London, GB, vol. 2, No. 2, Feb. 1, 2006 (pp. 80-91).

DiGiovanni, Susan, et al., Regulation of collecting duct water channel expression by vasopressin in Brattleboro rat, Proc. Natl. Acad. Sco., USA, vol. 91, pp. 8984-8988, Sep. 1994.

Donowitz, M., et al., "Drug therapy for diarrheal diseases: a look ahead," Rev. Infect. Dis., 8, S188-S201, 1986.

Drevets, W. C., et al. "Subgenual prefrontal cortex abnormalities in mood disorders," Nature 38, 824-827, 1997.

Dwight, T., et al., "Genetic analysis of lithium-associated parathyroid tumors," Eur. J. Endocrinol., 146, 619-627, 2002.

Erb, et al., J Biol Chem. Mar. 3, 1995; 270(9): 4185-8.

Fradet, et al., Prostaglandins Med. Jul. 1980;5(1):29-30.

Frøkiaer, Jorgen, et al., Urinary Excretion of Aquaporin-2 in Rat is Mediated by a Vasopressin-Dependnt Apical Pathway, J Am Soc Nephrol 10: pp. 1416-1429, 1999.

Gelenberg, A. J., et al., "Comparison of standard and low serum levels of lithium for maintenance treatment of bipolar disorder," N. Eng. J. Med., 321, 1489-1493, 1989.

Goldberg, H., et al. "Mechanism of Li inhibition of vasopressin-sensitive adenylate cyclase in cultured renal epithelial cells," Am. J. Physiol., 255, F995-F1002, 1988.

Graciano, Miguel L., et al., Purinergic receptors contribute to early mesangial cell transformation and renal vessel hypertrophy during angiotensin II-induced hypertension, Am J Physiol Renal Physiol 294: F161-F169, 2008.

Graham, D. Y., et al., "Islet cell carcinoma, pancreatic cholera, and vasoactive intestinal peptide," Ann. Int. Med., 83, 782-785, 1975.

Graham, D. Y.,, "Lithium carbonate in pancreatic cholera," N. Eng. J. Med., 303, 1063-1064, 1980.

Han, J., et al., A MAP Kinase Targeted by Endotoxin and Hyperosmolarity in Mammalian Cells, Science, New Series, vol. 265, No. 5173 (Aug. 5, 1994), pp. 808-811.

Henry, C., "Lithium side-effects and predictors of hypothyroidism in patients with bipolar disorder: sex differences," J. Psych. Neurosci., 27, 104-107, 2002.

Hoffmann, K., et al., "Interaction of new, very potent non-nucleotide antagonists with Arg256 of the human platelet P2Y12 receptor," J. Pharmacology & Experimental Therapeutics, 331, 648-655, 2009.

Hoge, C. W., et al., "Combat duty in Iraq and Afghanistan, mental health problems, and barriers to care," New Eng J. Med, 351, 13-22, 2004.

Homma, et al., Prostaglandins Leukot Essent Fatty Acids. Mar. 1988;31(3):123-9.

Hozawa, Shingenari, et al., cAMP motifs regulating transcription in the aquaporin 2 gene, American Physiological Society, 1996, pp. c1695-c1702.

Inscho, Edward W., P2 receptors in regulation of renal microvascular function, Am J Physiol Renal Physiol 280: pp. F927-F944, 2001.

Jackson, B. A. et al., "Lithium-induced polyuria: effect of lithium on adenylate cyclase and adenosine 3', 5'-monophosphate phosphodiesterase in medullary ascending limb of Henle's loop and in medullary collecting tubues," Endocrinol. 107, 1693-1698, 1980.

Jefferson, J. W., "Lithium: the present and the future," Journal of Clinical Psychiatry, 51 (suppl):4-8, 1990.

Kishore, Bellamkonda, K., et al., Extracellular nucleotide receptor inhibits AVP-stimulated water permeability in inner medullary collecting duct, National Institutes of Health, F863-F869, 1995.

Kishore, Bellamkonda, K., et al., Rat Vasopressin V2 Receptor, J. Clin. Invest., vol. 97, No. 12, Jun. 1996, pp. 2763-2771 1996.

Kishore, Uday, et al., C1q: structure, function, and receptors, Immunopharmacology 49 (2000) pp. 159- 170.

Kohan & Hughes, Autocrine role of endothelin in rat IMCD: inhibition of AVP-induced CAMP accumulation, pp. F126-F129, 1993.

(56) References Cited

OTHER PUBLICATIONS

Krane & Kishore, Aquaporins: the membrane water channels of the biological world, Biologist 50 (2), pp. 81-86, 2003.
Laszlo, et al., Acta Physiol Acad Sci Hung. 1980;56(3):309-23.
Lenox, R. H., et al., "Neurobiology of lithium: an update," J Clin Psychiatry, 58, 37-47, 1998.
Matsumura, et al., Rapid Nitrification With Immobilized Cell Using Macro-Porous Cellulose Carrier, Wat. Res. vol. 31, No. 5, pp. 1027-1034, 1997.
Michelson, Alan D, "New P2Y12 antagonists", Current Opinion in Hematology, vol. 16, No. 5, Sep. 1, 2009 (pp. 371-377).
Mitchelle, P. B. & Malhi, G. S., "Emerging drugs for bipolar disorder," Expert Opin Emerg Drugs 11:621-634, 2006.
Nadler, et al., J Clin Invest. Oct. 1992 ;90(4): 1458-66.
Nemeroff, C. B., "An ever-increasing pharmacopoeia for the management of patients with bipolar disorder," J. Clin. Psych., 61 (suppl 13):19-25, 2000.
Nielsen, et al., Cellular and subcellular immunolocalization of vasopressinregulated water channel in rat kidney, Proc. Natl. Acad. Sci. USA, vol. 90, pp. 11663-11667, 1993.
Nielsen, et al., Interaction with members of the heterochromatin protein 1 (HP1) family and histone deacetylation are differentially involved in transcriptional silencing by members of the TIF1 family, Proc. Natl. Acad. Sci. USA, vol. 90, pp. 11663-11667, 1999.
Nielsen, et al., Vasopressin increases water permeability of kidney collecting duct by inducing translocation of aquaporin-CD water channels to plasma membrane, Proc. Natl. Acad. Sci. USA vol. 92, pp. 1013-1017, Feb. 1995.
Owyang, C., "Treatment of chronic secretory diarrhea of unknown origin by lithium carbonate," Gastroenterol. 87, 714-718, 1984.
Pandol, S. J., et al., "Beneficial effect of oral lithium carbonate in the treatment of pancreatic cholera syndrome," N. Eng. J. Med., 302, 1403-1404, 1980.
Pausch, M. H., et al., "Functional expression of human and mouse P2Y12 receptors in *Saccharomyces cerevisiae*," Biochem Biophys Res Commun., 324, 171-7, 2004.
Ralevic, V., "Receptors for purines and pyrimidines," Pharmacol Rev, 50(3), 413-92, 1998.
Reed & Yen, The Effect of Lithium on Electrolyte Transport by the in Situ Choroid Plexus of the Cat, J. Phwyeiol. (1980), 309, pp. 329-339, 1979.
Reist et al., Serotonin-stimulated calcium release is decreased in platelets from high impulsivity patients, International Journal of Neuropsychopharmacology (2000), 3, pp. 315-320.
Roman & Lechene, Prostaglandin E2 and F2a reduces urea reabsorption from the rat collecting duct, American Physiological Society, pp. F53-F60, 1981.
Rouch & Kudo, Role of PGE2 in a2-induced inhibition of AVP- and cAMP-stimulated H2O, Na1, and urea transport in rat IMCD, Am J Physiol Renal Physiol 279: F294-F301, 2000.
Rybakowski, J., "Antiviral and immunomodulatory effect on lithium," Pharmacopsychiatry, 33, 159-164, 2000.
Savi, P., et al., "The active metabolite of Clopidogrel disrupts P2Y12 receptor oligomers and partitions them out of lipid rafts," Proc Natl Acad Sci USA 103, 11069-11074, 2006.
Schou, M., "Lithium treatment at 52," J. Affect. Disord., 67, 21-32, 2001.
Schrier, R. W. "The sea within us: disorders of body water homeostasis," Curr Opin Investig Drugs, 8, 304-11, 2007.
Schrier, R. W. In: Renal and Electrolyte Disorders, Lippinocott Williams Wilkins, 2010, p. 12.
Schwiebert & Kishore, Extracellular nucleotide signaling along the renal epithelium, Am J Physiol Renal Physiol, 280: F945-F963, 2001.
Scott, J., et al., "Non-adherence with mood stabilizers: prevalence and predictors," J. Clin. Psych., 63, 384-390, 2002.
Sheline, Y. I., et al., "Depression duration but not age predicts hippocampal volume loss in medically healthy women with recurrent major depression," J. Neurosci., 19, 5034-5043, 1999.
Sheline, Y. I., et al., "Hippocampal atrophy in recurrent major depression," Proc. Natl. Acad. Sci., USA, 93, 3908-3913, 1996.
Skinner, G., "Lithium ointment for genital herpes," Lancet 2:288, 1983.
Skinner, G., et al., "The effect of lithium chloride on the replication of herpes simplex virus," Medical Microbiology and Immunology, 168, 139-148, 1980.
Soares, J. C., et al., "The anatomy of mood disorders—review of structural neuroimaging studies," Biol. Psych. 41, 86-106, 1997.
Sugawara, et al., Differential Roles of ERK and p38 MAP Kinase Pathways in Positive and Negative Selection of T Lymphocytes, Immunity, vol. 9, 565-574, Oct. 1998.
Sun, et al., A genetic screen in zebrafish identifies cilia genes as a principal cause of cystic kidney, Development and disease, pp. 4085-4093, 2004.
Takasaki, J. et al., "Molecular cloning of the platelet P2T(AC) ADP receptor: pharmacological comparison with another ADP receptor, the P2Y(1) receptor," Mol. Pharmacol., vol. 60, p. 432-9, 2001.
Teitelbaum, Toward a Synthetic Physiological Psychology, American Psychological Society vol. 3, No. I, Jan. 1992.
Tian, et al., "Down-regulation of renal vasopressin V2 receptor and aquaporin-2 expression parallels age-associated defects in urine concentration," Am J. Physiol Renal Physiol., 2004, vol. 287, pp. F797-F805.
Timmer, R. T. & Sands, J. M., "Lithium intoxication," J. Am. Soc. Nephrol., 10(3), 666-74, 1999.
Tozaki-Saitoh, et al., "P2Y12 receptors in spinal microglia are required for neuropathic pain after peripheral nerve injury," J. Neurosci 28:4949-4956, 2008.
Van Rhee et al., Modelling the P2Y Purinoceptor Using Rhodopsin as Template, Drug Des Discov. Nov. 1995 ; 13(2): 133-154.
Waring, W. S., "Management of lithium toxicity," Toxicol. Rev. 25, 221-230, 2006.
Welch, et al., Kinetic and equilibrium Fe isotope fractionation between aqueous Fe(II) and Fe(III), Geochimica et Cosmochimica Acta, vol. 67, No. 22, pp. 4231-4250, 2003.
Woods, S. W. "The economic burden of bipolar disease," J. Clin. Psych. 61 (suppl. 13), 38-41, 2000.
Wyatt, R. J. & Henter I., "An economic evaluation of manic-depressive illness—1991," Soc. Psych. Psych. Epid., 30, 213-219, 1995.
Yamaki, M., et al., "Cellular mechanism of lithium-induced nephrogenic diabetes insipidus in rats," Am. J. Physiol. 261, F505-F511, 1991.
Yasui, et al., Perinatal changes in expression of aquaporin-4 and other water and ion transporters in rat lung, Journal of Physiology (1997), 505.1, pp. 3-11.
Zelenina, et al., Osmotic water permeability measurements using confocal laser scanning microscopy, Eur Biophys J (2000) 29: 165-171.
Zhang, Y., et al., "Genetic deletion of the P2Y2 receptor offers significant resistance to development of lithium-induced polyuria accompanied by alterations in PGE2 signaling," Am J Physiol Renal Physiol 302:F70-F77, 2012.
Zhang, Y., et al., "Potential involvement of P2Y2 receptor in diuresis of post-obstructive neuropathy in rats," Am J Physiol Renal Physiol 298: F634-F642, 2010.
Zhang, Y., et al., "Potential role of purinergic signaling in lithium-induced nephrogenic diabetes insipidus," Am. J. Physiol. Renal Physiol. 260, F1194-F1201, 2009.
Zhang, Y., et al., "Potential role of purinergic signaling in urinary concentration in inner medulla: insights from P2Y2 receptor gene knockout mice," Am. J. Physiol. Renal Physiol. 295, F1715-F1724, 2008.
Zhang, Y., et al., "Renal sodium transporter/channel expression and sodium excretion in P2Y2 receptor knockout mice fed a high-NaCl diet with/without aldosterone infusion," Am. J. Physiol Renal Physiol 300:F657-F668, 2011.
Notice of Allowance issued by the USPTO dated Mar. 21, 2016 for U.S. Appl. No. 14/241,720, and published as US-2014-0377380-A1 on Dec. 25, 2014 (Applicant—Kishore, et al. // Applicant—U. of Utah Research Foundation) (7 pages).

(56) References Cited

OTHER PUBLICATIONS

Communication pursuant to Article 94(3) EPC dated Oct. 12, 2016 for application EP 12828322.3, filed on Aug. 29, 2012, and published as EP 2750676 on Jan. 9, 2014 (Applicant—Kishore, et al. // Applicant—U. of Utah Research Foundation) (3 pages).

* cited by examiner

```
                        SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
taaccattga ccgatacctg aag                                           23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 2
atcttcgcac ccaaaagatt gc                                            22

<210> SEQ ID NO 3
<211> LENGTH: 20
<212> TYPE: DNA
```

```
<213> ORGANISM: Artificial Sequence
<220> FEATURE:
<223> OTHER INFORMATION: Description of Artificial Sequence; note =
      synthetic construct

<400> SEQUENCE: 3
cacccgcgag tacaaccttc                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 4
cccataccca ccatcacacc                                              20
```

METHODS AND COMPOSITIONS FOR TREATING NEPHROGENIC DIABETES INSIPIDUS

CROSS REFERENCE TO RELATED APPLICATIONS

This application is a continuation of U.S. patent application Ser. No. 14/241,720, now U.S. Pat. No. 9,539,246, filed Jul. 29, 2014, which is a National Phase Application of International Application No. PCT/US2012/052819 filed Aug. 29, 2012, which claims the benefit of priority to U.S. Provisional Application 61/529,227, filed on Aug. 30, 2011, each of which is incorporated herein in its entirety by this reference.

STATEMENT REGARDING FEDERALLY SPONSORED RESEARCH

This invention was made possible with the facilities and resources at the VA Salt Lake City Health Care System, and funds from a VA Merit Review Project. Therefore, the United States Government may have certain rights in this invention.

REFERENCE TO SEQUENCE LISTING

The Sequence Listing submitted Jun. 16, 2016 as a text file named "21101_0244U3_Sequence_Listing.txt", which was created on Jun. 16, 2016 and has a size of 1,356 bytes, is hereby incorporated by reference pursuant to 37 C.F.R. § 1.52(e)(5).

BACKGROUND

Acquired nephrogenic diabetes insipidus (acquired NDI) is a common debilitating and morbid condition in the clinic due to a variety of causes. The salient feature of all forms of acquired NDI is resistance of the kidney to the action of the anti-diuretic hormone (ADH or arginine vasopressin, AVP), and so it is often associated with increased blood ADH levels. Acquired NDI is characterized by polydipsia (increased water intake), polyuria (increased urine output) and impaired concentrating ability of the kidney (decreased urine osmolality), associated with marked decrease in ADH-regulated AQP2 water channel in the kidney medulla. This is due to the resistance of the kidney to the action of the anti-diuretic hormone (ADH or AVP). Vasopressin (AVP or ADH), acting through its V2 receptor in the collecting duct principal cells of the kidney, and the associated cAMP signaling pathway and aquaporin (AQP) water channels, plays a central role in water homeostasis (for reviews see Schrier, R. W. (2007) Curr Opin Investig Drugs. 8:304-11; Boone M. and Deen, P. M. (2008) Pflugers Arch. 456:1005-24). However, a variety of autocrine and paracrine agents, acting through their respective membrane receptors in the collecting duct have been shown to modulate the action of AVP.

Acquired NDI is a common condition in the clinic with significant degree of morbidity, or even mortality if not treated properly. Apart from social inconvenience, NDI is a debilitating condition, with an elevated risk of dehydration, hypernatremia, altered consciousness, and hemodynamic instability from hypovolemia, especially in elderly patients. The most common causes of acquired NDI are lithium-induced or hypokalemic or hypercalcemic nephropathy or post-obstructive uropathy.

Currently used therapies for acquired NDI, such as administration of cyclooxygenase (COX) inhibitors or thiazides or amiloride, are associated with varying degrees of success as well as adverse effects, especially in critically ill and elderly patients. Hence, there is a need to introduce newer therapies with fewer side effects and better tolerability in all patients.

Despite advances in the treatment of renal disease and disorders, there is still a scarcity of compounds that are effective in the treatment of acquired NDI. These needs and other needs are satisfied by the present invention.

SUMMARY

In accordance with the purpose(s) of the invention, as embodied and broadly described herein, the invention, in one aspect, relates to methods for the treatment of acquired nephrogenic diabetes insipidus comprising the step of administering to a mammal an effective amount of a ADP-($P2Y_{12}$)-like receptor modulator, thereby treating nephrogenic diabetes insipidus. The invention, in a further aspect, relates to the treatment of nephrogenic diabetes insipidus (NDI).

Also disclosed are methods of co-treatment of nephrogenic diabetes insipidus and a neurological or psychiatric disorder comprising the step of co-administering to the mammal an effective amount of a ADP-(P2Y12)-like receptor modulator and an effective amount of a lithium salt, thereby treating, respectively, the nephrogenic diabetes insipidus and the neurological or psychiatric disorder.

Also disclosed are methods of treating nephrogenic diabetes insipidus comprising the step of administering an effective amount of a ADP-(P2Y12)-like receptor modulator to a mammal that is administered a lithium salt, thereby treating the nephrogenic diabetes insipidus.

Also disclosed are methods for the treatment of nephrogenic diabetes insipidus in a mammal comprising the step of administering to the mammal an effective amount of a compound selected from clopidogrel, ticlopidine, prasugrel, ticagrelor, cangrelor, and elinogrel.

Also disclosed are methods for co-treatment of nephrogenic diabetes insipidus and a neurological or psychiatric disorder comprising the step of co-administering to the mammal an effective amount of a lithium salt and an effective amount of a compound selected from clopidogrel, ticlopidine, prasugrel, ticagrelor, cangrelor, and elinogrel, thereby treating, respectively, the neurological or psychiatric disorder and the nephrogenic diabetes insipidus.

Also disclosed are methods for treating nephrogenic diabetes insipidus comprising the step of administering an effective amount of a compound selected from clopidogrel, ticlopidine, prasugrel, ticagrelor, cangrelor, and elinogrel to a mammal that is administered a lithium salt, thereby treating the nephrogenic diabetes insipidus.

Also disclosed are pharmaceutical compositions comprising an effective amount of a lithium salt in combination with an effective amount of a second agent that is a ADP-(P2Y12)-like receptor modulator. In a further aspect, disclosed are pharmaceutical compositions comprising an effective amount of a lithium salt in combination with an effective amount of a second agent selected from clopidogrel, ticlopidine, prasugrel, ticagrelor, cangrelor, and elinogrel. In a still further aspect, disclosed are pharmaceutical compositions comprising a therapeutically effective amount of a disclosed compound and a pharmaceutically acceptable carrier, or a pharmaceutically acceptable salt, hydrate, solvate, or polymorph thereof.

Also disclosed are uses of a disclosed compound, or a pharmaceutically acceptable salt, hydrate, solvate, or polymorph thereof. In a further aspect, the invention relates to pharmaceutical compositions comprising a pharmaceutically acceptable carrier and an effective amount of a disclosed compound, or a pharmaceutically acceptable salt, hydrate, solvate, or polymorph thereof.

Also disclosed are uses of a disclosed compound in the manufacture of a medicament for the treatment of nephrogenic diabetes insipidus. In a further aspect, disclosed are uses of a P2Y modulator in the manufacture of a medicament for the therapeutic and/or prophylactic treatment of nephrogenic diabetes insipidus. In a still further aspect, disclosed are uses of a P2Y modulator in the manufacture of an anti-diuretic agent in a package together with instructions for its use in the treatment of nephrogenic diabetes insipidus.

Also disclosed are kits comprising a lithium salt one or more of: (a) at least one agent known to decrease ADP-($P2Y_{12}$)-like receptor activity; (b) at least one agent known to treat nephrogenic diabetes insipidus; (c) instructions for treating a neurological disorder; (d) instructions for a treating a psychiatric disorder; or (e) instructions for treating nephrogenic diabetes insipidus.

Also disclosed are kits comprising a lithium salt one or more of: (a) at least one agent selected from clopidogrel, ticlopidine, prasugrel, ticagrelor, cangrelor, and elinogrel; (b) at least one agent known to treat nephrogenic diabetes insipidus; (c) instructions for treating a neurological disorder; (d) instructions for a treating a psychiatric disorder; or (e) instructions for treating nephrogenic diabetes insipidus.

It is to be understood that both the foregoing general description and the following detailed description are exemplary and explanatory only and are not restrictive. While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
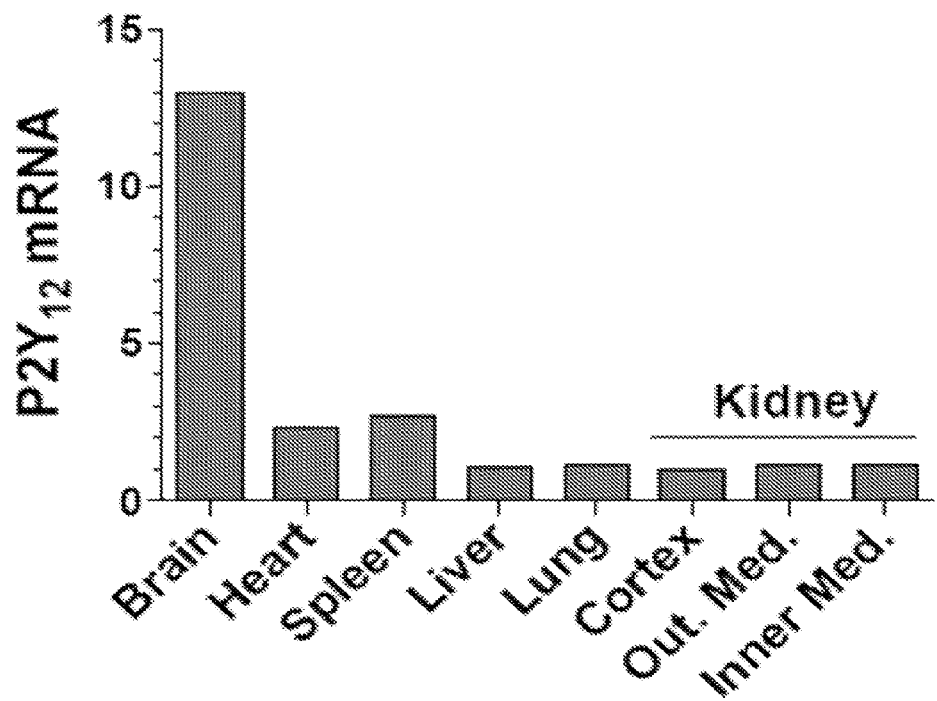
FIG. 1 shows representative data on the expression of $P2Y_{12}$-receptor mRNA in various tissues in rat.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the terms "higher," "increases," "elevates," or "elevation" refer to increases above basal levels, e.g., as compared to a control. The terms "low," "lower," "reduces," or "reduction" refer to decreases below basal levels, e.g., as compared to a control. For example, basal levels are normal in vivo levels prior to, or in the absence of, addition of an agent.

As used herein, the term "kidney cells" include all renal tubular epithelial cells, renal cortical tubules, glomerular cells, mesangial cells, interstitial cells, collecting duct principal cells, and intercalated cells of the kidney.

As used herein, the term "diabetes insipidus" includes, but is not limited to, any disease of the kidneys such as neurogenic, also known as central, hypothalamic, pituitary, or neurohypophyseal diabetes; nephrogenic, also known as vasopressin-resistant; gestanic; and dipsogenic diabetes.

As used herein, the term "test compound" is defined as any compound to be tested for its ability to interact with a selected cell, e.g., a $P2Y_{12}$ antagonist. Also, "test components" include drugs, molecules, and compounds that come from combinatorial libraries where thousands of such ligands are screened by drug class.

As used herein, the terms "control levels" or "control cells" are defined as the standard by which a change is measured, for example, the controls are not subjected to the experiment, but are instead subjected to a defined set of parameters, or the controls are based on pre- or post-treatment levels.

As used herein, the term "P2Y modulator" refers to any exogenously administered compound or agent that directly or indirectly modulates the activity of a member of the P2Y receptor family. In this context, a modulator is understood to indirectly or directly decrease the activity of the target P2Y receptor compared to the activity of the receptor in the absence of the exogenously administered compound or agent. Examples of directly acting compounds or agents are allosteric modulators, antagonists, and agonists. Examples of indirectly acting are compounds or agents that act to decrease the expression levels a P2Y gene either at the transcriptional or translational level.

As used herein, the term "ADP-($P2Y_{12}$)-like receptor modulator" refers to any exogenously administered compound or agent that directly or indirectly modulates the activity of one, multiple members, or all members of the ADP-($P2Y_{12}$)-like receptor group as defined hereinafter, which includes one or more of the following receptor proteins: $P2Y_{12}$, $P2Y_{13}$, $P2Y_{14}$, GPR34, GPR34-like, GPR82, GPR87, and GPR171. In this context, a modulator is understood to indirectly or directly decrease the activity of the target $P2Y_{12}$ receptor family member compared to the activity of the receptor in the absence of the exogenously administered compound or agent. Examples of directly acting compounds or agents are negative allosteric modulators, antagonists, and inhibitors. Examples of indirectly acting compounds are inhibitors of regulatory proteins, e.g. protein kinases, wherein the regulatory protein acts on the $P2Y_{12}$ receptor family member to modulate its activity. Further examples of indirectly activating compounds are compounds or agents that act to decrease the expression levels a $P2Y_{12}$ receptor family gene either at the transcriptional or translational level.

As used herein, the term "$P2Y_{12}$ modulator" refers to any exogenously administered compound or agent that directly or indirectly modulates the activity of a member of the $P2Y_{12}$ receptor. In this context, a modulator is understood to indirectly or directly decrease the activity of the target $P2Y_{12}$ receptor compared to the activity of the receptor in the absence of the exogenously administered compound or agent. Examples of directly acting compounds or agents are negative allosteric modulators, antagonists, and inhibitors. Examples of indirectly acting compounds are inhibitors of regulatory proteins, e.g. protein kinases, wherein the regulatory protein acts on the $P2Y_{12}$ receptor to modulate its activity. Further examples of indirectly activating compounds are compounds or agents that act to decrease the expression levels a $P2Y_{12}$ receptor gene either at the transcriptional or translational level.

As used herein, the term "$P2Y_{13}$ modulator" refers to any exogenously administered compound or agent that directly or indirectly modulates the activity of a member of the $P2Y_{13}$ receptor. In this context, a modulator is understood to indirectly or directly decrease the activity of the target $P2Y_{13}$ receptor compared to the activity of the receptor in the absence of the exogenously administered compound or agent. Examples of directly acting compounds or agents are negative allosteric modulators, antagonists, and inhibitors. Examples of indirectly acting compounds are inhibitors of regulatory proteins, e.g. protein kinases, wherein the regulatory protein acts on the $P2Y_{13}$ receptor to modulate its activity. Further examples of indirectly activating compounds are compounds or agents that act to decrease the expression levels a $P2Y_{13}$ receptor gene either at the transcriptional or translational level.

As used herein, the term "$P2Y_{14}$ modulator" refers to any exogenously administered compound or agent that directly or indirectly modulates the activity of a member of the $P2Y_{14}$ receptor. In this context, a modulator is understood to indirectly or directly decrease the activity of the target $P2Y_{14}$ receptor compared to the activity of the receptor in the absence of the exogenously administered compound or agent. Examples of directly acting compounds or agents are negative allosteric modulators, antagonists, and inhibitors. Examples of indirectly acting compounds are inhibitors of regulatory proteins, e.g. protein kinases, wherein the regulatory protein acts on the $P2Y_{14}$ receptor to modulate its activity. Further examples of indirectly activating compounds are compounds or agents that act to decrease the expression levels a $P2Y_{14}$ receptor gene either at the transcriptional or translational level.

As used herein, the term "GPR34 modulator" refers to any exogenously administered compound or agent that directly or indirectly modulates the activity of a member of the GPR34 gene product. In this context, a modulator is understood to indirectly or directly decrease the activity of the target GPR34 gene product compared to the activity of the receptor in the absence of the exogenously administered compound or agent. Examples of directly acting compounds or agents are negative allosteric modulators, antagonists, and inhibitors. Examples of indirectly acting compounds are inhibitors of regulatory proteins, e.g. protein kinases, wherein the regulatory protein acts on the GPR34 gene product to modulate its activity. Further examples of indirectly activating compounds are compounds or agents that act to decrease the expression levels a GPR34 gene either at the transcriptional or translational level.

As used herein, the term "GPR34-like modulator" refers to any exogenously administered compound or agent that directly or indirectly modulates the activity of a member of the GPR34-like gene product. In this context, a modulator is understood to indirectly or directly decrease the activity of the target GPR34-like gene product receptor compared to the activity of the receptor in the absence of the exogenously administered compound or agent. Examples of directly acting compounds or agents are negative allosteric modulators, antagonists, and inhibitors. Examples of indirectly acting compounds are inhibitors of regulatory proteins, e.g. protein kinases, wherein the regulatory protein acts on the GPR34-like gene product to modulate its activity. Further examples of indirectly activating compounds are compounds or agents that act to decrease the expression levels a GPR34-like gene either at the transcriptional or translational level.

As used herein, the term "GPR82 modulator" refers to any exogenously administered compound or agent that directly or indirectly modulates the activity of a member of the GPR82 gene product. In this context, a modulator is understood to indirectly or directly decrease the activity of the target GPR82 gene product compared to the activity of the receptor in the absence of the exogenously administered compound or agent. Examples of directly acting compounds or agents are negative allosteric modulators, antagonists, and inhibitors. Examples of indirectly acting compounds are inhibitors of regulatory proteins, e.g. protein kinases, wherein the regulatory protein acts on the GPR82 gene product to modulate its activity. Further examples of indirectly activating compounds are compounds or agents that act to decrease the expression levels a GPR82 gene either at the transcriptional or translational level.

As used herein, the term "GPR87 modulator" refers to any exogenously administered compound or agent that directly or indirectly modulates the activity of a member of the GPR87 gene product. In this context, a modulator is understood to indirectly or directly decrease the activity of the target GPR87 gene product compared to the activity of the receptor in the absence of the exogenously administered compound or agent. Examples of directly acting compounds or agents are negative allosteric modulators, antagonists, and inhibitors. Examples of indirectly acting compounds are inhibitors of regulatory proteins, e.g. protein kinases, wherein the regulatory protein acts on the GPR87 gene product to modulate its activity. Further examples of indirectly activating compounds are compounds or agents that act to decrease the expression levels a GPR87 gene either at the transcriptional or translational level.

As used herein, the term "GPR171 modulator" refers to any exogenously administered compound or agent that directly or indirectly modulates the activity of a member of the GPR171 gene product. In this context, a modulator is understood to indirectly or directly decrease the activity of the target GPR171 gene product compared to the activity of the receptor in the absence of the exogenously administered compound or agent. Examples of directly acting compounds or agents are negative allosteric modulators, antagonists, and inhibitors. Examples of indirectly acting compounds are inhibitors of regulatory proteins, e.g. protein kinases, wherein the regulatory protein acts on the GPR171 gene product to modulate its activity. Further examples of indirectly activating compounds are compounds or agents that act to decrease the expression levels a GPR171 gene either at the transcriptional or translational level.

As used herein, the terms "ADP-($P2Y_{12}$)-like receptor", "$P2Y_{12}$-like receptor", and "$P2Y_{12}$-like group" can be used interchangeably, and refer to a group of proteins comprising at least the following members: $P2Y_{12}$, $P2Y_{13}$, $P2Y_{14}$, GPR34, GPR34-like, GPR82, GPR87, and GPR171. The terms can be used to refer to a single member, multiple members or all members.

As used herein, the terms "$P2Y_{12}$" refers to the GPCR receptor protein encoded by a gene designated in human as the P2RY12 gene, which has a human gene map locus described by Entrez Gene cytogenetic band: 3q24-q25; Ensembl cytogenetic band: 3q25.1; and, HGNC cytogenetic band: 3q24-q25. The term $P2Y_{12}$ refers to a human protein that has about 342 amino acids and has a molecular weight of about 39,439 Da. The term is inclusive of splice isoforms or mRNA transcript variants, and is also inclusive of that protein referred to by such alternative designations as: P2Y12, HORK3, SP1999, ADPG-R, P2T(AC), P2Y(AC), P2Y(ADP), P2Y(cyc), ADP-glucose receptor, P2Y12 platelet ADP receptor, G-protein coupled receptor SP1999, G-coupled ADP receptor HORK3, P2Y purinoceptor 12, purinergic receptor P2RY12, putative G-protein coupled receptor, and purinergic receptor P2Y, G-protein coupled, 12, as used by those skilled in the art to refer to that protein encoded by human gene P2RY12 or to the gene itself. The term is also inclusive of the non-human orthologs or homologs thereof, as well as splice variants and alternative transcripts of the P2RY12 gene.

As used herein, the terms "$P2Y_{13}$" refers to the GPCR receptor protein encoded by a gene designated in human as the P2RY13 gene, which has a human gene map locus described by Entrez Gene cytogenetic band: 3q24; Ensembl cytogenetic band: 3q25.1; and, HGNC cytogenetic band: 3q24. The term $P2Y_{13}$ refers to a human protein that has about 354 amino acids and has a molecular weight of about 40,789 Da. The term is inclusive of the protein product of splice isoforms or mRNA transcript variants, and is also inclusive of that protein referred to by such alternative designations as: P2RY13; purinergic receptor P2Y, G-protein coupled, 13; P2Y13; GPR86; G protein-coupled receptor 86; GPR94; G-protein coupled receptor 86; G-protein coupled receptor 94; FKSG77; GPCR1; SP174; P2Y purinoceptor 13; and purinergic receptor P2Y, G-protein coupled, 13; as used by those skilled in the art to refer to that protein encoded by human gene P2RY13 or to the gene itself. The term is also inclusive of the non-human ortholog or homolog thereof.

As used herein, the terms "$P2Y_{14}$" refers to the GPCR receptor protein encoded by a gene designated in human as the P2RY14 gene, which has a human gene map locus described by Entrez Gene cytogenetic band: 3q24-q25.1; Ensembl cytogenetic band: 3q25.1; and, HGNC cytogenetic band: 3q21-q25. The term $P2Y_{14}$ refers to a human protein that has about 338 amino acids and has a molecular weight of about 38,971 Da. The term is inclusive of the protein product of splice isoforms or mRNA variants, and also inclusive of that protein referred to by such alternative designations as: P2RY14; purinergic receptor P2Y, G-protein coupled, 14; UDP-glucose receptor; KIAA00011; OTTHUMP00000216780; G protein-coupled receptor 105; G protein coupled receptor for UDP-glucose; GPR105; P2Y purinoceptor 14; P2Y14; P2Y(14) receptor; G-protein coupled receptor 105; P2Y14 receptor; and purinergic receptor P2Y, G-protein coupled, 14; as used by those skilled in the art to that protein encoded by human gene P2RY14 or to the gene itself. The term is also inclusive of the non-human ortholog or homolog thereof.

As used herein, "gene product" refers to transcription or translation products that are derived from a specific gene locus or gene. The "gene locus" or "gene" includes coding sequences as well as regulatory, flanking and intron sequences.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for modulation of one or more ADP-($P2Y_{12}$)-like receptors prior to the administering step. In some aspects of the disclosed method, the subject has been diagnosed with a need for modulation of $P2Y_{12}$ prior to the administering step. In some aspects of the disclosed method, the subject has been diagnosed with a need for modulation of one or more of $P2Y_{12}$, $P2Y_{13}$, $P2Y_{14}$, GPR34, GPR34-like, GPR82, GPR87, and GPR171 proteins prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with nephrogenic diabetes insipidus" means having been subjected to a physical examination by a person of skill, for example, a physician, and found to have a condition that can be diagnosed or treated by a compound or composition that can treat nephrogenic diabetes insipidus. As a further example, "diagnosed with a need for treatment of nephrogenic diabetes insipidus" refers to having been subjected to a physical examination by a person of skill, for example, a physician, and found to have a condition characterized by the kidney's inability to respond to the antidiuretic hormone, arginine vasopressin (AVP) and causes a subject or patient to pass a large amount of urine. Such a diagnosis can be in reference to a disorder, such as acquired nephrogenic diabetes and the like, as discussed herein. For example, the term "diagnosed with a need for modulation of ADP-($P2Y_{12}$)-like receptor activity" refers to having been subjected to a physical examination by a person of skill, for example, a physician, and found to have a condition that can be diagnosed or treated by modulation of ADP-($P2Y_{12}$)-like receptor activity. For example, "diagnosed with a need for treatment of one or more nephrogenic diabetes insipidus disorders associated with ADP-($P2Y_{12}$)-like receptor dysfunction" means having been subjected to a physical examination by a person of skill, for example, a physician, and found to have one or more nephrogenic diabetes insipidus disorders associated with ADP-($P2Y_{12}$)-like receptor dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to ADP-($P2Y_{12}$)-like receptor activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target ADP-($P2Y_{12}$)-like receptor protein, or other biological entity together in such a manner that the compound can affect the activity of the target (e.g., ADP-($P2Y_{12}$)-like receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance. In a yet further aspect, the inhibition is measured in vitro. In a still further aspect, the inhibition is measured in a cell-line transfected with a human ADP-($P2Y_{12}$)-like receptor, e.g. an expression construct containing a cDNA coding for all or a portion of an ADP-($P2Y_{12}$)-like receptor. In an even further aspect, the inhibition is measured in a cell-line transfected with a human $P2Y_{12}$ receptor, e.g. an expression construct containing a cDNA coding for all or a portion of an ADP-$P2Y_{12}$ receptor. The ADP-($P2Y_{12}$)-like receptor, e.g. the human $P2Y_{12}$ receptor, may be obtained from any suitable source such as the rat, mouse, or human cDNA. In a still further aspect, the inhibition is measured in an HEK293, HeLa, or other suitable cell line.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in polyester refers to one or more —$OCH_2CH_2O$— units in the polyester, regardless of whether ethylene glycol was used to prepare the polyester. Similarly, a sebacic acid residue in polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

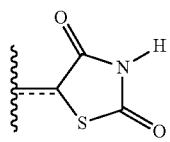

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

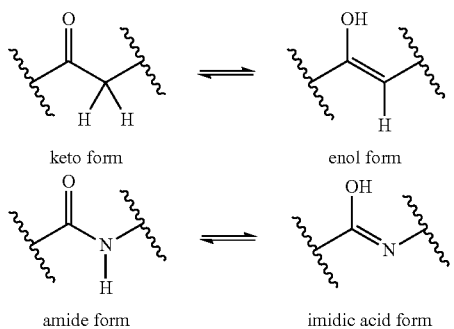

keto form / enol form
amide form / imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

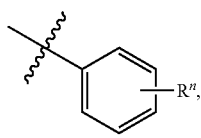

which is understood to be equivalent to a formula:

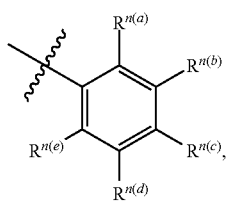

wherein n is typically an integer. That is, Rn is understood to represent five independent substituents, Rn(a), Rn(b), Rn(c), Rn(d), Rn(e). By "independent substituents," it is meant that each R substituent can be independently defined. For example, if in one instance Rn(a) is halogen, then Rn(b) is not necessarily halogen in that instance.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It is understood that the compositions disclosed herein have certain functions. Disclosed herein are certain structural requirements for performing the disclosed functions and it is understood that there are a variety of structures that can perform the same function that are related to the disclosed structures, and that these structures will typically achieve the same result.

B. ADP-(P2Y$_{12}$)-LIKE RECEPTOR MODULATORS

In one aspect, the invention relates to compounds useful as modulators of ADP-(P2Y$_{12}$)-like receptors. More specifically, in a further aspect, the present invention relates to compounds that modulate P2Y$_{12}$ receptor activity. In a still further aspect, the present invention relates to compounds that modulate the activity of one or more proteins selected from P2Y$_{12}$, P2Y$_{13}$, P2Y$_{14}$, GPR34, GPR34-like, GPR82, GPR87, and GPR171. The disclosed compounds can selectively modulate a single member of the ADP-(P2Y$_{12}$)-like receptor family, e.g. P2Y$_{12}$, compared to other P2Y receptors. In a yet further aspect, the disclosed compounds can modulate a subset of the ADP-(P2Y$_{12}$)-like receptor family, e.g. P2Y$_{12}$, P2Y$_{13}$, and P2Y$_{14}$. In an even further aspect, the disclosed compounds can modulate all members of the ADP-(P2Y$_{12}$)-like receptor family, i.e. P2Y$_{12}$, P2Y$_{13}$, P2Y$_{14}$, GPR34, GPR34-like, GPR82, GPR87, and GPR171. It is to be understood that a given compound can modulate different members of the ADP-(P2Y$_{12}$)-like receptor family with distinct levels of modulatory activity (e.g. the IC$_{50}$ for inhibition for each member of the ADP-(P2Y$_{12}$)-like receptor family can vary from one to another by several fold).

In one aspect, the compounds of the invention are useful in the treatment of diabetes insipidus disorders in which one or more ADP-(P2Y$_{12}$)-like receptors are involved, as further described herein. In a further aspect, diabetes insipidus is nephrogenic diabetes insipidus. In a yet further aspect, nephrogenic diabetes insipidus is acquired nephrogenic diabetes insipidus. It is to be understood that the acquired nephrogenic diabetes insipidus can be induced by prior treatment with a therapeutic agent. For example, the therapeutic agent lithium (which can be lithium carbonate or lithium citrate) can induce acquired nephrogenic diabetes insipidus.

Furthermore, in various aspects, the disclosed compounds can be co-administered with a therapeutic agent that can induce acquired nephrogenic diabetes insipidus. In such a clinical context, the disclosed compounds can be co-administered a therapeutic agent that can induce acquired nephrogenic diabetes insipidus in order to prevent or ameliorate the onset of acquired nephrogenic diabetes insipidus. For example, the disclosed compounds can be co-administered with lithium, e.g. lithium carbonate or lithium citrate, in order to prevent or ameliorate the onset of acquired nephrogenic diabetes insipidus associated with the administration of lithium.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In one aspect, the ADP-(P2Y$_{12}$)-like receptor modulators of the invention comprise substituted thieno[3,2-c]pyridine derivatives. In a further aspect, the ADP-(P2Y$_{12}$)-like receptor modulators of the invention comprise compounds having a structure represented by a formula:

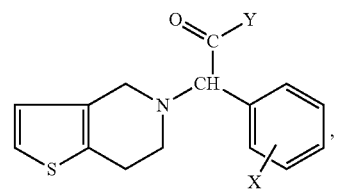

wherein the definitions of substituent groups can be as disclosed in U.S. Pat. No. 4,529,596.

In a further aspect, the ADP-(P2Y$_{12}$)-like receptor modulators of the invention comprise substituted tetrahydrothienopyridine derivatives. In a still further aspect, the ADP-(P2Y$_{12}$)-like receptor modulators of the invention comprise compounds having a structure represented by a formula:

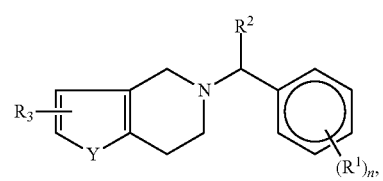

wherein the definitions of substituent groups can be as disclosed in U.S. Pat. No. 5,288,726.

In a further aspect, the ADP-(P2Y$_{12}$)-like receptor modulators of the invention comprise compounds having a structure represented by a formula:

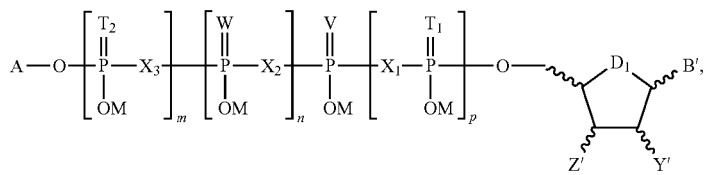

wherein the definitions of substituent groups can be as disclosed in U.S. Pat. No. 7,452,870.

In a further aspect, the ADP-(P2Y$_{12}$)-like receptor modulators of the invention comprise compounds having a structure represented by a formula:

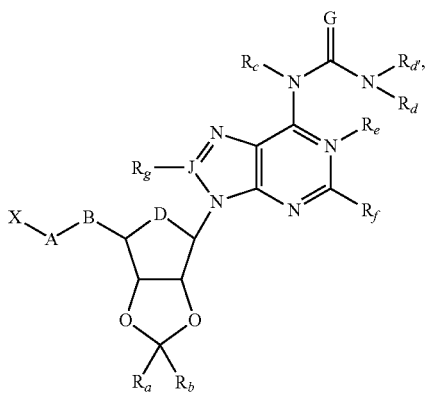

wherein the definitions of substituent groups can be as disclosed in U.S. Pat. No. 7,749,981.

In a further aspect, the ADP-(P2Y$_{12}$)-like receptor modulators of the invention comprise substituted pyrrole derivatives. In a still further aspect, the ADP-(P2Y$_{12}$)-like receptor modulators of the invention comprise compounds having a structure represented by a formula:

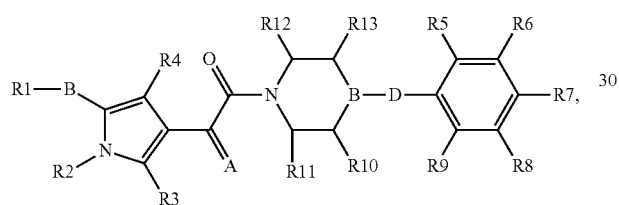

wherein the definitions of substituent groups can be as disclosed in U.S. Pat. No. 7,910,576.

In a further aspect, the ADP-(P2Y$_{12}$)-like receptor modulators of the invention comprise substituted bicyclic heterocylic derivatives. In a still further aspect, the ADP-(P2Y$_{12}$)-like receptor modulators of the invention comprise compounds having a structure represented by a formula:

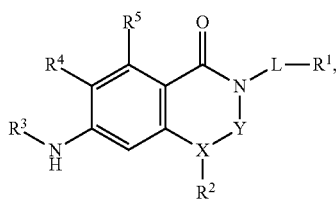

wherein the definitions of substituent groups can be as disclosed in US 20100113391.

In a further aspect, the ADP-(P2Y$_{12}$)-like receptor modulators of the invention comprise substituted quinoline carboxamide derivatives. In a still further aspect, the ADP-(P2Y$_{12}$)-like receptor modulators of the invention comprise compounds having a structure represented by a formula:

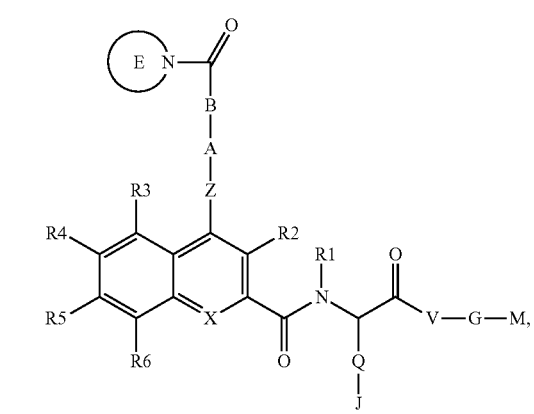

wherein the definitions of substituent groups can be as disclosed in US 20100135999.

In a further aspect, the ADP-(P2Y$_{12}$)-like receptor modulators of the invention comprise compounds having a structure represented by a formula:

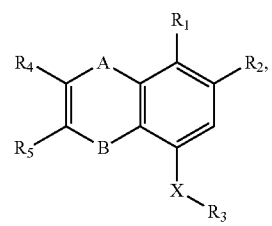

wherein the definitions of substituent groups can be as disclosed in US 20100210654.

In a further aspect, the ADP-(P2Y$_{12}$)-like receptor modulators of the invention comprise substituted pyrrole carboxamide derivatives. In a still further aspect, the ADP-(P2Y$_{12}$)-like receptor modulators of the invention comprise compounds having a structure represented by a formula:

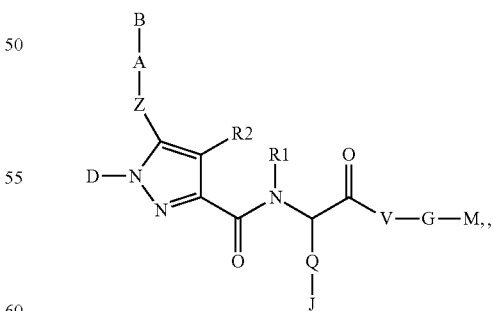

wherein the definitions of substituent groups can be as disclosed in US 201110039829.

In a further aspect, the ADP-(P2Y$_{12}$)-like receptor modulators of the invention comprise compounds having a structure represented by a formula:

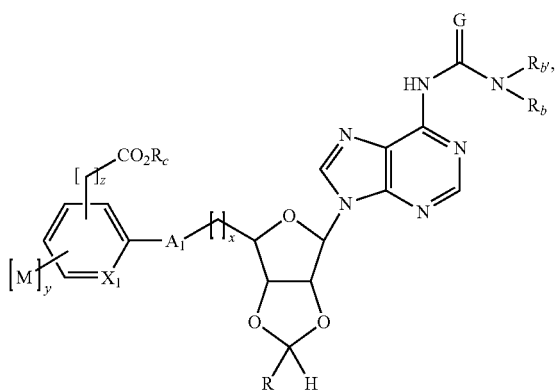

wherein the definitions of substituent groups can be as disclosed in U.S. Pat. No. 7,504,497.

In a further aspect, the ADP-(P2Y$_{12}$)-like receptor modulators of the invention comprise substituted pyrimidine-based non-nucleotide derivatives. In a still further aspect, the ADP-(P2Y$_{12}$)-like receptor modulators of the invention comprise compounds having a structure represented by a formula:

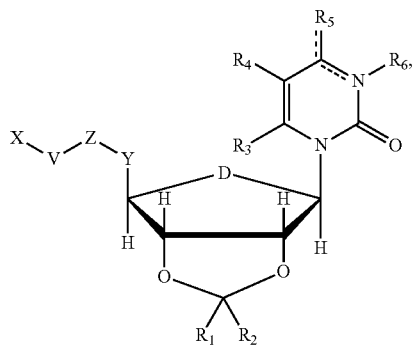

wherein the definitions of substituent groups can be as disclosed in U.S. Pat. No. 7,932,376.

In a further aspect, the ADP-(P2Y$_{12}$)-like receptor modulators of the invention comprise substituted pyridine derivatives. In a still further aspect, the ADP-(P2Y$_{12}$)-like receptor modulators of the invention comprise compounds having a structure represented by a formula:

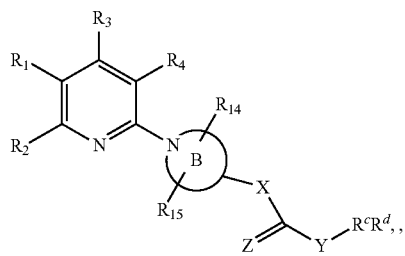

wherein the definitions of substituent groups can be as disclosed in US 20070244088.

In a further aspect, the ADP-(P2Y$_{12}$)-like receptor modulators of the invention comprise substituted pyridine derivatives. In a still further aspect, the ADP-(P2Y$_{12}$)-like receptor modulators of the invention comprise compounds having a structure represented by a formula:

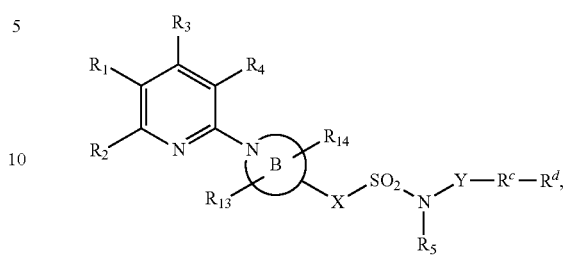

wherein the definitions of substituent groups can be as disclosed in US 20080009523.

In a further aspect, the ADP-(P2Y$_{12}$)-like receptor modulators of the invention comprise substituted pyridine derivatives. In a still further aspect, the ADP-(P2Y$_{12}$)-like receptor modulators of the invention comprise compounds having a structure represented by a formula:

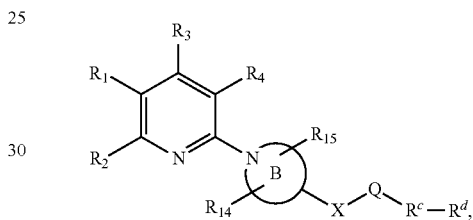

wherein the definitions of substituent groups can be as disclosed in US 20080032992.

In a further aspect, the ADP-(P2Y$_{12}$)-like receptor modulators of the invention comprise substituted pyridine derivatives. In a still further aspect, the ADP-(P2Y$_{12}$)-like receptor modulators of the invention comprise compounds having a structure represented by a formula:

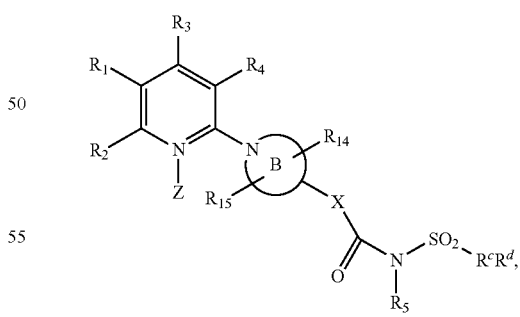

wherein the definitions of substituent groups can be as disclosed in US 20080039437.

In a further aspect, the ADP-(P2Y$_{12}$)-like receptor modulators of the invention comprise substituted pyridine derivatives. In a still further aspect, the ADP-(P2Y$_{12}$)-like receptor modulators of the invention comprise compounds having a structure represented by a formula:

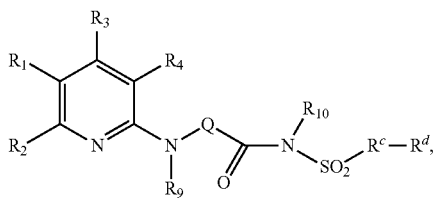

wherein the definitions of substituent groups can be as disclosed in US 20080171732.

In a further aspect, the ADP-(P2Y$_{12}$)-like receptor modulators of the invention comprise substituted pyridine derivatives. In a still further aspect, the ADP-(P2Y$_{12}$)-like receptor modulators of the invention comprise compounds having a structure represented by a formula:

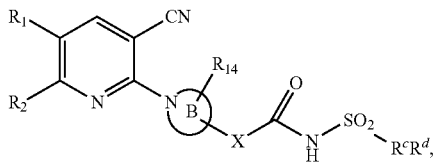

wherein the definitions of substituent groups can be as disclosed in US 20080176827.

In a further aspect, the ADP-(P2Y$_{12}$)-like receptor modulators of the invention comprise substituted pyrimidine derivatives. In a still further aspect, the ADP-(P2Y$_{12}$)-like receptor modulators of the invention comprise compounds having a structure represented by a formula:

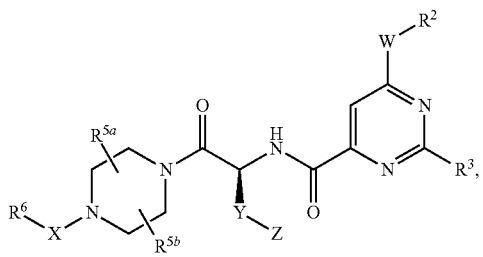

wherein the definitions of substituent groups can be as disclosed in US 20080194576.

In a further aspect, the ADP-(P2Y$_{12}$)-like receptor modulators of the invention comprise substituted quinolone derivatives. In a still further aspect, the ADP-(P2Y$_{12}$)-like receptor modulators of the invention comprise compounds having a structure represented by a formula:

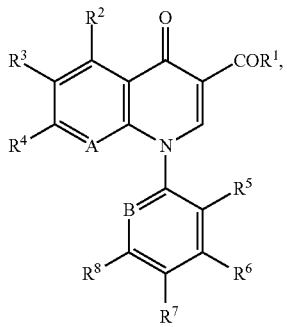

wherein the definitions of substituent groups can be as disclosed in US 20090197834.

In a further aspect, the ADP-(P2Y$_{12}$)-like receptor modulators of the invention comprise substituted 2-phenyl-6-aminocarbonyl pyrimidine derivatives. In a still further aspect, the ADP-(P2Y$_{12}$)-like receptor modulators of the invention comprise compounds having a structure represented by a formula:

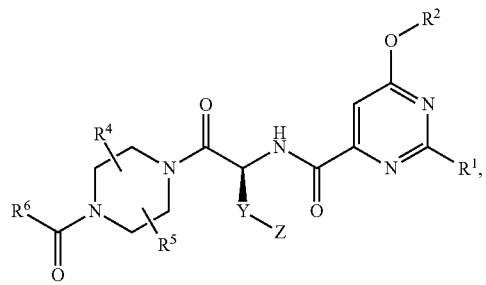

wherein the definitions of substituent groups can be as disclosed in US 20090291962.

In a further aspect, the ADP-(P2Y$_{12}$)-like receptor modulators of the invention comprise substituted quinolone carboxamide derivatives. In a still further aspect, the ADP-(P2Y$_{12}$)-like receptor modulators of the invention comprise compounds having a structure represented by a formula:

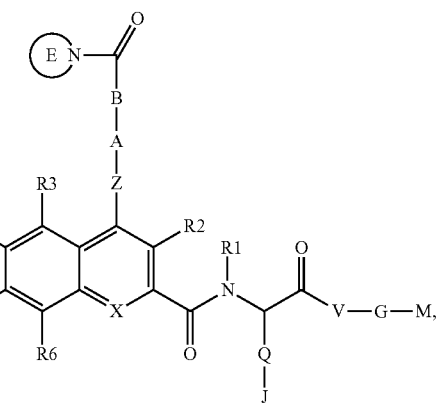

wherein the definitions of substituent groups can be as disclosed in US 20100135999.

In a further aspect, the ADP-(P2Y$_{12}$)-like receptor modulators of the invention comprise substituted phosphonic acid derivatives. In a still further aspect, the ADP-(P2Y$_{12}$)-like receptor modulators of the invention comprise compounds having a structure represented by a formula:

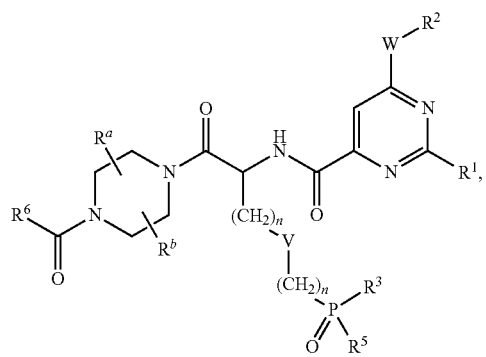

wherein the definitions of substituent groups can be as disclosed in US 20100261678.

In a further aspect, the ADP-(P2Y$_{12}$)-like receptor modulators of the invention comprise substituted triazolo[4,5-D]pyrimidine derivatives. In a still further aspect, the ADP-(P2Y$_{12}$)-like receptor modulators of the invention comprise compounds having a structure represented by a formula selected from:

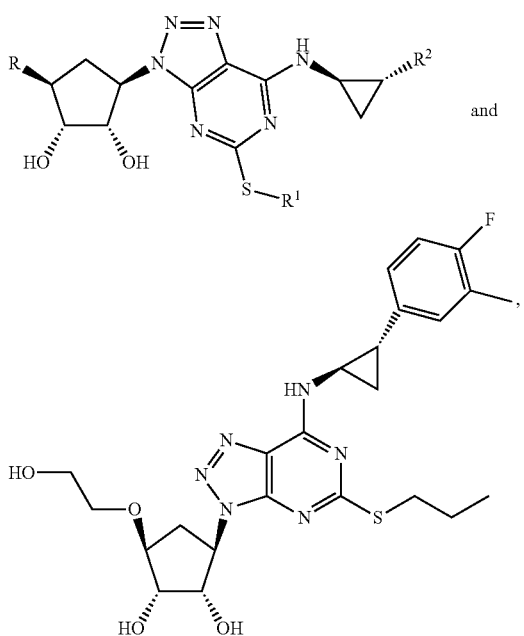

and

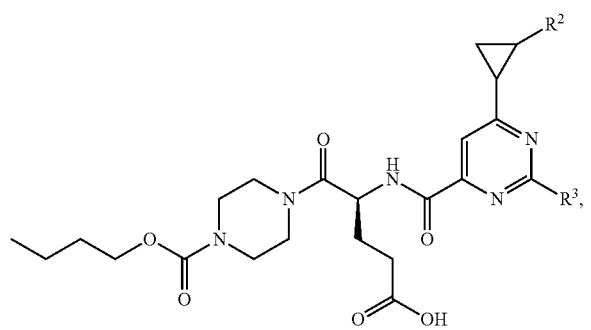

wherein the definitions of substituent groups can be as disclosed in US 20100298350.

In a further aspect, the ADP-(P2Y$_{12}$)-like receptor modulators of the invention comprise substituted 2-phenyl-4-cyclopropyl-pyrimidine derivatives. In a still further aspect, the ADP-(P2Y$_{12}$)-like receptor modulators of the invention comprise compounds having a structure represented by a formula:

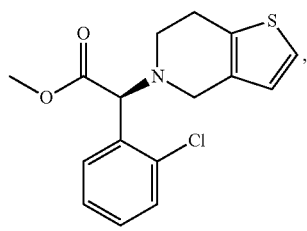

wherein the definitions of substituent groups can be as disclosed in US 20110028484.

In a further aspect, the ADP-(P2Y$_{12}$)-like receptor modulators of the invention comprise P2Y$_{12}$ antagonists and inhibitors such as pyridine analogues, pyrazole carboxamide derivatives, 2-phenyl-pyridine derivatives, heterocyclic pyrazole carboxamide derivatives, triazolo[4,5-D]pyrimidine derivatives, phosphonic acid derivatives, pyrrole derivatives, quinolone derivatives, 2-phenyl-6-aminocarbonyl-pyrimidine derivatives, 2-aminocarbonyl-pyridine derivatives, bicyclic heterocyclic derivatives, and quinolone carboxamide derivatives. Suitable ADP-(P2Y$_{12}$)-like receptor modulators for use in the disclosed methods of the invention are disclosed in U.S. Pat. No. 7,101,860, U.S. Pat. No. 7,132,408, U.S. Pat. No. 7,368,438, U.S. Pat. No. 7,452,870, U.S. Pat. No. 7,452,870, U.S. Pat. No. 7,488,739, U.S. Pat. No. 7,504,497, U.S. Pat. No. 7,618,949, U.S. Pat. No. 7,696,168, U.S. Pat. No. 7,749,981, U.S. Pat. No. 7,749,981, U.S. Pat. No. 7,879,878, U.S. Pat. No. 7,910,576, U.S. Pat. No. 7,932,376, U.S. Pat. No. 7,943,760, US20050159388, US20050267134, US20060121086, US20060122143, US20060148806, US20060258614, US20070093446, US20070244088, US20080009523, US20080027103, US20080027104, US20080032992, US20080039437, US20080045494, US20080103304, US20080171732, US20080176827, US20080194576, US20080200448, US20080287671, US20080312208, US20090018166, US20090042852, US20090124617, US20090186876, US20090197834, US20090197834, US20090227555, US20090286834, US20090291962, US20090312368, US20090318464, US20100035895, US20100069350, US20100113391, US20100135999, US20100137277, US20100197913, US20100210654, US20100210654, US20100226918, US20100261678, US20100298350, US20110021537, US20110028484, US20110039829, US20110046089, and US20110059981. The compounds disclosed in the foregoing are incorporated herein by reference in their entirety.

In one aspect, a ADP-(P2Y$_{12}$)-like receptor modulators can be present as one or more of the following compounds:

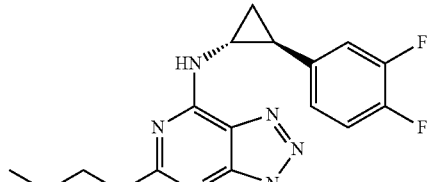

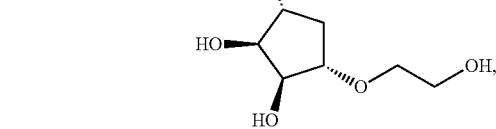

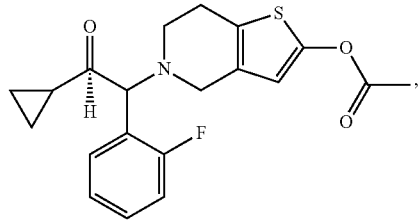

-continued

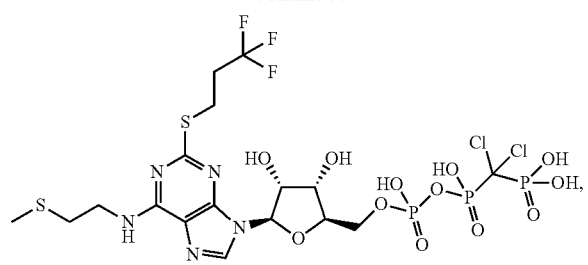

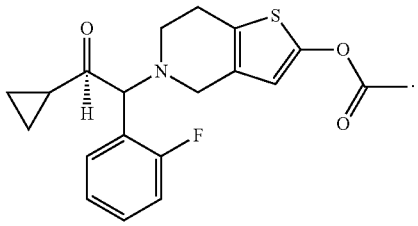

In one aspect, a ADP-(P2Y$_{12}$)-like receptor modulator can be present as:

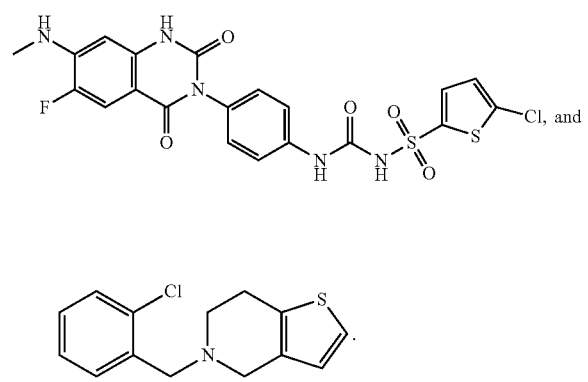

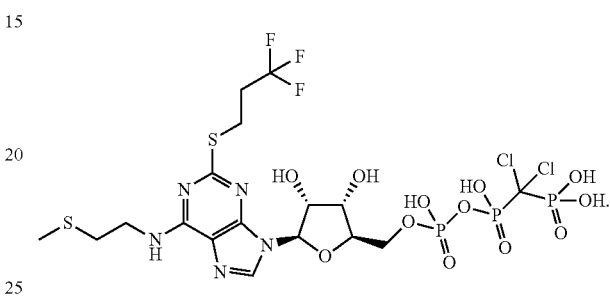

In one aspect, a ADP-(P2Y$_{12}$)-like receptor modulator can be present as:

In one aspect, a ADP-(P2Y$_{12}$)-like receptor modulator can be present as:

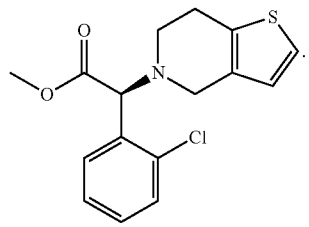 [SMILES: COC(=O)[C@H](c1ccccc1Cl)N1CCc2sccc2C1]

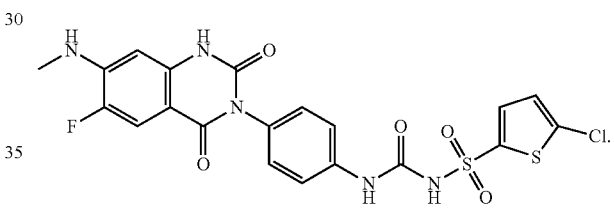

In one aspect, a ADP-(P2Y$_{12}$)-like receptor modulator can be present as:

In one aspect, a ADP-(P2Y$_{12}$)-like receptor modulator can be present as:

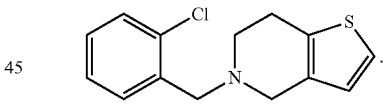

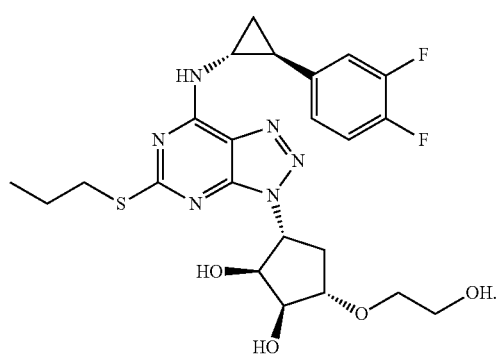 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

In one aspect, a compound can be present as one or more of the compounds referred to by their USAN and/or INN drug names selected from clopidogrel, ticagrelor, prasugrel, cangrelor, elinogrel, and ticlopidine. In a further aspect, a compound can be present as clopidogrel. In a yet further aspect, a compound can be present as ticagrelor. In a still further aspect, a compound can be present as prasugrel. In an even further aspect, a compound can be present as cangrelor. In a still further aspect, a compound can be present as elinogrel. In a yet further aspect, a compound can be present as ticlopidine.

The compounds of this invention can be prepared by employing reactions as disclosed in the references cited above, in addition to other standard manipulations that are known in the literature or clear to one skilled in the art. Suitable methods for synthesizing the disclosed compounds are provided in U.S. Pat. No. 7,101,860, U.S. Pat. No. 7,132,408, U.S. Pat. No. 7,368,438, U.S. Pat. No. 7,452,870, U.S. Pat. No. 7,452,870, U.S. Pat. No. 7,488,739, U.S. Pat.

In one aspect, a ADP-(P2Y$_{12}$)-like receptor modulator can be present as:

No. 7,504,497, U.S. Pat. No. 7,618,949, U.S. Pat. No. 7,696,168, U.S. Pat. No. 7,749,981, U.S. Pat. No. 7,749,981, U.S. Pat. No. 7,879,878, U.S. Pat. No. 7,910,576, U.S. Pat. No. 7,932,376, U.S. Pat. No. 7,943,760, US20050159388, US20050267134, US20060121086, US20060122143, US20060148806, US20060258614, US20070093446, US20070244088, US20080009523, US20080027103, US20080027104, US20080032992, US20080039437, US20080045494, US20080103304, US20080171732, US20080176827, US20080194576, US20080200448, US20080287671, US20080312208, US20090018166, US20090042852, US20090124617, US20090186876, US20090197834, US20090197834, US20090227555, US20090286834, US20090291962, US20090312368, US20090318464, US20100035895, US20100069350, US20100113391, US20100135999, US20100137277, US20100197913, US20100210654, US20100210654, US20100226918, US20100261678, US20100298350, US20110021537, US20110028484, US20110039829, US20110046089, and US20110059981. The methods of making disclosed in the foregoing are incorporated herein by reference in their entirety.

It is contemplated that one or more compounds can optionally be omitted from the disclosed invention.

C. MODULATION OF ADP-(P2Y12)-LIKE RECEPTOR ACTIVITY

In one aspect, the disclosed compounds exhibit modulation of ADP-($P2Y_{12}$)-like receptor activity. In a further aspect, the disclosed compounds are antagonists of ADP-($P2Y_{12}$)-like receptors. In a still further aspect, the disclosed compounds are inhibitors of ADP-($P2Y_{12}$)-like receptors. In a yet further aspect, the disclosed compounds are negative allosteric modulators of ADP-($P2Y_{12}$)-like receptors.

In a further aspect, the disclosed compounds exhibit selective inhibition of ADP-($P2Y_{12}$)-like receptors compared to other P2Y receptors. In a still further aspect, the disclosed compounds exhibit selective inhibition of individual members of the ADP-($P2Y_{12}$)-like receptor family. For example, a disclosed compound can selectively inhibit the $P2Y_{12}$ member of the ADP-($P2Y_{12}$)-like receptor family compared to either other members of the ADP-($P2Y_{12}$)-like receptor family or to other P2Y receptors generally. Alternatively, a disclosed compound can selectively inhibit a subset of the ADP-($P2Y_{12}$)-like receptor family compared to either other members of the family or to other P2Y receptors. For example, it is contemplated that a disclosed compound can selectively inhibit $P2Y_{12}$, $P2Y_{13}$, and $P2Y_{14}$ receptors.

In a further aspect, modulation of ADP-($P2Y_{12}$)-like receptor activity can affect the activity, protein expression, or subcellular localization of other proteins regulated by one or more ADP-($P2Y_{12}$)-like receptor. For example, negative modulation such as antagonism, inhibition, or negative allosteric modulation of one or more ADP-($P2Y_{12}$)-like receptors can inhibit or decrease the activity, protein expression, or subcellular localization of other proteins subject to control by one or more ADP-($P2Y_{12}$)-like receptors. In other cases, negative modulation such as antagonism, inhibition, or negative allosteric modulation of one or more ADP-($P2Y_{12}$)-like receptors can upregulate or increase the activity, protein expression, or subcellular localization of proteins subject to control by one or more ADP-($P2Y_{12}$)-like receptor regulatory pathways.

In a further aspect, modulation of ADP-($P2Y_{12}$)-like receptor activity can affect the expression of AQP2. For example, negative modulation such as antagonism, inhibition, or negative allosteric modulation of one or more ADP-($P2Y_{12}$)-like receptors can increase the level of AQP2 in the kidney. In a further aspect, negative modulation such as antagonism, inhibition, or negative allosteric modulation of one or more ADP-($P2Y_{12}$)-like receptors can increase the level of AQP2 in the kidney by about two-fold, by about five-fold, by about 10-fold, by about 20-fold, and by about 50-fold. It is contemplated that negative modulation such as antagonism, inhibition, or negative allosteric modulation of one or more ADP-($P2Y_{12}$)-like receptors can increase the level of AQP2 in the inner medulla of kidney. In a further aspect, negative modulation such as antagonism, inhibition, or negative allosteric modulation of one or more ADP-($P2Y_{12}$)-like receptors can increase the level of AQP2 in the inner medulla of the kidney by about two-fold, by about five-fold, by about 10-fold, by about 20-fold, and by about 50-fold. For example, inhibition of the $P2Y_{12}$ receptor can increase AQP2 protein levels in the kidney. In a further aspect, negative modulation such as antagonism, inhibition, or negative allosteric modulation of $P2Y_{12}$ can increase the level of AQP2 in the kidney by about 10%, by about 15%, by about 20%, by about 25%, by about 30%, by about 40%, by about 50%, by about 60%, by about 70%, by about 80%, by about 90%, by about 100%, by about 150%, by about 200%, by about 300%, by about 400%, by about 500%, by about 750%, and by about 1000%. It is further contemplated that inhibition of the $P2Y_{12}$ receptor can result in the upregulation in AQP2 protein levels in the inner medulla of the kidney. In an even further aspect, negative modulation such as antagonism, inhibition, or negative allosteric modulation of $P2Y_{12}$ can increase the level of AQP2 in the inner medulla of kidney by about 10%, by about 15%, by about 20%, by about 25%, by about 30%, by about 40%, by about 50%, by about 60%, by about 70%, by about 80%, by about 90%, by about 100%, by about 150%, by about 200%, by about 300%, by about 400%, by about 500%, by about 750%, and by about 1000%.

In a further aspect, modulation of ADP-($P2Y_{12}$)-like receptor activity can affect the levels of PGE2 in the urine. For example, negative modulation such as antagonism, inhibition, or negative allosteric modulation of one or more ADP-($P2Y_{12}$)-like receptors can decrease the levels of PGE2 metabolites in the urine. In a further aspect, negative modulation such as antagonism, inhibition, or negative allosteric modulation of one or more ADP-($P2Y_{12}$)-like receptors can decrease the level of PGE2 in the kidney by about 10%, by about 15%, by about 20%, by about 25%, by about 30%, by about 40%, by about 50%, by about 60%, by about 70%, by about 80%, by about 90%, by about 100%, by about 150%, by about 200%, by about 300%, by about 400%, by about 500%, by about 750%, and by about 1000%. It is contemplated that inhibition of the $P2Y_{12}$ receptor can decrease the levels of PGE2 in the urine. In a still further aspect, negative modulation such as antagonism, inhibition, or negative allosteric modulation of $P2Y_{12}$ can decrease the level of PGE2 metabolites in the kidney by about 10%, by about 15%, by about 20%, by about 25%, by about 30%, by about 40%, by about 50%, by about 60%, by about 70%, by about 80%, by about 90%, by about 100%, by about 150%, by about 200%, by about 300%, by about 400%, by about 500%, by about 750%, and by about 1000%.

In a further aspect, modulation of ADP-($P2Y_{12}$)-like receptor activity can affect physiological processes and functions. For example, negative modulation such as antagonism, inhibition, or negative allosteric modulation of one or more ADP-($P2Y_{12}$)-like receptors can have a salutary effect on pathophysiological processes and functions. In a still further aspect, negative modulation such as antagonism, inhibition, or negative allosteric modulation of one or more ADP-(P2Y$_{12}$)-like can have a salutary effect on acquired nephrogenic diabetes insipidus. In a further aspect, inhibition or antagonism of the P2Y$_{12}$ receptor can result in these effects when the acquired nephrogenic diabetes insipidus is induced by prior treatment of the subject with a lithium salt. In a still further aspect, or antagonism of the P2Y$_{12}$ receptor can result in these effects when the acquired nephrogenic diabetes insipidus is induced in by a lithium salt which is co-administered with a modulator of one or more ADP-(P2Y$_{12}$)-like receptors.

In a further aspect, modulation of ADP-(P2Y$_{12}$)-like receptor activity can reverse acquired nephrogenic diabetes in a subject. In a still further aspect, modulation of ADP-(P2Y$_{12}$)-like receptor activity can reverse acquired nephrogenic diabetes in a subject administered a lithium salt prior to administration of a modulator of ADP-(P2Y$_{12}$)-like receptor activity. In a further aspect, modulation of P2Y$_{12}$ receptor activity can reverse acquired nephrogenic diabetes in a subject. In a still further aspect, modulation of P2Y$_{12}$ receptor activity can reverse acquired nephrogenic diabetes in a subject administered a lithium salt prior to administration of a modulator of P2Y$_{12}$ receptor activity.

In a further aspect, modulation of ADP-(P2Y$_{12}$)-like receptor activity can prevent acquired nephrogenic diabetes in a subject. In a still further aspect, modulation of ADP-(P2Y$_{12}$)-like receptor activity can prevent acquired nephrogenic diabetes in a subject when the modulator of ADP-(P2Y$_{12}$)-like receptor activity is administered to a subject prior to treatment with a lithium salt. In a yet further aspect, modulation of ADP-(P2Y$_{12}$)-like receptor activity can prevent acquired nephrogenic diabetes in a subject when the modulator of ADP-(P2Y$_{12}$)-like receptor activity is co-administered to a subject with a lithium salt. In a further aspect, modulation of P2Y$_{12}$ receptor activity can prevent acquired nephrogenic diabetes in a subject. In a still further aspect, modulation of P2Y$_{12}$ receptor activity can prevent acquired nephrogenic diabetes in a subject when the modulator of P2Y$_{12}$ receptor activity is administered to a subject prior to treatment with a lithium salt. In a yet further aspect, modulation of ADP-P2Y$_{12}$ receptor activity can prevent acquired nephrogenic diabetes in a subject when the modulator of P2Y$_{12}$ receptor activity is co-administered to a subject with a lithium salt.

In a further aspect, modulation of ADP-(P2Y$_{12}$)-like receptor activity can affect the water intake in a subject with diabetes insipidus. In a further aspect, the subject has nephrogenic diabetes insipidus. In a yet further aspect, the subject has acquired nephrogenic diabetes insipidus. In a still further aspect, the subject has acquired nephrogenic diabetes insipidus induced by treatment with a lithium salt. In an even further aspect, the subject has acquired nephrogenic diabetes insipidus induced by with a lithium salt which is co-administered with a modulator of one or more ADP-(P2Y$_{12}$)-like receptors. For example, negative modulation such as antagonism, inhibition, or negative allosteric modulation of one or more ADP-(P2Y$_{12}$)-like receptors can decrease water intake in a subject with diabetes insipidus. In a further aspect, negative modulation such as antagonism, inhibition, or negative allosteric modulation of one or more ADP-(P2Y$_{12}$)-like receptors can decrease water intake in a subject with diabetes insipidus by about 15%, by about 20%, by about 25%, by about 30%, by about 40%, by about 50%, by about 60%, by about 70%, by about 80%, by about 90%, and by about 100%. For example, negative modulation such as antagonism, inhibition, or negative allosteric modulation of P2Y$_{12}$ can decrease water intake in a subject with diabetes insipidus. In a further aspect, negative modulation such as antagonism, inhibition, or negative allosteric modulation of P2Y$_{12}$ can decrease water intake in a subject with diabetes insipidus by about 15%, by about 20%, by about 25%, by about 30%, by about 40%, by about 50%, by about 60%, by about 70%, by about 80%, by about 90%, and by about 100%.

In a further aspect, modulation of ADP-(P2Y$_{12}$)-like receptor activity can affect the urine output in a subject with diabetes insipidus. In a further aspect, the subject has nephrogenic diabetes insipidus. In a yet further aspect, the subject has acquired nephrogenic diabetes insipidus. In a still further aspect, the subject has acquired nephrogenic diabetes insipidus induced by treatment with a lithium salt. In an even further aspect, the subject has acquired nephrogenic diabetes insipidus induced by with a lithium salt which is co-administered with a modulator of one or more ADP-(P2Y$_{12}$)-like receptors. For example, negative modulation such as antagonism, inhibition, or negative allosteric modulation of one or more ADP-(P2Y$_{12}$)-like receptors can decrease urine output in a subject with diabetes insipidus. In a further aspect, negative modulation such as antagonism, inhibition, or negative allosteric modulation of one or more ADP-(P2Y$_{12}$)-like receptors can decrease urine output in a subject with diabetes insipidus by about 15%, by about 20%, by about 25%, by about 30%, by about 40%, by about 50%, by about 60%, by about 70%, by about 80%, by about 90%, and by about 100%. For example, negative modulation such as antagonism, inhibition, or negative allosteric modulation of P2Y$_{12}$ can decrease urine output in a subject with diabetes insipidus. In a further aspect, negative modulation such as antagonism, inhibition, or negative allosteric modulation of P2Y$_{12}$ can decrease urine output in a subject with diabetes insipidus by about 15%, by about 20%, by about 25%, by about 30%, by about 40%, by about 50%, by about 60%, by about 70%, by about 80%, by about 90%, and by about 100%.

In a further aspect, modulation of ADP-(P2Y$_{12}$)-like receptor activity can affect the urine osmolality in a subject with diabetes insipidus. In a further aspect, the subject has nephrogenic diabetes insipidus. In a yet further aspect, the subject has acquired nephrogenic diabetes insipidus. In a still further aspect, the subject has acquired nephrogenic diabetes insipidus induced by treatment with a lithium salt. In an even further aspect, the subject has acquired nephrogenic diabetes insipidus induced by with a lithium salt which is co-administered with a modulator of one or more ADP-(P2Y$_{12}$)-like receptors. For example, negative modulation such as antagonism, inhibition, or negative allosteric modulation of one or more ADP-(P2Y$_{12}$)-like receptors can increase urine osmolality in a subject with diabetes insipidus. In a further aspect, negative modulation such as antagonism, inhibition, or negative allosteric modulation of one or more ADP-(P2Y$_{12}$)-like receptors can increase urine osmolality in a subject with diabetes insipidus by about 15%, by about 20%, by about 25%, by about 30%, by about 40%, by about 50%, by about 60%, by about 70%, by about 80%, by about 90%, by about 100%, by about 150%, by about 200%, by about 250%, and by about 300%. For example, negative modulation such as antagonism, inhibition, or negative allosteric modulation of P2Y$_{12}$ can increase urine osmolality in a subject with diabetes insipidus. In a further aspect, negative modulation such as antagonism, inhibition, or negative allosteric modulation of P2Y$_{12}$ can increase urine osmolality in a subject with diabetes insipidus by about 15%, by about 20%, by about 25%, by about 30%, by about 40%, by about 50%, by about 60%, by about 70%, by about 80%, by about 90%, by about 100%, by about 150%, by about 200%, by about 250%, and by about 300%.

In a further aspect, modulation of ADP-($P2Y_{12}$)-like receptor activity can affect the urinary AVP levels in a subject with diabetes insipidus. In a further aspect, the subject has nephrogenic diabetes insipidus. In a yet further aspect, the subject has acquired nephrogenic diabetes insipidus. In a still further aspect, the subject has acquired nephrogenic diabetes insipidus induced by treatment with a lithium salt. In an even further aspect, the subject has acquired nephrogenic diabetes insipidus induced by with a lithium salt which is co-administered with a modulator of one or more ADP-($P2Y_{12}$)-like receptors. For example, negative modulation such as antagonism, inhibition, or negative allosteric modulation of one or more ADP-($P2Y_{12}$)-like receptors can increase urinary AVP levels in a subject with diabetes insipidus. In a further aspect, negative modulation such as antagonism, inhibition, or negative allosteric modulation of one or more ADP-($P2Y_{12}$)-like receptors can increase urinary AVP levels in a subject with diabetes insipidus by about 15%, by about 20%, by about 25%, by about 30%, by about 40%, by about 50%, by about 60%, by about 70%, by about 80%, by about 90%, by about 100%, by about 150%, by about 200%, by about 250%, and by about 300%. For example, negative modulation such as antagonism, inhibition, or negative allosteric modulation of $P2Y_{12}$ can increase urinary AVP levels in a subject with diabetes insipidus. In a further aspect, negative modulation such as antagonism, inhibition, or negative allosteric modulation of $P2Y_{12}$ can increase urinary AVP levels in a subject with diabetes insipidus by about 15%, by about 20%, by about 25%, by about 30%, by about 40%, by about 50%, by about 60%, by about 70%, by about 80%, by about 90%, by about 100%, by about 150%, by about 200%, by about 250%, and by about 300%.

In a further aspect, modulation of ADP-($P2Y_{12}$)-like receptor activity can affect the serum lithium levels in a subject treated with a lithium salt. In a further aspect, the subject has diabetes insipidus. In an even further aspect, the subject has nephrogenic diabetes insipidus. In a yet further aspect, the subject has acquired nephrogenic diabetes insipidus. In a still further aspect, the subject has acquired nephrogenic diabetes insipidus induced by treatment with a lithium salt. In an even further aspect, the subject has acquired nephrogenic diabetes insipidus induced by with a lithium salt which is co-administered with a modulator of one or more ADP-($P2Y_{12}$)-like receptors. For example, negative modulation such as antagonism, inhibition, or negative allosteric modulation of one or more ADP-($P2Y_{12}$)-like receptors can increase serum lithium levels in a subject with diabetes insipidus. In a further aspect, negative modulation such as antagonism, inhibition, or negative allosteric modulation of one or more ADP-($P2Y_{12}$)-like receptors can increase serum lithium levels in a subject with diabetes insipidus by about 5%, by about 10%, by about 15%, by about 20%, by about 25%, by about 30%, by about 35%, by about 50%, by about 60%, by about 80%, by about 90%, and by about 100%. For example, negative modulation such as antagonism, inhibition, or negative allosteric modulation of $P2Y_{12}$ can increase serum lithium levels in a subject with nephrogenic diabetes insipidus. In a further aspect, negative modulation such as antagonism, inhibition, or negative allosteric modulation of $P2Y_{12}$ can increase serum lithium levels in a subject with diabetes insipidus by about 5%, by about 10%, by about 15%, by about 20%, by about 25%, by about 30%, by about 35%, by about 50%, by about 60%, by about 80%, by about 90%, and by about 100%. Alternatively, negative modulation such as antagonism, inhibition, or negative allosteric modulation of one or more ADP-($P2Y_{12}$)-like receptors can increase serum lithium levels in a subject with diabetes insipidus. In a further aspect, negative modulation such as antagonism, inhibition, or negative allosteric modulation of one or more ADP-($P2Y_{12}$)-like receptors can decrease serum lithium levels in a subject with diabetes insipidus by about 5%, by about 10%, by about 15%, by about 20%, by about 25%, by about 30%, by about 35%, by about 50%, by about 60%, by about 80%, by about 90%, and by about 100%. For example, negative modulation such as antagonism, inhibition, or negative allosteric modulation of $P2Y_{12}$ can decrease serum lithium levels in a subject with nephrogenic diabetes insipidus. In a further aspect, negative modulation such as antagonism, inhibition, or negative allosteric modulation of $P2Y_{12}$ can decrease serum lithium levels in a subject with diabetes insipidus by about 5%, by about 10%, by about 15%, by about 20%, by about 25%, by about 30%, by about 35%, by about 50%, by about 60%, by about 80%, by about 90%, and by about 100%.

In a further aspect, modulation of ADP-($P2Y_{12}$)-like receptor activity can be determined using an in vitro assay. There are several suitable assays known to one skilled in the art. In a still further aspect, modulation of ADP-($P2Y_{12}$)-like receptor activity can be determined using a recombinant cell membrane binding assay. For example, cells are transfected with an expression construct comprising a heterologous nucleic acid for the ADP-($P2Y_{12}$)-like receptor of interest, e.g. $P2Y_{12}$. Briefly, cells are exposed a radiolabeled reporter ligand that binds to the target ADP-($P2Y_{12}$)-like receptor and various concentrations of a test compound or prospective modulator of ADP-($P2Y_{12}$)-like receptor activity. For example, a suitable radiolabeled reporter ligand to assay activity of $P2Y_{12}$ is tritium-labeled 2-methyl-thio-adenosine 5'-diphosphate (2-methyl-S-ADP). Following incubation for a suitable period and a suitable temperature, e.g. about room temperatures for about 1-2 hours, the cells are washed. Next, the cells are solubilized and the solubilized cells are transferred to a scintillation vial for determination of the amount of radioactivity bound to the cells.

In a further aspect, the disclosed modulators of ADP-($P2Y_{12}$)-like receptor activity inhibit binding of a radiolabeled receptor ligand in a cell membrane bind assay. In a still further aspect, the disclosed modulators of ADP-($P2Y_{12}$)-like receptor activity inhibit binding of a radiolabeled receptor ligand with an $IC_{50}$ of about 100 µM, about 10 µM, about 5 µM, about 1 µM, about 0.1 µM, about 0.05 µM, about 0.01 µM, about 0.005 µM, and about 0.001 µM. In a yet further aspect, the modulators of ADP-($P2Y_{12}$)-like receptor show selectivity compared to non-ADP-($P2Y_{12}$)-like receptors. In an even further aspect, modulators of ADP-($P2Y_{12}$)-like receptor are selective compared to $P2Y_2$. In a yet further aspect, modulators of ADP-($P2Y_{12}$)-like receptor have an $IC_{50}$ for ADP-($P2Y_{12}$)-like receptors about 5-fold lower, about 10-fold lower, about 25-fold lower, about 50-fold lower, about 100-fold lower, about 200-fold lower, and about 500-fold lower than for non-ADP-($P2Y_{12}$)-like receptors. In a still further aspect, modulators of ADP-($P2Y_{12}$)-like receptor have an $IC_{50}$ for ADP-($P2Y_{12}$)-like receptors about 5-fold lower, about 10-fold lower, about 25-fold lower, about 50-fold lower, about 100-fold lower, about 200-fold lower, and about 500-fold lower than for $P2Y_2$ receptors.

In a further aspect, the disclosed modulators of $P2Y_{12}$ activity inhibit binding of a radiolabeled receptor ligand in a cell membrane bind assay. In a still further aspect, the disclosed modulators of $P2Y_{12}$ activity inhibit binding of a radiolabeled receptor ligand with an $IC_{50}$ of about 100 µM, about 10 µM, about 5 µM, about 1 µM, about 0.1 µM, about 0.05 µM, about 0.01 µM, about 0.005 µM, and about 0.001 µM. In a yet further aspect, the modulators of $P2Y_{12}$ show selectivity compared to other P2Y receptors. In an even further aspect, modulators $P2Y_{12}$ are selective compared to $P2Y_2$. In a yet further aspect, modulators of $P2Y_{12}$ have an $IC_{50}$ for $P2Y_{12}$ about 5-fold lower, about 10-fold lower, about 25-fold lower, about 50-fold lower, about 100-fold lower, about 200-fold lower, and about 500-fold lower than for non-$P2Y_{12}$ receptors. In a still further aspect, modulators of $P2Y_{12}$ have an $IC_{50}$ for $P2Y_{12}$ about 5-fold lower, about 10-fold lower, about 25-fold lower, about 50-fold lower, about 100-fold lower, about 200-fold lower, and about 500-fold lower than for $P2Y_2$ receptors.

D. PURINERGIC RECEPTORS

Several cell membrane receptors, which preferentially bind extracellular nucleotides (ATP/UTP/ADP), and their analogues have been identified, cloned and characterized. There receptors, collectively known as extracellular nucleotide receptors or purinergic receptors have been classified based on their molecular biology, biological actions and pharmacology. Broadly they are divided into P2Y and P2X families. (P1 receptors are not nucleotide receptors; they are adenosine receptors). The P2X receptors are ionotrophic ATP-gated channels that open up to allow small molecules to enter into the cells. Purinergic regulation of renal function encompasses glomerular hemodynamics, microvascular function, tubuloglomerular feedback, tubular transport, renal cell growth and apoptosis for example (Schwiebert and Kishore, 2001; Inscho, 2001).

There are two main families of purine receptors, adenosine or P1 receptors, and P2 receptors, recognizing primarily ATP, ADP, UTP, and UDP (Table 1). Adenosine/P1 receptors couple to G proteins and have been further subdivided, based on molecular, biochemical, and pharmacological evidence into four subtypes, $A_1$, $A_{2A}$, $A_{2B}$, and $A_3$. In contrast, P2 receptors divide into two families of ligand-gated ion channels and G protein-coupled receptors termed P2X and P2Y receptors, respectively. For example, Table 1 sets forth seven mammalian P2X receptors ($P2X_{1-7}$) and eleven mammalian P2Y receptors ($P2Y_1$, $P2Y_2$, $P2Y_4$, $P2Y_6$, $P2Y_8$, $P2Y_9$, $P2Y_{10}$, $P2Y_{11}$, $P2Y_{12}$, $P2Y_{13}$, and $P2Y_{14}$) which have been cloned and characterized.

TABLE I

Families of receptors for purines and pyrimidines*

|  | Adenosine/P1 receptors | P2 receptors | |
|---|---|---|---|
| Natural ligands | Adenosine | ATP, ADP, UTP, UDP, Adenine dinucleotides | |
| Subgroup | — | P2X | P2Y |
| Type | G protein-coupled | Ion channel Nonselective pore | G protein-coupled |
| Subtypes | $A_1$, $A_{2A}$, $A_{2B}$, $A_3$ | $P2X_{1-7}$, $P2X_n$ | $P2Y_1$, $P2Y_2$, $P2Y_4$, $P2Y_6$, $P2Y_8$, $P2Y_9$, $P2Y_{10}$, $P2Y_{11}$, $P2Y_{12}$, $P2Y_{13}$, $P2Y_{14}$, |

*Modified from Ralevic V, Burnstock G. (1998) Pharmacol Rev 50(3): 413-92, and updated with information from Abbracchio, M. P., et al. (2006) Pharmacol. Rev. 58(3): 281-341.

P2Y receptors are purine and pyrimidine nucleotide receptors that are coupled to G proteins. Most P2Y receptors act via G protein coupling to activate PLC leading to the formation of $IP_3$ and mobilization of intracellular $Ca^{2+}$. Coupling to adenylate cyclase by some P2Y receptors has also been described. The response time of P2Y receptors is longer than that of the rapid responses mediated by P2X receptors because it involves second-messenger systems and down stream mediators mediated by G protein coupling. Eleven mammalian P2Y receptors have been isolated and cloned (see Table I). The various P2Y receptors have been functionally characterized and show distinct pharmacological profiles.

P2Y receptors are about 308 to 377 amino acid proteins with a mass of 41 to 53 kDa after glycosylation. A model of the P2Y receptor, based on the primary sequence of the $P2Y_1$ receptor and using the structural homolog rhodopsin as a G protein-coupled receptor template, has identified positively charged amino acid residues in transmembrane regions 3, 6, and 7 that may be involved in ligand binding by electrostatic interactions with the phosphates of ATP (Van Rhee et al., 1995). Several of these amino acids are conserved in other G protein-coupled receptors. Site-directed mutagenesis of the $P2Y_2$ receptor to convert positively charged amino acids in transmembrane regions 6 and 7 to neutral amino acids causes a 100- to 850-fold decrease in the potency of ATP and UTP, which suggests a role for these amino acids in binding purines and pyrimidines (Erb et al., 1995).

E. USE OF LITHIUM AS A THERAPEUTIC AGENT

Lithium and the salts thereof have been used to treat a variety of disorders. The initial medicinal use of lithium salts was in the treatment of gout (Cade, J. F. J. (1970) Discoveries in biological psychiatry (Ayd, F. J., Jr., and Blackwell, B., Eds.) pp 218-229, J. B. Lippincott, Philadelphia/Toronto). The mechanism of this function relied on the relative solubility of lithium urate, leading to the dissolution of urate deposits in the cartilage. The efficacy of lithium in the treatment of viral disorders has also been suggested (Jefferson, J. W. (1990) Journal of Clinical Psychiatry 51 (suppl 8):4-8). Lithium has been shown to inhibit the replication of DNA viruses such as those in the herpes simplex family Rybakowski, J. (2000) Pharmacopsychiatry 33:159-164; Skinner, G., et al. (1980) Medical Microbiology and Immunology 168, 139-148). Accordingly, a lithium ointment was developed and was shown to improve the status of patients suffering from genital herpes (Skinner, G. (1983) Lancet 2:288).

Lithium is approved by the U.S. FDA for the maintenance treatment of bipolar disorder and acute treatment of manic episodes of bipolar disorder. However, it is also prescribed for unlabeled uses such as treatment of neutropenia; unipolar depression; schizoaffective disorder; prophylaxis of cluster headaches; premenstrual tension; tardive dyskinesia; hyperthyroidism; SIADH, postpartum affective psychosis; corticosteroid-induced psychosis. Typical dosages in adult are oral administration of 900-1,800 mg/day in 2 to 4 divided doses, with a maximum daily dose of 2,400 mg/day. Pediatric dosages (in children 12 years of age and older) are 15-20 mg/kg/day administered in 2 to 3 divided doses. It should be understood that "lithium" refers to a lithium salt and not elemental lithium, and is typically in the form of lithium carbonate. Lithium citrate has also been used in lieu of lithium carbonate as a therapeutic agent. The pharmaceutical form of lithium has been sold under such brand names as Lithotabs, Lithonate, Lithobid, Lithane, and Eskalith. Most commonly, it is simply referred to by the USAN/INN name of lithium carbonate or lithium citrate.

The most prevalent uses of lithium are in the treatment of acute or chronic bipolar disorder and in the prevention of bipolar disorder recurrence in individuals who have experienced transient episodes. Bipolar disorder is estimated to affect approximately one percent of people throughout the world (Woods, S. W. (2000) J. Clin. Psych. 61 (suppl 13), 38-41). In the U.S., about 2% of the population affected (Lenox et al, 1998, J Clin Psychiatry 58:37-47), with double that prevalence in war veterans. Mental depression and substance abuse, which are often encountered in post-traumatic stress disorder (PTSD) patients, such as war veterans, are known to predispose them to bipolar disorder. The incidence of PTSD among the veterans of recent wars in Afghanistan and Iraq has been reported to be very high (Hoge et al, 2004, New Eng J Med 351:13-22). Furthermore, no studies are available on the incidence of PTSD among civilians in combat zones. Apart from wars, PTSD can also result from physical or sexual abuse in childhood, physical or sexual assault in adults, serious accidents, terrorist attacks, natural disasters such as fire, tornado, hurricane, flood, tsunami or earthquake etc. So, the incidence of PTSD is prone to increase even in the general population with increasing violent acts or tragic incidents in the society.

The disease is characterized by alternating episodes of mania and depression. Bipolar disorder, also known as manic depression, can lead to unpredictable behavior and is associated with an increased risk of suicide. The economic burden of the disease is significant. For example, Begley and colleagues (Begley C. E., et al (2001) Pharmacoeconomics 19:483-495) determined that the lifetime cost for persons with bipolar disorder was $24 billion in 1998, whereas Wyatt and Henter (Wyatt R. J. and Henter I. (1995) Soc. Psych. Psych. Epid. 30:213-219) calculated a cost of $45 billion in a 1991 sample. In the study by Begley and colleagues, average lifetime cost per case ranged from $11,720 for persons with a single manic episode to $624,785 for persons with nonresponsive or chronic episodes.

Many professional associations recommend lithium as the first treatment option for patients suffering with bipolar disorder (reviewed in Goldberg, H., et al. (1988) Am. J. Physiol. 255:F995-F1002). Approximately half of all patients for whom lithium is prescribed will experience a diminution of their symptoms (Nemeroff, C. B. (2000) J. Clin. Psych. 61(suppl 13):19-25). Further improvements in the results obtained with lithium therapy are gained through the combination of lithium with other anti-bipolar agents (Bowden, C. (2000) J. Clin. Psych. 61(Suppl 9):35-40). In the field of non-bipolar psychological disorders, lithium has been used to treat maladies ranging from alcoholism to unipolar depression (for review see Bowden, ibid). In the treatment of these psychological disorders, lithium is often prescribed as an augmentation of therapy when a patient is unresponsive to conventional treatment regimens.

The broad applicability of lithium across a spectrum of disorders is due, in part, to its pleiotropic effects on numerous mammalian organs, including the brain, kidneys, and other major organs. Lithium has been shown to cause a significant rise in the concentration of magnesium in the plasma due to effects on choroid plexus transport (Birch, N. J., et al. (1973) Br. J. Pharmacol. Chemotherap. 47:586-594; Reed and Yen, ibid). These data are consistent with a model that the effect of lithium on magnesium transport through the choroid plexus structure of the brain might be a factor in the attenuation of mood disorders. In addition, structural studies of the brains of patients suffering from bipolar disorder have shown a correlation between the disease and ventricular volume (Chen, G., et al. (2000) J. Neurochem. 75:1729-1734; Drevets, W. C., et al. (1997) Nature 38, 824-827; Sheline, Y. I., et al. (1999) J. Neurosci. 19:5034-5043; Sheline, Y. I., et al. (1996) Proc. Natl. Acad. Sci. USA 93:3908-3913; Soares, J. C., et al. (1997) Biol. Psych. 41:86-106). Because the volume of the brain is held constant by the rigid support of the skull, an increased ventricular volume means that the volume of the hippocampus and other structures are decreased. Lithium has been shown to alleviate this effect (Chen, G., et al., ibid).

In addition to its positive effects on mood disorders and other human ailments, lithium exhibits a plethora of negative effects on human systems (for review see Waring, W. S. (2006) Toxicol. Rev. 25:221-230). Thus, despite the efficacy and relatively low cost of lithium treatment, alternatives are constantly being sought. Lithium is associated with numerous side effects, including nausea, diarrhea, and kidney dysfunction. In addition, continuous monitoring of serum lithium concentrations is required, because overdose can quickly lead to coma and death (Bowden, C. (2000) J. Clin. Psych. 61(Suppl 9):35-40). These side effects lead to problems with a lack of adherence to recommended therapeutic regimens in a large percentage of patients (Scott, J., et al. (2002) J. Clin. Psych. 63:384-390). In its most drastic manifestation, lithium can cause death in a variety of ways. Overdose can induce a shutdown of the nervous system, leading to coma and brain death. Lithium can also cause death through the induction of organ failure, particularly in susceptible patients such as the elderly and people with pre-existing heart and kidney disease.

More benign and yet more common side effects include afflictions of the kidneys, the gastrointestinal tract, and the thyroid (for review, see Schou, M. (2001) J. Affect. Disord. 67:21-32; Timmer, R. T. and Sands, J. M. (1999) J. Am. Soc. Nephrol. 10(3):666-74). Urinary-concentrating defects arising in the kidney are common complaints among patients undergoing lithium therapy. Up to 20% of patients report clinically significant polyuria, in which daily urinary output can reach 10 L or more (Boton, R., et al. (1987) Am. J. Kid. Dis. 10:329-345). Secondary to this effect is polydipsia, in which excessive thirst forces patients to consume vast quantities of liquid to maintain body fluid levels in the face of such high urine volumes. Acquired nephrogenic diabetes insipidus (NDI) is a hallmark of lithium treatment, occurring in 20-50% of patients taking the drug (Boton, ibid). Lithium-induced NDI is thought to arise from an interaction of the drug with the vasopressin (AVP)-activated adenylate cyclase system in the collecting ducts of the kidney (Christensen, S., et al. (1985) J. Clin. Invest. 75:1869-1879; Goldberg, ibid; Jackson, B. A., et al. (1980) Endocrinol. 107:1693-1698; Yamaki, M., et al. (1991) Am. J. Physiol. 261:F505-F511).

Lithium treatment is also associated with the occurrence of diarrhea (Gelenberg, A. J., et al. (1989) N. Eng. J. Med. 321:1489-1493). However, one reported pharmacological effect of lithium is in the prevention of secretory diarrhea arising from diverse causes (Donowitz, M., et al. (1986) Rev. Infect. Dis. 8:S188-S201). Oral lithium carbonate therapy has been reported to improve the status of patients suffering from diarrhea due to pancreatic cholera (Pandol, S. J., et al. (1980) N. Eng. J. Med. 302:1403-1404) and diarrhea of unknown etiology (Owyang, C. (1984) Gastroenterol. 87:714-718). The result of lithium therapy has been attributed to inhibition of the generation of cAMP (Owyang, ibid; Pandol, ibid). Another trial attempting to treat the diarrhea associated with pancreatic cholera syndrome resulted in exacerbation of the symptoms (Graham, D. Y., et al. (1975) Ann. Int. Med. 83:782-785; Graham, D. Y. (1980) N. Eng. J. Med. 303:1063-1064), indicating that diarrhea does not universally respond to lithium therapy.

Finally, a small percentage of those taking lithium experience hypothyroidism and its associated symptoms (Dwight, T., et al. (2002) Eur. J. Endocrinol. 146:619-627; Henry, C. (2002) J. Psych. Neurosci. 27:104-107).

Despite the risks associated with lithium treatment, it continues to be widely prescribed as a treatment for numerous disorders. For example, an extensive review of the use of lithium in the recent past concluded that it "continues to set a standard that has yet to be met by any proposed alternative mood-stabilizing treatments" (Baldessarini, R. J., et al. (2002) Harv. Rev. Psych. 10:59-75). Furthermore, despite the advent of newer drugs, lithium is still an important medication in the psychiatric armamentarium by virtue of significantly lower suicidal risk in lithium-treated patients. Moreover, advances in the pharmacotherapeutics of bipolar disorder over the past 10-20 years have been predominantly in terms of tolerability and safety, with no new treatments being demonstrated to be more efficacious than lithium (Mitchelle and Malhi, 2006, Expert Opin Emerg Drugs 11:621-634).

F. ACQUIRED NEPHROGENIC DIABETES INSIPIDUS

Acquired nephrogenic diabetes insipidus (NDI), which is relatively common, comprises several clinical conditions, such as lithium-induced nephropathy, hypokalemic nephropathy, hypercalcemia, and post-obstructive uropathy. The hallmark of these conditions is low protein levels of vasopressin-regulated water channel AQP2 in the medullary collecting duct, in the presence of normal or elevated circulating levels of arginine vasopressin (AVP). In both human patients and in experimental animals with acquired NDI, the production of renal prostaglandins such as PGE2 is increased. PGE2, by virtue of its ability to antagonize AVP-stimulated water permeability via retrieval of AQP2 water channels from the apical membrane of inner medullary collecting duct (IMCD), has been proposed to be involved in the development of polyuria of acquired NDI. In support of this, inhibition of PGE2 synthesis by the administration of indomethacin was shown to ameliorate the polyuria of acquired NDI. In rat IMCD, agonist stimulation of P2Y2 purinergic (nucleotide) receptor results in production and release of PGE2 (Welch et al, 2003), and this response is markedly enhanced in hydrated polyuric rats (Sun et al, 2004). It has been shown that the purinergic-mediated PGE2 release in IMCD is also markedly enhanced in acquired NDI induced by lithium (Li) administration or by bilateral ureteral obstruction (BUO) and release (Zhang, et al. (2009) Am. J. Physiol. Renal Physiol. 260:F1194-F1201; Zhang, et al. (2010) Am. J. Physiol. Renal Physiol. 295:F1715-F1724) And this is associated with significant increases in mRNA expression of cyclooxygenases-1 and/or -2 in the inner medulla of acquired NDI rats.

Diabetes insipidus (DI) causes considerable morbidity and inconvenience to the patients. Patients with DI, especially those critically ill, are at higher risk of dehydration, hypernatremia, alterations in the level of consciousness, and hemodynamic instability from hypovolemia, for example (Bell, 1994). Acquired nephrogenic diabetes insipidus (NDI), the more common form of NDI, can occur at any age. The most common cause of acquired NDI is lithium administration for the treatment of bipolar disorders. Other drugs that are capable of inducing acquired NDI are colchicine, methoxyflurane, amphotericin B, gentamicin, loop diuretics, and demeclocycline, for example. In addition to drugs, acquired NDI can also occur as a result of certain diseases. These include, but are not limited to chronic kidney diseases, hypokalemia, hypercalcemia, sickle cell disease, ureteral obstruction (obstructive uropathy), and low protein diet. The hallmark of these conditions, as documented in animal models, is low protein abundance of AVP-regulated water channel AQP2 in the medullary collecting duct in the face of normal or elevated circulating levels of AVP (See FIG. 1 of Nielsen et al, 1999). Thus, in these conditions, it appears that the inherent defect lies in the collecting duct.

The collecting duct system, which expresses AQP2, AQP3 and AQP4 water channels, accounts for the absorption of 15-20% of the filtered water. This is precisely regulated by AVP, and thus it is crucial for the conservation of body water and excretion of concentrated urine. AQP2 water channel, expressed on the apical plasma membrane and on sub-apical vesicles of collecting duct principal cells, is regulated by AVP. AVP, acting through its V2 receptor, a G protein-coupled receptor, on the collecting duct principal cells, activates membrane bound adenylyl cyclase (AC) to produce cAMP as a second messenger (See FIG. 2 of Kishore et al. Signalling vol 5, pp 491-499, 2009). The cellular effects of cAMP are believed to be connected to the activation of protein kinase A (PKA), which phosphorylates various key proteins. AVP has both short- and long-term effects on the collecting duct water permeability. The short-term regulation (in the time frame of few to several minutes) of collecting duct water permeability by AVP involves the translocation of AQP2 water channels from a pool of sub-apical vesicles to the apical plasma membrane (Nielsen et al, 1995). The apical plasma membrane is the rate-limiting barrier for the transepithelial water movement, as AQP3, AQP4 are constitutively expressed on the basolateral domain of the collecting duct principal cells under normal conditions. The long term-regulation (within the time frame of several hours to days) of collecting duct water permeability involves a parallel increase in the absolute amount of AQP2 mRNA and protein (Agre, 2000; Krane and Kishore, 2003). Water deprivation and vasopressin stimulation both increase AQP2 protein expression and apical membrane targeting (Nielsen et al, 1993; DiGiovanni et al, 1994; Kishore et al, 1996). cAMP is capable of stimulating AQP2 gene transcription by acting through CRE and AP1 sites in the AQP2 promoter (Hozawa et al, 1996; Yasui et al, 1997; Matsumura et al, 1997). cAMP activation of AQP2 gene likely occurs by phosphorylation of CREB (CRE binding protein) and the ability of phosphorylated CREB to activate AQP2 gene transcription via binding to CRE sites in the AQP2 promoter. cAMP activation of AQP2 gene could also occur by the induction of c-Fos expression and c-Fos activation of AQP2 transcription via the AP1 site in the AQP2 promoter.

Apart from AVP, a variety of autocrine and paracrine agents, such as PGE2, endothelin and extracellular nucleotides (ATP/UTP), also regulate the collecting duct water permeability. Acting via their respective receptors and the accompanying phosphoinositide signaling pathway these agents decrease the osmotic water permeability of the collecting duct, even in the presence of AVP (Nadler et al, 1992; Kohan and Hughe, 1993; Kishore et al, 1995; Roman and Lechene, 1981; Rouch and Kudo, 2000). Thus, in the collecting duct, cyclic AMP and phosphoinositide systems are mutually opposing signaling pathways (Teitelbaum, 1992). Diacylglycerol (DAG) formed as a result of stimulation of PI signaling pathway stimulates the activity of PKC, which in turn induces the activity of $G_i$ (inhibitory G protein) associated with the V2 receptor complex. Activation of $G_i$ uncouples the signal from V2 receptor to adenylyl cyclase (AC), resulting in decreased cellular cAMP levels. Activation of PI signaling pathway also results in the stimulation of specific phoshodiesterases (PDEs) through the calcium-calmodulin (CaM) pathway. These PDEs rapidly hydrolyze cAMP and thus reduce the water permeability of the collecting duct as demonstrated in DI+/+mice, which exhibit constitutively active cAMP-PDE (PDE type IV) (Homma et al, 1991; Frokiær et al, 1999)

Both in human patients and in laboratory animals, lithium-induced NDI and post-obstructive uropathy are associated with increased production and excretion of PGE2 in urine. And administration of indomethacin ameliorated these polyuric conditions, indicating that PGE2 is involved in the genesis of polyuria (Laszlo et al, 1980; Fradet et al, 1980, 1988; Sugawara et al, 1998). PGE2 is a major prostanoid in the kidney and it interacts with four G protein-coupled E-prostanoid receptors designated EP1, EP2, EP3 and EP4. Through these receptors, PGE2 modulates renal hemodynamics and salt and water excretion (Breyer and Breyer, 2000). PGE2 has an antagonistic effect on AVP-stimulated collecting duct water permeability (Nadler et al, 1992; Han et al, 1994), and molecular mechanisms of this effect of PGE2 on AVP-stimulated water permeability in renal collecting duct have been shown. Using ex-vivo preparations of renal medulla, Zelenina et al (2000) have demonstrated that agonist stimulation of EP3 prostanoid receptor causes retrieval of AQP2 water channels from the apical membrane, thus reducing the abundance of AQP2 protein in the apical membrane, the rate-limiting barrier in the transepithelial water movement in the collecting duct.

G. METHODS OF SCREENING COMPOUNDS

Disclosed are methods of identifying an antagonist of $P2Y_{12}$ receptors comprising the steps of contacting a kidney cell with an agent to be tested and detecting a decrease in PGE2 or PGE2 metabolite. A decrease in PGE2 indicates a $P2Y_{12}$ antagonist.

Also disclosed are methods of identifying an antagonist of $P2Y_{12}$ receptors comprising the steps of contacting a kidney cell with an agent to be tested and detecting an increase in AQP2 in the kidney collecting ducts. An increase in AQP2 indicates a compound is a $P2Y_{12}$ antagonist.

Also disclosed are methods of screening for an antagonist of $P2Y_{12}$, comprising contacting a kidney cell with a test compound; detecting the levels of PGE2 or a PGE2 metabolite in a kidney cell; and screening for a sustained reduction in PGE2 as compared to a control level, indicating an antagonist of $P2Y_{12}$.

The above is generally applicable for measuring PGE2 levels whether by fluorescence, luminescent or other detection techniques. The process is also applicable for screening compounds with biological activity characterized by rapid and transient changes in PGE2. Examples include the evaluation of receptor antagonists that elicit changes in cellular PGE2 levels.

The invention also provides methods of screening for $P2Y_{12}$ receptor antagonist, comprising contacting a first kidney cell with more than one test compound; detecting levels of PGE2 or a PGE2 metabolite in the first kidney cell; selecting each of test compounds in the group that contacted the first kidney cell, wherein the first kidney cell showed a sustained decrease in PGE2 or a PGE2 metabolite; contacting a second kidney cell with one test compound from the step of selecting each of the test compounds; and detecting levels of PGE2 or a PGE2 metabolite in the second kidney cell, a sustained decrease in PGE2 as compared to a control level, indicating a $P2Y_{12}$ antagonist.

Also disclosed are methods of screening for an antagonist of $P2Y_{12}$, comprising contacting a kidney cell with a test compound; detecting AQP2 levels in the kidney tubule collecting ducts; and screening for a sustained increase in AQP2 levels as compared to a control level, indicating an antagonist of P2Y2.

The invention also provides methods of screening for a $P2Y_{12}$ receptor antagonist, comprising contacting a first kidney cell with more than one test compound; detecting AQP2 in the kidney tubules of the first kidney cell; selecting each of test compounds in the group that contacted the first kidney cell, wherein the first kidney cell showed a sustained increase in AQP2 in the kidney tubules; contacting a second kidney cell with one test compound from the step of selecting each of the test compounds; and detecting AQP2 levels in the kidney tubules of the second kidney cell, a sustained increase in AQP2 levels in the kidney tubules as compared to a control level, indicating a $P2Y_{12}$ antagonist.

Also provided are methods of screening for a $P2Y_{12}$ antagonist, comprising contacting a test compound with a cell that expresses a heterologous nucleic acid that encodes a $P2Y_{12}$ receptor; and detecting levels of PGE2 or a PGE2 metabolite in the cell; a sustained reduction in PGE2 as compared to a control level, indicating a $P2Y_{12}$ antagonist. Preferably, the cell is a cell that lacks the receptor prior to introduction of the heterologous nucleic acid. The cell can be transiently transfected with the heterologous nucleic acid. For example, a suitable cell, e.g. HEK293, HeLa, or MDCK cells, can be transfected with an expression construct comprising the heterologous nucleic acid comprising the sequence of an ADP-($P2Y_{12}$)-like receptor. The transfected cells can be transiently transfected with the expression construct. Alternatively, permanent cell-lines expressing the ADP-($P2Y_{12}$)-like receptor can be selected by methods known to one skilled in the art, e.g. the expression construct can contain a suitable selection marker such as resistance to G418.

By "heterologous nucleic acid" is meant that any heterologous or exogenous nucleic acid can be inserted into a vector for transfer into a cell, tissue or organism. The nucleic acid can encode a polypeptide or protein or an antisense RNA, for example. The nucleic acid can be functionally linked to a promoter. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences.

The heterologous nucleic acid introduced into the cell can include, for example, one or more nucleic acids encoding one or more subparts of the receptor. For example, four different subparts of a $P2Y_{12}$ receptor could be encoded in four different nucleic acids or in three, two, or one nucleic acids. In various embodiments, specific antagonists can be tested using different subparts for the channel. These assays would thus identify antagonists for different subtypes of P2Y channels (e.g., $P2Y_{12}$, $P2Y_{13}$, or $P2Y_{14}$) that complex together to form the fully functional receptor channel present in native kidney cells. In a further aspect, antagonists of other members ADP-($P2Y_{12}$)-like receptor family can be screened by contacting a test compound with a cell that expresses a heterologous nucleic acid that encodes one the family members (e.g. $P2Y_{12}$, $P2Y_{13}$, $P2Y_{14}$, GPR34, GPR34-like, GPR82, GPR87, and GPR171).

A cell-line expressing a heterologous nucleic acid can be further engineered to provide optimized detection of intracellular calcium in response to the activity of the target receptor, e.g. $P2Y_{12}$. For example, the cell-line can co-express a promiscuous or chimeric G protein to couple the receptor to the calcium signaling pathway (e.g. see Pausch, M. H., et al., (2004) Biochem Biophys Res Commun. 324:171-7). Appropriate cell-lines are also commercially available, e.g. ChemiScreen™ Calcium-optimized stable cell-line expressing the human recombinant $P2Y_{12}$ receptor (Millipore Corporation, Billerica, Mass.).

Screening can take place in multi-well plates. Multi-well plates are standard in the art and come in a variety of sizes and shapes. For example, the multi-well plate can be 24, 48, or 96 well plates. Such screening assays can be automated or further modified for high throughput analysis. For high throughput screening, each well can include numerous test components. If a positive reaction is detected in a well, the screening is repeated with one of the test compounds contained in a single well.

Also provided are methods of screening for a $P2Y_{12}$ antagonist, further comprising screening for reversibility of response by removing the antagonist during the assay and testing PGE2 levels after the antagonist is removed. In one embodiment, the antagonist identified by the methods described herein is a reversible antagonist.

Optionally, the compound being screened can augment the effects of other compounds such as ATP, zinc, or ionomycin, for example. In this case, the compound being screened can be tested in the presence of another compound that stimulates the receptor. For example, the kidney cell can be in a solution containing an effective amount of ATP. An "effective amount of ATP" is defined as about 1 to about 500 mM of ATP or 10 to about 200 mM of ATP.

Glow luminescence assays have been readily adopted into high throughput screening facilities because of their intrinsically high sensitivities and long-lived signals. The signals for chemiluminescence systems such as luciferase and beta-galactosidase reporter genes or for alkaline phosphatase conjugates are often stable for several hours.

Several commercial luminescence and fluorescence detectors are available that can simultaneously inject liquid into single or multiple wells such as the WALLAC VICTOR2 (single well), MICROBETA RTM JET (six wells), or AURORA VIPR (eight wells). Typically, these instruments require 12 to 96 minutes to read a 96-well plate in flash luminescence or fluorescence mode (1 min/well). An alternative method is to inject the inhibitor/antagonist into all sample wells at the same time and measure the luminescence in the whole plate by imaging with a CCD camera, similar to the way that calcium responses are read by calcium-sensitive fluorescent dyes in the FLIPR or FLIPR-384 instruments. Other luminescence or fluorescence imaging systems include LEADSEEKER from AMERSHAM, the WALLAC VIEWLUX™ ultraHTS microplate imager, and the MOLECULAR DEVICES CLIPR imager.

PE BIOSYSTEMS TROPIX produces a CCD-based luminometer, the NORTHSTAR™ HTS Workstation. This instrument is able to rapidly dispense liquid into 96-well or 384-well microtiter plates by an external 8 or 16-head dispenser and then can quickly transfer the plate to a CCD camera that images the whole plate. The total time for dispensing liquid into a plate and transferring it into the reader is about 10 seconds.

Also contemplated are agents identified by the screening methods described herein, as well as methods of making those agents. An example of a method of making an agent includes identifying the agent using the methods provided herein, and manufacturing the agent or manufacturing the agent in a pharmaceutically acceptable carrier.

H. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In one aspect, the invention relates to a pharmaceutical composition comprising an effective amount of a lithium salt in combination with an effective amount of a second agent that is an ADP-($P2Y_{12}$)-like receptor modulator.

In a further aspect, the lithium salt of the pharmaceutical composition is lithium carbonate. In a still further aspect, the lithium salt of the pharmaceutical composition is lithium citrate. In a yet further aspect, the pharmaceutical composition is administered for the co-treatment of nephrogenic diabetes insipidus and a neurological or psychiatric disorder.

In a further aspect, the effective amount of the ADP-($P2Y_{12}$)-like receptor modulator of the pharmaceutical composition is a therapeutically effective amount to treat nephrogenic diabetes insipidus. In a still further aspect, the effective amount of the ADP-($P2Y_{12}$)-like receptor modulator of the pharmaceutical composition is a prophylactically effective amount to prevent nephrogenic diabetes insipidus. In a yet further aspect, the lithium salt and the ADP-($P2Y_{12}$)-like receptor modulator of the pharmaceutical composition are co-administered.

In a further aspect, the effective amount of the lithium salt of the pharmaceutical composition is a therapeutically effective amount to treat a neurological or psychiatric disorder. In a yet further aspect, the effective amount of the lithium salt of the pharmaceutical composition is a prophylactically effective amount to prevent a neurological or psychiatric disorder.

In a further aspect, the pharmaceutical composition is administered to a human diagnosed with a need for treatment of neurological or psychiatric disorder prior to the administering step. In a yet further aspect, the neurological disorder is selected from acute brain injury, migraine, chronic cluster headache, cluster headache syndrome, hypnic headache, trigeminal neuralgia, and chronic neurodegenerative disease. In a still further aspect, the acute brain injury is selected from stroke, ischemia reperfusion injury, diffuse cerebral hypoxia, focal cerebral ischemia, cerebral infarction, and global cerebral ischemia. In an even further aspect, the chronic neurodegenerative disorder is selected from Alzheimer's disease, Parkinson's disease, and Huntington's disease. In a still further aspect, the psychiatric disorder is selected from bipolar disorder, major depression, schizoaffective disorder, schizophrenic disorder, impulse control disorders, mixed bipolar disorder, hyperactivity with psychotic components, hyperactivity with neurotic components, hyperactivity with aggressive behavior, hyperactivity with aggressive outbursts, mania in bipolar disorder, prophylaxis for depression, prophylaxis for mania in bipolar disorder, and unipolar depression. In a yet further aspect, the psychiatric disorder is selected from bipolar disorder, major depression, schizoaffective disorder, schizophrenic disorder, and mixed bipolar disorder. In an even further aspect, the psychiatric disorder is bipolar disorder.

In a further aspect, the pharmaceutical composition is administered to a human diagnosed with a need for treatment of a disorder selected from neutropenia and anemia.

In a further aspect, the pharmaceutical composition is administered to a human diagnosed with a need for treatment of the nephrogenic diabetes insipidus prior to the administering step. In a still further aspect, the nephrogenic diabetes insipidus is acquired nephrogenic diabetes insipidus.

In a further aspect, the acquired nephrogenic diabetes insipidus is induced by administration of a therapeutic agent. In a still further aspect, the administration of the therapeutic agent precedes the administration of the pharmaceutical composition. In a yet further aspect, the therapeutic agent is selected from acetohexamide, an aminoglycoside, amphotericin B, bumetanide, clozapine, colchicine, a corticosteroid, demeclocycline, ethacrynic acid, foscarnet, furosemide, gentamicin, glyburide, ifosfamide, a lithium salt, mannitol, methoxyflurane, propoxyphene, tolazamide, torsemide, and vinblastine. In an even further aspect, the therapeutic agent is selected from clozapine, foscarnet, and a lithium salt. In a still further aspect, the therapeutic agent is a lithium salt. In a yet further aspect, the lithium salt is lithium carbonate. In an even further aspect, the lithium salt is lithium citrate. In a still further aspect, the therapeutic agent is a loop diuretic. In a yet further aspect, the loop diuretic is selected from torsemide, furosemide, bumetanide, and ethacrynic acid.

In a further aspect, the acquired nephrogenic diabetes insipidus is induced by a pathophysiological condition. In a still further aspect, the pathophysiological condition is selected from amyloidosis, analgesic nephropathy, chronic hypercalcemia, chronic kidney failure, hypokalemia, hypercalcemia, kidney disease, multiple myeloma, polycystic kidney disease, protein starvation, pyelonephritis, sarcoidosis, and sickle cell disease.

In a further aspect, the acquired nephrogenic diabetes insipidus is induced by a post-obstructive uropathy. In a still further aspect, the acquired nephrogenic diabetes insipidus is induced by pregnancy.

In a further aspect, the ADP-($P2Y_{12}$)-like receptor modulator of the pharmaceutical composition is a modulator of a receptor selected from $P2Y_{12}$, $P2Y_{13}$, $P2Y_{14}$, GPR34, GPR34-like, GPR82, GPR87, and GPR171. In a still further aspect, the ADP-($P2Y_{12}$)-like receptor modulator is a $P2Y_{12}$ modulator. In a yet further aspect, the $P2Y_{12}$ modulator is selected from clopidogrel, ticlopidine, prasugrel, ticagrelor, cangrelor, and elinogrel. In an even further aspect, the $P2Y_{12}$ modulator is selected from clopidogrel, prasugrel, and ticagrelor. In a still further aspect, the $P2Y_{12}$ modulator is clopidogrel. In a yet further aspect, the $P2Y_{12}$ modulator is prasugrel. In an even further aspect, the $P2Y_{12}$ modulator is ticagrelor.

In a further aspect, the ADP-($P2Y_{12}$)-like receptor modulator of the pharmaceutical composition is selected from an antagonist, a negative allosteric modulator, and an inverse agonist. In a still further aspect, the ADP-($P2Y_{12}$)-like receptor modulator is an antagonist. In a yet further aspect, the antagonist is selected from a thienopyridine, a cyclopentyltriazolopyrimidine, a nucleotide analog, and a nucleoside analog. In an even further aspect, the antagonist is a reversible antagonist. In a still further aspect, the antagonist is an irreversible antagonist.

In a further aspect, the antagonist is $P2Y_{12}$ antagonist. In a still further aspect, the $P2Y_{12}$ antagonist is selected from clopidogrel, ticlopidine, prasugrel, ticagrelor, cangrelor, and elinogrel. In a yet further aspect, the $P2Y_{12}$ antagonist is selected from clopidogrel, prasugrel, and ticagrelor. In an even further aspect, the $P2Y_{12}$ antagonist is clopidogrel. In a still further aspect, the $P2Y_{12}$ antagonist is prasugrel. In a yet further aspect, $P2Y_{12}$ antagonist is ticagrelor. In an even further aspect, the antagonist is a selective $P2Y_{12}$ antagonist.

In a further aspect, the ADP-($P2Y_{12}$)-like receptor modulator of the pharmaceutical composition is selected from clopidogrel, ticlopidine, prasugrel, ticagrelor, cangrelor, and elinogrel. In a still further aspect, the ADP-($P2Y_{12}$)-like receptor modulator is selected from clopidogrel, prasugrel, and ticagrelor. In a yet further aspect, the ADP-($P2Y_{12}$)-like receptor modulator is clopidogrel. In an even further aspect, the ADP-($P2Y_{12}$)-like receptor modulator is prasugrel. In a still further aspect, the ADP-($P2Y_{12}$)-like receptor modulator is ticagrelor.

In a further aspect, the pharmaceutical composition further comprises a $P2Y_2$ modulator.

In one aspect, the invention relates to a pharmaceutical composition comprising an effective amount of a lithium salt in combination with an effective amount of a second agent selected from clopidogrel, ticlopidine, prasugrel, ticagrelor, cangrelor, and elinogrel.

In a further aspect, lithium salt of the pharmaceutical composition is lithium carbonate. In a still further aspect, lithium salt of the pharmaceutical composition is lithium citrate.

In a further aspect, the second agent of the pharmaceutical composition is selected from clopidogrel, prasugrel, and ticagrelor. In a still further aspect, the second agent is clopidogrel. In a yet further aspect, the second agent is prasugrel. In an even further aspect, the second agent is ticagrelor.

In a further aspect, the pharmaceutical composition is administered for the co-treatment of nephrogenic diabetes insipidus and a neurological or psychiatric disorder. In a still further aspect, the effective amount of the second agent of the pharmaceutical composition is a therapeutically effective amount to treat nephrogenic diabetes insipidus. In a yet further aspect, the effective amount of the second agent of the pharmaceutical composition is a prophylactically effective amount to prevent nephrogenic diabetes insipidus.

In a further aspect, the effective amount of the lithium salt of the pharmaceutical composition is a therapeutically effective amount to treat a neurological or psychiatric disorder. In a still further aspect, the effective amount of the lithium salt of the pharmaceutical composition is a prophylactically effective amount to prevent a neurological or psychiatric disorder. In a yet further aspect, the lithium salt and the second agent of the pharmaceutical composition are co-administered.

In a further aspect, the pharmaceutical composition is administered to a human diagnosed with a need for treatment of neurological or psychiatric disorder prior to the administering step. In a still further aspect, the neurological disorder is selected from acute brain injury, migraine, chronic cluster headache, cluster headache syndrome, hypnic headache, trigeminal neuralgia, and chronic neurodegenerative disease. In a yet further aspect, the acute brain injury is selected from stroke, ischemia reperfusion injury, diffuse cerebral hypoxia, focal cerebral ischemia, cerebral infarction, and global cerebral ischemia. In an even further aspect, the chronic neurodegenerative disorder is selected from Alzheimer's disease, Parkinson's disease, and Huntington's disease. In a still further aspect, the psychiatric disorder is selected from bipolar disorder, major depression, schizoaffective disorder, schizophrenic disorder, impulse control disorders, mixed bipolar disorder, hyperactivity with psychotic components, hyperactivity with neurotic components, hyperactivity with aggressive behavior, hyperactivity with aggressive outbursts, mania in bipolar disorder, prophylaxis for depression, prophylaxis for mania in bipolar disorder, and unipolar depression. In a yet further aspect, the psychiatric disorder is selected from bipolar disorder, major depression, schizoaffective disorder, schizophrenic disorder, and mixed bipolar disorder. In an even further aspect, the psychiatric disorder is bipolar disorder.

In a further aspect, the pharmaceutical composition is administered to a human diagnosed with a need for treatment of a disorder selected from neutropenia and anemia. In a still further aspect, the pharmaceutical composition is administered to a human diagnosed with a need for treatment of neutropenia. In a yet further aspect, the pharmaceutical composition is administered to a human diagnosed with a need for treatment of anemia.

In a further aspect, the pharmaceutical composition is administered to a human diagnosed with a need for treatment of the nephrogenic diabetes insipidus prior to the administering step. In a still further aspect, the nephrogenic diabetes insipidus is acquired nephrogenic diabetes insipidus. In a yet further aspect, the acquired nephrogenic diabetes insipidus is induced by administration of a therapeutic agent. In an even further aspect, the administration of the therapeutic agent precedes the administration of the pharmaceutical composition. In a still further aspect, the therapeutic agent is selected from acetohexamide, an aminoglycoside, amphotericin B, bumetanide, clozapine, colchicine, a corticosteroid, demeclocycline, ethacrynic acid, foscarnet, furosemide, gentamicin, glyburide, ifosfamide, a lithium salt, mannitol, methoxyflurane, propoxyphene, tolazamide, torsemide, and vinblastine. In a yet further aspect, the therapeutic agent is selected from clozapine, foscarnet, and a lithium salt. In a still further aspect, the therapeutic agent is a lithium salt. In an even further aspect, the lithium salt is lithium carbonate. In a still further aspect, the lithium salt is lithium citrate. In a yet further aspect, the therapeutic agent is a loop diuretic. In an even further aspect, the loop diuretic is selected from torsemide, furosemide, bumetanide, and ethacrynic acid.

In a further aspect, the acquired nephrogenic diabetes insipidus is induced by a pathophysiological condition. In a still further aspect, the pathophysiological condition is selected from amyloidosis, analgesic nephropathy, chronic hypercalcemia, chronic kidney failure, hypokalemia, hypercalcemia, kidney disease, multiple myeloma, polycystic kidney disease, protein starvation, pyelonephritis, sarcoidosis, and sickle cell disease.

In a further aspect, the acquired nephrogenic diabetes insipidus is induced by a post-obstructive uropathy. In a still further aspect, the acquired nephrogenic diabetes insipidus is induced by pregnancy.

In a further aspect, the second agent of the pharmaceutical composition is a modulator of a receptor selected from $P2Y_{12}$, $P2Y_{13}$, $P2Y_{14}$, GPR34, GPR34-like, GPR82, GPR87, and GPR171. In a still further aspect, the second agent is a $P2Y_{12}$ modulator. In a yet further aspect, the second agent is an antagonist of a receptor selected from $P2Y_{12}$, $P2Y_{13}$, $P2Y_{14}$, GPR34, GPR34-like, GPR82, GPR87, and GPR171. In an even further aspect, the second agent is a $P2Y_{12}$ antagonist.

In a further aspect, the pharmaceutical composition further comprises a $P2Y_2$ modulator.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require modulation of ADP-($P2Y_{12}$)-like receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating ADP-$(P2Y_{12})$-like receptor activity (e.g., treatment of one or more diabetes insipidus disorders) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

I. METHODS OF USING THE COMPOUNDS AND COMPOSITIONS

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the disclosed compounds can be coadministered with a lithium salt. In a further aspect, the disclosed compounds can be coadministered with lithium carbonate. In a yet further aspect, the disclosed compounds can be coadministered with lithium citrate.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of diabetes insipidus disorders associated with an ADP-$(P2Y_{12})$-like receptor. Examples of disorders associated with ADP-$(P2Y_{12})$-like receptor dysfunction include nephrogenic diabetes insipidus and acquired nephrogenic diabetes insipidus. In a further aspect, the acquired nephrogenic diabetes is induced by prior treatment with a lithium salt. In a still further aspect, the acquired nephrogenic diabetes can be induced by treatment with a lithium salt.

Thus, provided is a method for treating or preventing acquired nephrogenic diabetes insipidus, comprising: administering to a subject at least one disclosed compound; at least one disclosed pharmaceutical composition; and/or at least one disclosed product in a dosage and amount effective to treat the disorder in the subject. In a further aspect, the subject has been administered a lithium salt prior to administration of at least one disclosed compound; at least one disclosed pharmaceutical composition; and/or at least one disclosed product. In a still further aspect, the subject has been co-administered a lithium salt with at least one disclosed compound; at least one disclosed pharmaceutical composition; and/or at least one disclosed product. In a yet further aspect, the subject administrated at least one disclosed compound; at least one disclosed pharmaceutical composition; and/or at least one disclosed product prophylactically to prevent onset of acquired nephrogenic diabetes insipidus.

a. Method for Treatment of Nephrogenic Diabetes (I)

In one aspect, the invention relates to a method for the treatment of nephrogenic diabetes insipidus in a mammal comprising the step of administering to the mammal an effective amount of an ADP-$(P2Y_{12})$-like receptor modulator, thereby treating nephrogenic diabetes insipidus in the mammal.

In a further aspect, the mammal is human. In a yet further aspect, the mammal has been diagnosed with a need for treatment of the nephrogenic diabetes insipidus prior to the administering step. In a still further aspect, the method further comprises the step of identifying a mammal in need of treatment of the nephrogenic diabetes insipidus.

In a further aspect, an effective amount is a therapeutically effective amount. In a still further aspect, an effective amount is a prophylactically effective amount.

In a further aspect, the method further comprises the step of administering a lithium salt. In a still further aspect, the lithium salt is lithium carbonate. In a yet further aspect, the lithium salt is lithium citrate.

In a further aspect, the lithium salt and the ADP-$(P2Y_{12})$-like receptor modulator are co-administered. In a still further aspect, the lithium salt is administered prior to administration of the ADP-$(P2Y_{12})$-like receptor modulator. In a yet further aspect, lithium salt is administered after administration of the ADP-$(P2Y_{12})$-like receptor modulator.

In a further aspect, the mammal has been diagnosed with a need for treatment of a neurological disorder. In a still further aspect, the method further comprises the step of identifying a mammal in need of treatment of a neurological disorder. In a yet further aspect, the neurological disorder is selected from acute brain injury, migraine, chronic cluster headache, cluster headache syndrome, hypnic headache, trigeminal neuralgia, and chronic neurodegenerative disease. In an even further aspect, the acute brain injury is selected from stroke, ischemia reperfusion injury, diffuse cerebral hypoxia, focal cerebral ischemia, cerebral infarction, and global cerebral ischemia. In a still further aspect, the chronic neurodegenerative disorder is selected from Alzheimer's disease, Parkinson's disease, and Huntington's disease. In an even further aspect, the mammal is administered a lithium salt to treat the neurological disorder.

In a further aspect, the mammal has been diagnosed with a need for treatment of a psychiatric disorder. In a still further aspect, the method further comprises the step of identifying a mammal in need of treatment of a psychiatric disorder. In a yet further aspect, the psychiatric disorder is selected from bipolar disorder, major depression, schizoaffective disorder, schizophrenic disorder, impulse control disorders, mixed bipolar disorder, hyperactivity with psychotic components, hyperactivity with neurotic components, hyperactivity with aggressive behavior, hyperactivity with aggressive outbursts, mania in bipolar disorder, prophylaxis for depression, prophylaxis for mania in bipolar disorder, and unipolar depression. In an even further aspect, the psychiatric disorder is selected from bipolar disorder, major depression, schizoaffective disorder, schizophrenic disorder, and mixed bipolar disorder. In a still further aspect, the psychiatric disorder is bipolar disorder. In a yet further aspect, the mammal is administered a lithium salt to treat the psychiatric disorder.

In a further aspect, the mammal has been diagnosed with a need for treatment of a disorder selected from neutropenia and anemia. In a still further aspect, the method further comprises the step of identifying a mammal in need of treatment of a disorder selected from neutropenia and anemia. In a yet further aspect, the mammal is administered a lithium salt to treat the neutropenia. In an even further aspect, the mammal is administered a lithium salt to treat the anemia.

In a further aspect, the nephrogenic diabetes insipidus is acquired nephrogenic diabetes insipidus. In a still further aspect, the acquired nephrogenic diabetes insipidus is induced by administration of a therapeutic agent. In a yet further aspect, the administration of the therapeutic agent precedes the administration of the ADP-(P2Y$_{12}$)-like receptor modulator. In an even further aspect, the therapeutic agent is selected from acetohexamide, an aminoglycoside, amphotericin B, bumetanide, clozapine, colchicine, a corticosteroid, demeclocycline, ethacrynic acid, foscarnet, furosemide, gentamicin, glyburide, ifosfamide, a lithium salt, mannitol, methoxyflurane, propoxyphene, tolazamide, torsemide, and vinblastine. In a still further aspect, the therapeutic agent is selected from clozapine, foscarnet, and a lithium salt. In a yet further aspect, the therapeutic agent is a lithium salt. In an even further aspect, the lithium salt is lithium carbonate. In a still further aspect, the therapeutic agent is a loop diuretic. In a yet further aspect, the loop diuretic is selected from torsemide, furosemide, bumetanide, and ethacrynic acid.

In a further aspect, the acquired nephrogenic diabetes insipidus is induced by a pathophysiological condition. In a still further aspect, the pathophysiological condition is selected from amyloidosis, analgesic nephropathy, chronic hypercalcemia, chronic kidney failure, hypokalemia, hypercalcemia, kidney disease, multiple myeloma, polycystic kidney disease, protein starvation, pyelonephritis, sarcoidosis, and sickle cell disease. In a yet further aspect, the acquired nephrogenic diabetes insipidus is induced by a post-obstructive uropathy.

In a further aspect, the acquired nephrogenic diabetes insipidus is induced by pregnancy. In a yet further aspect, the acquired nephrogenic diabetes insipidus is induced by a post-obstructive uropathy.

In a further aspect, the ADP-(P2Y$_{12}$)-like receptor modulator is a modulator of a receptor selected from P2Y$_{12}$, P2Y$_{13}$, P2Y$_{14}$, GPR34, GPR34-like, GPR82, GPR87, and GPR171. In a further aspect, the ADP-(P2Y$_{12}$)-like receptor modulator is selected from an antagonist, a negative allosteric modulator, and an inverse agonist. In a still further aspect, the ADP-(P2Y$_{12}$)-like receptor modulator is an antagonist. In a yet further aspect, the antagonist is selected from a thienopyridine, a cyclopentyltriazolopyrimidine, a nucleotide analog, and a nucleoside analog. In an even further aspect, the antagonist is a reversible antagonist. In a yet further aspect, the antagonist is an irreversible antagonist. In a still further aspect, the antagonist is P2Y$_{12}$ antagonist.

In a further aspect, the ADP-(P2Y$_{12}$)-like receptor modulator is selected from clopidogrel, ticlopidine, prasugrel, ticagrelor, cangrelor, and elinogrel. In a yet further aspect, the ADP-(P2Y$_{12}$)-like receptor modulator is selected from clopidogrel, prasugrel, and ticagrelor. In a still further aspect, the ADP-(P2Y$_{12}$)-like receptor modulator is clopidogrel. In an even further aspect, the ADP-(P2Y$_{12}$)-like receptor modulator is prasugrel. In a still further aspect, the ADP-(P2Y$_{12}$)-like receptor modulator is ticagrelor.

In a further aspect, the ADP-(P2Y$_{12}$)-like receptor modulator is a P2Y$_{12}$ modulator. In an even further aspect, the P2Y$_{12}$ modulator is selected from clopidogrel, ticlopidine, prasugrel, ticagrelor, cangrelor, and elinogrel. In a yet further aspect, P2Y$_{12}$ modulator is selected from clopidogrel, prasugrel, and ticagrelor. In a still further aspect, the P2Y$_{12}$ modulator is clopidogrel. In an even further aspect, the P2Y$_{12}$ modulator is prasugrel. In a still further aspect, P2Y$_{12}$ modulator is ticagrelor.

In a further aspect, the ADP-(P2Y$_{12}$)-like receptor antagonist is selected from clopidogrel, ticlopidine, prasugrel, ticagrelor, cangrelor, and elinogrel. In a still further aspect, the ADP-(P2Y$_{12}$)-like receptor antagonist is selected from clopidogrel, prasugrel, and ticagrelor. In a yet further aspect, the ADP-(P2Y$_{12}$)-like receptor antagonist is clopidogrel. In an even further aspect, the ADP-(P2Y$_{12}$)-like receptor antagonist is prasugrel. In a yet further aspect, the ADP-(P2Y$_{12}$)-like receptor antagonist is ticagrelor.

In a further aspect, the P2Y$_{12}$ antagonist is selected from clopidogrel, ticlopidine, prasugrel, ticagrelor, cangrelor, and elinogrel. In a still further aspect, the P2Y$_{12}$ antagonist is selected from clopidogrel, prasugrel, and ticagrelor. In a yet further aspect, the P2Y$_{12}$ antagonist is clopidogrel. In an even further aspect, the P2Y$_{12}$ antagonist is prasugrel. In a yet further aspect, the P2Y$_{12}$ antagonist is ticagrelor. In a still further aspect, the antagonist is a selective P2Y$_{12}$ antagonist.

In a further aspect, the method further comprises co-administration of a P2Y$_2$ modulator with the ADP-(P2Y$_{12}$)-like receptor modulator. In a still further aspect, the ADP-(P2Y$_{12}$)-like receptor modulator is a P2Y$_{12}$ modulator. In a yet further aspect, the ADP-(P2Y$_{12}$)-like receptor modulator is a selective P2Y$_{12}$ modulator.

b. Method for Treatment of Nephrogenic Diabetes (II)

In one aspect, the invention relates to a method for the treatment of nephrogenic diabetes insipidus in a mammal comprising the step of administering to the mammal an effective amount of a compound selected from clopidogrel, ticlopidine, prasugrel, ticagrelor, cangrelor, and elinogrel.

In a further aspect, the mammal of the method is a human. In a yet further aspect, the mammal of the method has been diagnosed with a need for treatment of the nephrogenic diabetes insipidus prior to the administering step.

In a further aspect, the method further comprises the step of identifying a mammal in need of treatment of the nephrogenic diabetes insipidus. In a further aspect, the effective amount of the method is a therapeutically effective amount. In a still further aspect, the effective amount of the method is a prophylactically effective amount.

In a further aspect, the method further comprises the step of administering a lithium salt. In a still further aspect, the lithium salt is lithium carbonate. In a yet further aspect, the lithium salt is lithium citrate. In an even further aspect, the lithium salt and the compound are co-administered. In a still further aspect, the lithium salt is administered prior to administration of the compound. In a yet further aspect, the lithium salt is administered after administration of the compound.

In a further aspect, the mammal of the method has been diagnosed with a need for treatment of a neurological disorder. In a still further aspect, the method further comprises the step of identifying a mammal in need of treatment of a neurological disorder. In a yet further aspect, the neurological disorder is selected from acute brain injury, migraine, chronic cluster headache, cluster headache syndrome, hypnic headache, trigeminal neuralgia, and chronic neurodegenerative disease. In an even further aspect, the acute brain injury is selected from stroke, ischemia reperfusion injury, diffuse cerebral hypoxia, focal cerebral ischemia, cerebral infarction, and global cerebral ischemia. In a still further aspect, the chronic neurodegenerative disorder is selected from Alzheimer's disease, Parkinson's disease, and Huntington's disease. In a yet further aspect, the mammal is administered a lithium salt to treat the neurological disorder. In an even further aspect, the lithium salt administered to treat the neurological disorder is lithium carbonate. In a still further aspect, the lithium salt administered to treat the neurological disorder is lithium citrate.

In a further aspect, the mammal of the method has been diagnosed with a need for treatment of a psychiatric disorder. In a still further aspect, the method further comprises the step of identifying a mammal in need of treatment of a psychiatric disorder. In a yet further aspect, the psychiatric disorder is selected from bipolar disorder, major depression, schizoaffective disorder, schizophrenic disorder, impulse control disorders, mixed bipolar disorder, hyperactivity with psychotic components, hyperactivity with neurotic components, hyperactivity with aggressive behavior, hyperactivity with aggressive outbursts, mania in bipolar disorder, prophylaxis for depression, prophylaxis for mania in bipolar disorder, and unipolar depression. In an even further aspect, the psychiatric disorder is selected from bipolar disorder, major depression, schizoaffective disorder, schizophrenic disorder, and mixed bipolar disorder. In a still further aspect, the psychiatric disorder is bipolar disorder. In a yet further aspect, the mammal is administered a lithium salt to treat the psychiatric disorder. In an even further aspect, the lithium salt administered to treat the psychiatric disorder is lithium carbonate. In a still further aspect, the lithium salt administered to treat the psychiatric disorder is lithium citrate.

In a further aspect, the mammal of the method has been diagnosed with a need for treatment of a disorder selected from neutropenia and anemia. In a still further aspect, the mammal of the method has been diagnosed with a need for treatment of neutropenia. In a yet further aspect, the mammal of the method has been diagnosed with a need for treatment of anemia. In an even further aspect, the method further comprises the step of identifying a mammal in need of treatment of a disorder selected from neutropenia and anemia. In a still further aspect, the method further comprises the step of identifying a mammal in need of treatment of neutropenia. In a yet further aspect, the method further comprises the step of identifying a mammal in need of treatment of anemia. In an even further aspect, the mammal is administered a lithium salt to treat a disorder selected from neutropenia and anemia. In a still further aspect, the lithium salt administered to treat a disorder selected from neutropenia and anemia is lithium carbonate. In a yet further aspect, the lithium salt administered to treat a disorder selected from neutropenia and anemia is lithium citrate.

In a further aspect, the nephrogenic diabetes insipidus of the method is acquired nephrogenic diabetes insipidus. In a still further aspect, the acquired nephrogenic diabetes insipidus is induced by administration of a therapeutic agent. In a yet further aspect, the administration of the therapeutic agent precedes the administration of the compound. In an even further aspect, the therapeutic agent is selected from acetohexamide, an aminoglycoside, amphotericin B, bumetanide, clozapine, colchicine, a corticosteroid, demeclocycline, ethacrynic acid, foscarnet, furosemide, gentamicin, glyburide, ifosfamide, a lithium salt, mannitol, methoxyflurane, propoxyphene, tolazamide, torsemide, and vinblastine. In a still further aspect, the therapeutic agent is selected from clozapine, foscarnet, and a lithium salt. In a yet further aspect, the therapeutic agent that induces the acquired nephrogenic diabetes insipidus is a lithium salt. In an even further aspect, the therapeutic agent is lithium carbonate. In a still further aspect, the therapeutic agent is lithium citrate. In a yet further aspect, the therapeutic agent that induces the acquired nephrogenic diabetes insipidus is a loop diuretic. In an even further aspect, the loop diuretic is selected from torsemide, furosemide, bumetanide, and ethacrynic acid.

In a further aspect, the acquired nephrogenic diabetes insipidus is induced by a pathophysiological condition. In a still further aspect, the pathophysiological condition that induces the acquired nephrogenic diabetes insipidus is selected from amyloidosis, analgesic nephropathy, chronic hypercalcemia, chronic kidney failure, hypokalemia, hypercalcemia, kidney disease, multiple myeloma, polycystic kidney disease, protein starvation, pyelonephritis, sarcoidosis, and sickle cell disease.

In a further aspect, the acquired nephrogenic diabetes insipidus is induced by a post-obstructive uropathy. In a still further aspect, the acquired nephrogenic diabetes insipidus is induced by pregnancy.

In a further aspect, the compound compound of the method is a modulator of a receptor selected from $P2Y_{12}$, $P2Y_{13}$, $P2Y_{14}$, GPR34, GPR34-like, GPR82, GPR87, and GPR171. In a still further aspect, the compound is a $P2Y_{12}$ modulator. In a yet further aspect, the $P2Y_{12}$ modulator is an antagonist.

In a further aspect, the compound is selected from clopidogrel, prasugrel, and ticagrelor. In a still further aspect, the compound is clopidogrel. In a yet further aspect, the compound is prasugrel. In an even further aspect, the compound is ticagrelor.

In a further aspect, the method further comprises co-administration of a $P2Y_2$ modulator with the compound.

c. Method for Co-Treatment of Nephrogenic Diabetes Insipidus and a Neurological or Psychiatric Disorder (I)

In one aspect, the invention relates to a method of co-treatment of nephrogenic diabetes insipidus and a neurological or psychiatric disorder comprising the step of co-administering to the mammal an effective amount of an ADP-($P2Y_{12}$)-like receptor modulator and an effective amount of a lithium salt, thereby treating, respectively, the nephrogenic diabetes insipidus and the neurological or psychiatric disorder.

In a further aspect, the mammal of the method is a human. In a still further aspect, the mammal has been diagnosed with a need for treatment of nephrogenic diabetes insipidus prior to the administering step. In a yet further aspect, the method further comprises the step of identifying a mammal in need of treatment of nephrogenic diabetes insipidus.

In a further aspect, the effective amount of the ADP-(P2Y$_{12}$)-like receptor modulator of the method is a therapeutically effective amount. In a still further aspect, the effective amount of the ADP-(P2Y$_{12}$)-like receptor modulator of the method is a prophylactically effective amount.

In a further aspect, the effective amount of the lithium salt of the method is a therapeutically effective amount. In a still further aspect, the effective amount of the lithium salt of the method is a prophylactically effective amount. In a yet further aspect, the lithium salt of the method is lithium carbonate. In an even further aspect, the lithium salt of the method is lithium citrate.

In a further aspect, the co-administration of the method comprises administration of the lithium salt prior to administration of the ADP-(P2Y$_{12}$)-like receptor modulator. In a still further aspect, the co-administration of the method comprises administration of the lithium salt after administration of the ADP-(P2Y$_{12}$)-like receptor modulator.

In a further aspect, the mammal of the method has been diagnosed with a need for treatment of a neurological disorder. In a yet further aspect, the method further comprises the step of identifying a mammal in need of treatment of a neurological disorder. In a still further aspect, the neurological disorder is selected from acute brain injury, migraine, chronic cluster headache, cluster headache syndrome, hypnic headache, trigeminal neuralgia, and chronic neurodegenerative disease. In an even further aspect, the acute brain injury is selected from stroke, ischemia reperfusion injury, diffuse cerebral hypoxia, focal cerebral ischemia, cerebral infarction, and global cerebral ischemia. In a still further aspect, the chronic neurodegenerative disorder is selected from Alzheimer's disease, Parkinson's disease, and Huntington's disease.

In a further aspect, the mammal has been diagnosed with a need for treatment of a psychiatric disorder. In a still further aspect, the method further comprises the step of identifying a mammal in need of treatment of a psychiatric disorder. In a yet further aspect, the psychiatric disorder is selected from bipolar disorder, major depression, schizoaffective disorder, schizophrenic disorder, impulse control disorders, mixed bipolar disorder, hyperactivity with psychotic components, hyperactivity with neurotic components, hyperactivity with aggressive behavior, hyperactivity with aggressive outbursts, mania in bipolar disorder, prophylaxis for depression, prophylaxis for mania in bipolar disorder, and unipolar depression. In an even further aspect, the psychiatric disorder is selected from bipolar disorder, major depression, schizoaffective disorder, schizophrenic disorder, and mixed bipolar disorder. In a still further aspect, the psychiatric disorder is bipolar disorder.

In a further aspect, the nephrogenic diabetes insipidus of the method is acquired nephrogenic diabetes insipidus. In a still further aspect, the acquired nephrogenic diabetes insipidus is induced by administration of a therapeutic agent. In a yet further aspect, the administration of the therapeutic agent precedes the administration of the ADP-(P2Y$_{12}$)-like receptor modulator. In an even further aspect, the therapeutic agent is selected from acetohexamide, an aminoglycoside, amphotericin B, bumetanide, clozapine, colchicine, a corticosteroid, demeclocycline, ethacrynic acid, foscarnet, furosemide, gentamicin, glyburide, ifosfamide, a lithium salt, mannitol, methoxyflurane, propoxyphene, tolazamide, torsemide, and vinblastine. In a still further aspect, the therapeutic agent is selected from clozapine, foscarnet, and a lithium salt.

In a further aspect, the therapeutic agent that induces the acquired nephrogenic diabetes insipidus is a lithium salt. In a still further aspect, the lithium salt is lithium carbonate. In a yet further aspect, the lithium salt is lithium citrate.

In a further aspect, the therapeutic agent that induces the acquired nephrogenic diabetes insipidus is a loop diuretic. In a still further aspect, the loop diuretic is selected from torsemide, furosemide, bumetanide, and ethacrynic acid.

In a further aspect, the acquired nephrogenic diabetes insipidus is induced by a pathophysiological condition. In a still further aspect, the pathophysiological condition is selected from amyloidosis, analgesic nephropathy, chronic hypercalcemia, chronic kidney failure, hypokalemia, hypercalcemia, kidney disease, multiple myeloma, polycystic kidney disease, protein starvation, pyelonephritis, sarcoidosis, and sickle cell disease.

In a further aspect, the acquired nephrogenic diabetes insipidus is induced by a post-obstructive uropathy. In a still further aspect, the acquired nephrogenic diabetes insipidus is induced by pregnancy.

In a further aspect, the ADP-(P2Y$_{12}$)-like receptor modulator of the method is a modulator of a receptor selected from P2Y$_{12}$, P2Y$_{13}$, P2Y$_{14}$, GPR34, GPR34-like, GPR82, GPR87, and GPR171.

In a further aspect, the ADP-(P2Y$_{12}$)-like receptor modulator of the method is selected from an antagonist, a negative allosteric modulator, and an inverse agonist. In a still further aspect, the ADP-(P2Y$_{12}$)-like receptor modulator is an antagonist. In a yet further aspect, the antagonist is selected from a thienopyridine, a cyclopentyltriazolopyrimidine, a nucleotide analog, and a nucleoside analog. In an even further aspect, the antagonist is a reversible antagonist. In a still further aspect, the antagonist is an irreversible antagonist. In a still further aspect, wherein the antagonist is a selective P2Y$_{12}$ antagonist.

In a further aspect, the ADP-(P2Y$_{12}$)-like receptor modulator of the method is selected from clopidogrel, ticlopidine, prasugrel, ticagrelor, cangrelor, and elinogrel. In a still further aspect, the ADP-(P2Y$_{12}$)-like receptor modulator is selected from clopidogrel, prasugrel, and ticagrelor. In a yet further aspect, the ADP-(P2Y$_{12}$)-like receptor modulator is clopidogrel. In an even further aspect, the ADP-(P2Y$_{12}$)-like receptor modulator is prasugrel. In a still further aspect, the ADP-(P2Y$_{12}$)-like receptor modulator is ticagrelor.

In a further aspect, the ADP-(P2Y$_{12}$)-like receptor modulator of the method is a P2Y$_{12}$ modulator. In a still further aspect, the P2Y$_{12}$ modulator is selected from clopidogrel, ticlopidine, prasugrel, ticagrelor, cangrelor, and elinogrel. In an even further aspect, the P2Y$_{12}$ modulator is selected from clopidogrel, prasugrel, and ticagrelor. In a still further aspect, the P2Y$_{12}$ modulator is clopidogrel. In a yet further aspect, P2Y$_{12}$ modulator is prasugrel. In an even further aspect, the P2Y$_{12}$ modulator is ticagrelor.

In a further aspect, the ADP-(P2Y$_{12}$)-like receptor modulator of the method is a P2Y$_{12}$ antagonist. In a still further aspect, the P2Y$_{12}$ antagonist is selected from clopidogrel, ticlopidine, prasugrel, ticagrelor, cangrelor, and elinogrel. In a yet further aspect, the P2Y$_{12}$ antagonist is selected from clopidogrel, prasugrel, and ticagrelor. In an even further aspect, the P2Y$_{12}$ antagonist is clopidogrel. In a still further aspect, the P2Y$_{12}$ antagonist is prasugrel. In a yet further aspect, the P2Y$_{12}$ antagonist is ticagrelor.

In a further aspect, the method further comprises co-administration of a P2Y$_2$ modulator.

d. Method for Co-Treatment of Nephrogenic Diabetes Insipidus and a Neurological or Psychiatric Disorder (II)

In one aspect, the invention relates to a method of co-treatment of nephrogenic diabetes insipidus and a neurological or psychiatric disorder comprising the step of co-administering to the mammal an effective amount of a lithium salt and an effective amount of a compound selected from clopidogrel, ticlopidine, prasugrel, ticagrelor, cangrelor, and elinogrel, thereby treating, respectively, the neurological or psychiatric disorder and the nephrogenic diabetes insipidus.

In a further aspect, the mammal of the method is a human. In a still further aspect, the mammal has been diagnosed with a need for treatment of nephrogenic diabetes insipidus prior to the administering step. In a yet further aspect, the method further comprises the step of identifying a mammal in need of treatment of nephrogenic diabetes insipidus.

In a further aspect, the effective amount of the compound of the method is a therapeutically effective amount. In a still further aspect, the effective amount of compound of the method is a prophylactically effective amount.

In a further aspect, the effective amount of the lithium salt of the method is a therapeutically effective amount. In a still further aspect, the effective amount of the lithium salt of the method is a prophylactically effective amount. In a yet further aspect, the lithium salt of the method is lithium carbonate. In an even further aspect, the lithium salt of the method is lithium citrate.

In a further aspect, the co-treatment of the method comprises administration of the lithium salt prior to administration of the compound. In a still further aspect, the co-treatment of the method comprises administration of the lithium salt after administration of the compound.

In a further aspect, the mammal of the method has been diagnosed with a need for treatment of a neurological disorder. In a yet further aspect, the method further comprises the step of identifying a mammal in need of treatment of a neurological disorder. In a still further aspect, the neurological disorder is selected from acute brain injury, migraine, chronic cluster headache, cluster headache syndrome, hypnic headache, trigeminal neuralgia, and chronic neurodegenerative disease. In an even further aspect, the acute brain injury is selected from stroke, ischemia reperfusion injury, diffuse cerebral hypoxia, focal cerebral ischemia, cerebral infarction, and global cerebral ischemia. In a still further aspect, the chronic neurodegenerative disorder is selected from Alzheimer's disease, Parkinson's disease, and Huntington's disease.

In a further aspect, the mammal has been diagnosed with a need for treatment of a psychiatric disorder. In a still further aspect, the method further comprises the step of identifying a mammal in need of treatment of a psychiatric disorder. In a yet further aspect, the psychiatric disorder is selected from bipolar disorder, major depression, schizoaffective disorder, schizophrenic disorder, impulse control disorders, mixed bipolar disorder, hyperactivity with psychotic components, hyperactivity with neurotic components, hyperactivity with aggressive behavior, hyperactivity with aggressive outbursts, mania in bipolar disorder, prophylaxis for depression, prophylaxis for mania in bipolar disorder, and unipolar depression. In an even further aspect, the psychiatric disorder is selected from bipolar disorder, major depression, schizoaffective disorder, schizophrenic disorder, and mixed bipolar disorder. In a still further aspect, the psychiatric disorder is bipolar disorder.

In a further aspect, the nephrogenic diabetes insipidus of the method is acquired nephrogenic diabetes insipidus. In a still further aspect, the acquired nephrogenic diabetes insipidus is induced by administration of a therapeutic agent. In a yet further aspect, the administration of the therapeutic agent precedes the administration of the compound. In an even further aspect, the therapeutic agent is selected from acetohexamide, an aminoglycoside, amphotericin B, bumetanide, clozapine, colchicine, a corticosteroid, demeclocycline, ethacrynic acid, foscarnet, furosemide, gentamicin, glyburide, ifosfamide, a lithium salt, mannitol, methoxyflurane, propoxyphene, tolazamide, torsemide, and vinblastine. In a still further aspect, the therapeutic agent is selected from clozapine, foscarnet, and a lithium salt.

In a further aspect, the therapeutic agent that induces the acquired nephrogenic diabetes insipidus is a lithium salt. In a still further aspect, the lithium salt is lithium carbonate. In a yet further aspect, the lithium salt is lithium citrate.

In a further aspect, the therapeutic agent that induces the acquired nephrogenic diabetes insipidus is a loop diuretic. In a still further aspect, the loop diuretic is selected from torsemide, furosemide, bumetanide, and ethacrynic acid.

In a further aspect, the acquired nephrogenic diabetes insipidus is induced by a pathophysiological condition. In a still further aspect, the pathophysiological condition is selected from amyloidosis, analgesic nephropathy, chronic hypercalcemia, chronic kidney failure, hypokalemia, hypercalcemia, kidney disease, multiple myeloma, polycystic kidney disease, protein starvation, pyelonephritis, sarcoidosis, and sickle cell disease.

In a further aspect, the acquired nephrogenic diabetes insipidus is induced by a post-obstructive uropathy. In a still further aspect, the acquired nephrogenic diabetes insipidus is induced by pregnancy.

In a further aspect, the compound of the method is a modulator of a receptor selected from $P2Y_{12}$, $P2Y_{13}$, $P2Y_{14}$, GPR34, GPR34-like, GPR82, GPR87, and GPR171. In a still further aspect, the compound is a $P2Y_{12}$ modulator.

In a further aspect, the compound is selected from clopidogrel, prasugrel, and ticagrelor. In a still further aspect, the compound is clopidogrel. In a yet further aspect, the compound is prasugrel. In an even further aspect, the compound is ticagrelor.

In a further aspect, the method further comprises co-administration of a $P2Y_2$ modulator.

e. Method of Treating Nephrogenic Diabetes in a Mammal Administered a Lithium Salt (I)

In one aspect, the invention relates to a method of treating nephrogenic diabetes insipidus comprising the step of administering an effective amount of an ADP-(P2Y12)-like receptor modulator to a mammal that is administered a lithium salt, thereby treating the nephrogenic diabetes insipidus.

In a further aspect, the mammal is human. In a yet further aspect, the mammal has been diagnosed with a need for treatment of the nephrogenic diabetes insipidus prior to the administering step. In a still further aspect, the method further comprises the step of identifying a mammal in need of treatment of the nephrogenic diabetes insipidus.

In a further aspect, an effective amount of an ADP-(P2Y12)-like receptor modulator of the method is a therapeutically effective amount. In a still further aspect, an effective amount of an ADP-(P2Y12)-like receptor modulator of the method is a prophylactically effective amount.

In a further aspect, the lithium salt of the method is lithium carbonate. In a yet further aspect, the lithium salt of the method is lithium citrate. In a still further aspect, an effective amount of the lithium salt of the method is a therapeutically effective amount. In an even further aspect, an effective amount of the lithium salt of the method is a prophylactically effective amount.

In a further aspect, the lithium salt and the ADP-($P2Y_{12}$)-like receptor modulator are co-administered. In a still further aspect, the lithium salt is administered prior to administration of the ADP-($P2Y_{12}$)-like receptor modulator. In a yet further aspect, lithium salt is administered after administration of the ADP-($P2Y_{12}$)-like receptor modulator.

In a further aspect, the mammal has been diagnosed with a need for treatment of a neurological disorder. In a still further aspect, the method further comprises the step of identifying a mammal in need of treatment of a neurological disorder. In a yet further aspect, the neurological disorder is selected from acute brain injury, migraine, chronic cluster headache, cluster headache syndrome, hypnic headache, trigeminal neuralgia, and chronic neurodegenerative disease. In an even further aspect, the acute brain injury is selected from stroke, ischemia reperfusion injury, diffuse cerebral hypoxia, focal cerebral ischemia, cerebral infarction, and global cerebral ischemia. In a still further aspect, the chronic neurodegenerative disorder is selected from Alzheimer's disease, Parkinson's disease, and Huntington's disease. In an even further aspect, the mammal is administered a lithium salt to treat the neurological disorder.

In a further aspect, the mammal has been diagnosed with a need for treatment of a psychiatric disorder. In a still further aspect, the method further comprises the step of identifying a mammal in need of treatment of a psychiatric disorder. In a yet further aspect, the psychiatric disorder is selected from bipolar disorder, major depression, schizoaffective disorder, schizophrenic disorder, impulse control disorders, mixed bipolar disorder, hyperactivity with psychotic components, hyperactivity with neurotic components, hyperactivity with aggressive behavior, hyperactivity with aggressive outbursts, mania in bipolar disorder, prophylaxis for depression, prophylaxis for mania in bipolar disorder, and unipolar depression. In an even further aspect, the psychiatric disorder is selected from bipolar disorder, major depression, schizoaffective disorder, schizophrenic disorder, and mixed bipolar disorder. In a still further aspect, the psychiatric disorder is bipolar disorder. In a yet further aspect, the mammal is administered a lithium salt to treat the psychiatric disorder.

In a further aspect, the mammal has been diagnosed with a need for treatment of a disorder selected from neutropenia and anemia. In a still further aspect, the method further comprises the step of identifying a mammal in need of treatment of a disorder selected from neutropenia and anemia. In a yet further aspect, the mammal is administered a lithium salt to treat the neutropenia. In an even further aspect, the mammal is administered a lithium salt to treat the anemia.

In a further aspect, the nephrogenic diabetes insipidus is acquired nephrogenic diabetes insipidus. In a still further aspect, the acquired nephrogenic diabetes insipidus is induced by administration of a therapeutic agent. In a yet further aspect, the administration of the therapeutic agent precedes the administration of the ADP-($P2Y_{12}$)-like receptor modulator. In an even further aspect, the therapeutic agent is selected from acetohexamide, an aminoglycoside, amphotericin B, bumetanide, clozapine, colchicine, a corticosteroid, demeclocycline, ethacrynic acid, foscarnet, furosemide, gentamicin, glyburide, ifosfamide, a lithium salt, mannitol, methoxyflurane, propoxyphene, tolazamide, torsemide, and vinblastine. In a still further aspect, the therapeutic agent is selected from clozapine, foscarnet, and a lithium salt. In a yet further aspect, the therapeutic agent is a lithium salt. In an even further aspect, the lithium salt is lithium carbonate. In a still further aspect, the therapeutic agent is a loop diuretic. In a yet further aspect, the loop diuretic is selected from torsemide, furosemide, bumetanide, and ethacrynic acid.

In a further aspect, the acquired nephrogenic diabetes insipidus is induced by a pathophysiological condition. In a still further aspect, the pathophysiological condition is selected from amyloidosis, analgesic nephropathy, chronic hypercalcemia, chronic kidney failure, hypokalemia, hypercalcemia, kidney disease, multiple myeloma, polycystic kidney disease, protein starvation, pyelonephritis, sarcoidosis, and sickle cell disease. In a yet further aspect, the acquired nephrogenic diabetes insipidus is induced by a post-obstructive uropathy.

In a further aspect, the acquired nephrogenic diabetes insipidus is induced by pregnancy. In a yet further aspect, the acquired nephrogenic diabetes insipidus is induced by a post-obstructive uropathy.

In a further aspect, the ADP-($P2Y_{12}$)-like receptor modulator is a modulator of a receptor selected from $P2Y_{12}$, $P2Y_{13}$, $P2Y_{14}$, GPR34, GPR34-like, GPR82, GPR87, and GPR171. In a further aspect, the ADP-($P2Y_{12}$)-like receptor modulator is selected from an antagonist, a negative allosteric modulator, and an inverse agonist. In a still further aspect, the ADP-($P2Y_{12}$)-like receptor modulator is an antagonist. In a yet further aspect, the antagonist is selected from a thienopyridine, a cyclopentyltriazolopyrimidine, a nucleotide analog, and a nucleoside analog. In an even further aspect, the antagonist is a reversible antagonist. In a yet further aspect, the antagonist is an irreversible antagonist. In a still further aspect, the antagonist is $P2Y_{12}$ antagonist.

In a further aspect, the ADP-($P2Y_{12}$)-like receptor modulator is selected from clopidogrel, ticlopidine, prasugrel, ticagrelor, cangrelor, and elinogrel. In a yet further aspect, the ADP-($P2Y_{12}$)-like receptor modulator is selected from clopidogrel, prasugrel, and ticagrelor. In a still further aspect, the ADP-($P2Y_{12}$)-like receptor modulator is clopidogrel. In an even further aspect, the ADP-($P2Y_{12}$)-like receptor modulator is prasugrel. In a still further aspect, the ADP-($P2Y_{12}$)-like receptor modulator is ticagrelor.

In a further aspect, the ADP-($P2Y_{12}$)-like receptor modulator is a $P2Y_{12}$ modulator. In an even further aspect, the $P2Y_{12}$ modulator is selected from clopidogrel, ticlopidine, prasugrel, ticagrelor, cangrelor, and elinogrel. In a yet further aspect, $P2Y_{12}$ modulator is selected from clopidogrel, prasugrel, and ticagrelor. In a still further aspect, the $P2Y_{12}$ modulator is clopidogrel. In an even further aspect, the $P2Y_{12}$ modulator is prasugrel. In a still further aspect, $P2Y_{12}$ modulator is ticagrelor.

In a further aspect, the ADP-($P2Y_{12}$)-like receptor antagonist is selected from clopidogrel, ticlopidine, prasugrel, ticagrelor, cangrelor, and elinogrel. In a still further aspect, the ADP-($P2Y_{12}$)-like receptor antagonist is selected from clopidogrel, prasugrel, and ticagrelor. In a yet further aspect, the ADP-($P2Y_{12}$)-like receptor antagonist is clopidogrel. In an even further aspect, the ADP-($P2Y_{12}$)-like receptor antagonist is prasugrel. In a yet further aspect, the ADP-($P2Y_{12}$)-like receptor antagonist is ticagrelor.

In a further aspect, the $P2Y_{12}$ antagonist is selected from clopidogrel, ticlopidine, prasugrel, ticagrelor, cangrelor, and elinogrel. In a still further aspect, the $P2Y_{12}$ antagonist is selected from clopidogrel, prasugrel, and ticagrelor. In a yet further aspect, the $P2Y_{12}$ antagonist is clopidogrel. In an even further aspect, the $P2Y_{12}$ antagonist is prasugrel. In a yet further aspect, the P2Y$_{12}$ antagonist is ticagrelor. In a still further aspect, the antagonist is a selective P2Y$_{12}$ antagonist.

In a further aspect, the method further comprises co-administration of a P2Y$_2$ modulator with the ADP-(P2Y$_{12}$)-like receptor modulator. In a still further aspect, the ADP-(P2Y$_{12}$)-like receptor modulator is a P2Y$_{12}$ modulator. In a yet further aspect, the ADP-(P2Y$_{12}$)-like receptor modulator is a selective P2Y$_{12}$ modulator.

f. Method of Treating Nephrogenic Diabetes in a Mammal Administered a Lithium Salt (II)

In one aspect, the invention relates to a method of treating nephrogenic diabetes insipidus comprising the step of administering an effective amount of a compound selected from clopidogrel, ticlopidine, prasugrel, ticagrelor, cangrelor, and elinogrel to a mammal that is administered a lithium salt, thereby treating the nephrogenic diabetes insipidus.

In a further aspect, the mammal of the method is a human. In a yet further aspect, the mammal of the method has been diagnosed with a need for treatment of the nephrogenic diabetes insipidus prior to the administering step.

In a further aspect, the method further comprises the step of identifying a mammal in need of treatment of the nephrogenic diabetes insipidus. In a further aspect, the effective amount of the compound of the method is a therapeutically effective amount. In a still further aspect, the effective amount of the compound of the method is a prophylactically effective amount.

In a further aspect, the lithium salt of the method is lithium carbonate. In a yet further aspect, the lithium salt is lithium citrate. In an even further aspect, the lithium salt and the compound of the method are co-administered. In a still further aspect, the lithium salt is administered prior to administration of the compound. In a yet further aspect, the lithium salt is administered after administration of the compound. In a still further aspect, an effective amount of the lithium salt of the method is a therapeutically effective amount. In an even further aspect, an effective amount of the lithium salt of the method is a prophylactically effective amount.

In a further aspect, the mammal of the method has been diagnosed with a need for treatment of a neurological disorder. In a still further aspect, the method further comprises the step of identifying a mammal in need of treatment of a neurological disorder. In a yet further aspect, the neurological disorder is selected from acute brain injury, migraine, chronic cluster headache, cluster headache syndrome, hypnic headache, trigeminal neuralgia, and chronic neurodegenerative disease. In an even further aspect, the acute brain injury is selected from stroke, ischemia reperfusion injury, diffuse cerebral hypoxia, focal cerebral ischemia, cerebral infarction, and global cerebral ischemia. In a still further aspect, the chronic neurodegenerative disorder is selected from Alzheimer's disease, Parkinson's disease, and Huntington's disease. In a yet further aspect, the mammal is administered a lithium salt to treat the neurological disorder. In an even further aspect, the lithium salt administered to treat the neurological disorder is lithium carbonate. In a still further aspect, the lithium salt administered to treat the neurological disorder is lithium citrate.

In a further aspect, the mammal of the method has been diagnosed with a need for treatment of a psychiatric disorder. In a still further aspect, the method further comprises the step of identifying a mammal in need of treatment of a psychiatric disorder. In a yet further aspect, the psychiatric disorder is selected from bipolar disorder, major depression, schizoaffective disorder, schizophrenic disorder, impulse control disorders, mixed bipolar disorder, hyperactivity with psychotic components, hyperactivity with neurotic components, hyperactivity with aggressive behavior, hyperactivity with aggressive outbursts, mania in bipolar disorder, prophylaxis for depression, prophylaxis for mania in bipolar disorder, and unipolar depression. In an even further aspect, the psychiatric disorder is selected from bipolar disorder, major depression, schizoaffective disorder, schizophrenic disorder, and mixed bipolar disorder. In a still further aspect, the psychiatric disorder is bipolar disorder. In a yet further aspect, the mammal is administered a lithium salt to treat the psychiatric disorder. In an even further aspect, the lithium salt administered to treat the psychiatric disorder is lithium carbonate. In a still further aspect, the lithium salt administered to treat the psychiatric disorder is lithium citrate.

In a further aspect, the mammal of the method has been diagnosed with a need for treatment of a disorder selected from neutropenia and anemia. In a still further aspect, the mammal of the method has been diagnosed with a need for treatment of neutropenia. In a yet further aspect, the mammal of the method has been diagnosed with a need for treatment of anemia. In an even further aspect, the method further comprises the step of identifying a mammal in need of treatment of a disorder selected from neutropenia and anemia. In a still further aspect, the method further comprises the step of identifying a mammal in need of treatment of neutropenia. In a yet further aspect, the method further comprises the step of identifying a mammal in need of treatment of anemia. In an even further aspect, the mammal is administered a lithium salt to treat a disorder selected from neutropenia and anemia. In a still further aspect, the lithium salt administered to treat a disorder selected from neutropenia and anemia is lithium carbonate. In a yet further aspect, the lithium salt administered to treat a disorder selected from neutropenia and anemia is lithium citrate.

In a further aspect, the nephrogenic diabetes insipidus of the method is acquired nephrogenic diabetes insipidus. In a still further aspect, the acquired nephrogenic diabetes insipidus is induced by administration of a therapeutic agent. In a yet further aspect, the administration of the therapeutic agent precedes the administration of the compound. In an even further aspect, the therapeutic agent is selected from acetohexamide, an aminoglycoside, amphotericin B, bumetanide, clozapine, colchicine, a corticosteroid, demeclocycline, ethacrynic acid, foscarnet, furosemide, gentamicin, glyburide, ifosfamide, a lithium salt, mannitol, methoxyflurane, propoxyphene, tolazamide, torsemide, and vinblastine. In a still further aspect, the therapeutic agent is selected from clozapine, foscarnet, and a lithium salt. In a yet further aspect, the therapeutic agent that induces the acquired nephrogenic diabetes insipidus is a lithium salt. In an even further aspect, the therapeutic agent is lithium carbonate. In a still further aspect, the therapeutic agent is lithium citrate. In a yet further aspect, the therapeutic agent that induces the acquired nephgrogenic diabetes insipidus is a loop diuretic. In an even further aspect, the loop diuretic is selected from torsemide, furosemide, bumetanide, and ethacrynic acid.

In a further aspect, the acquired nephrogenic diabetes insipidus is induced by a pathophysiological condition. In a still further aspect, the pathophysiological condition that induces the acquired nephrogenic diabetes insipidus is selected from amyloidosis, analgesic nephropathy, chronic hypercalcemia, chronic kidney failure, hypokalemia, hypercalcemia, kidney disease, multiple myeloma, polycystic kidney disease, protein starvation, pyelonephritis, sarcoidosis, and sickle cell disease.

In a further aspect, the acquired nephrogenic diabetes insipidus is induced by a post-obstructive uropathy. In a still further aspect, the acquired nephrogenic diabetes insipidus is induced by pregnancy.

In a further aspect, the compound compound of the method is a modulator of a receptor selected from $P2Y_{12}$, $P2Y_{13}$, $P2Y_{14}$, GPR34, GPR34-like, GPR82, GPR87, and GPR171. In a still further aspect, the compound is a $P2Y_{12}$ modulator. In a yet further aspect, the $P2Y_{12}$ modulator is an antagonist.

In a further aspect, the compound is selected from clopidogrel, prasugrel, and ticagrelor. In a still further aspect, the compound is clopidogrel. In a yet further aspect, the compound is prasugrel. In an even further aspect, the compound is ticagrelor.

In a further aspect, the method further comprises co-administration of a $P2Y_2$ modulator with the compound.

g. Methods of Treating Age Related Disorders

Starting at age 40, the maximal capacity to concentrate urine gradually decreases, resulting in loss of water and electrolytes, and the associated morbidity. The rate of decline is accentuated in the presence of conditions, such as hypertension, diabetes mellitus and chronic usage of certain medications. Concentration of urine by the kidney is regulated by arginine vasopressin (AVP) or the anti-diuretic hormone (ADH) synthesized and released into the circulation by the hypothalamus in the brain, in response to a decrease in plasma volume or an increase in plasma osmolality. Impaired water handling by the aging kidney due to sluggish release of AVP by the aging brain has been postulated as a cause. However, recent studies revealed that the aging kidney is also sluggish in response to supra-physiological levels of AVP. Thus, it appears that defects in both the aging brain and the kidney plays a concerted role in this important geriatric problem.

It was recently observed that pharmacological blockade of ADP-activated $P2Y_{12}$ receptor (R), expressed in the brain and the kidney, by Plavix® (clopidogrel bisulfate) significantly increased the urinary concentration in rodents associated with increased AVP in the urine (surrogate for plasma AVP levels), and aquaporin-2 (AQP2) water channel protein in the kidney. In parallel, it was observed that Plavix® blocked the development of AVP-resistant polyuria in lithium-treated rodents, consistent with $P2Y_{12}$-R blockade re-sensitizing the kidney to the action of AVP.

Therefore, pharmacological blockade of $P2Y_{12}$-R can ameliorate age-related defect in urinary concentration by enhancing the AVP release from hypothalamus in the brain and/or sensitizing the kidney to the action of AVP.

Disclosed herein is a method for treating age-related defects in urinary concentration in a mammal, comprising the step of administering to the mammal an effective amount of a ADP-(P2Y12)-like receptor modulator, thereby increasing urinary concentration in the mammal.

In a further aspect, the mammal is human. In a yet further aspect, the mammal has been diagnosed with a need for treatment of age related defects in urinary concentration prior to the administering step. In a still further aspect, the method further comprises the step of identifying a mammal in need of treatment of urinary concentration.

In a further aspect, an effective amount of an ADP-(P2Y12)-like receptor modulator of the method is a therapeutically effective amount. In a still further aspect, an effective amount of an ADP-(P2Y12)-like receptor modulator of the method is a prophylactically effective amount.

In a further aspect, the ADP-($P2Y_{12}$)-like receptor modulator is a modulator of a receptor selected from $P2Y_{12}$, $P2Y_{13}$, $P2Y_{14}$, GPR34, GPR34-like, GPR82, GPR87, and GPR171. In a further aspect, the ADP-($P2Y_{12}$)-like receptor modulator is selected from an antagonist, a negative allosteric modulator, and an inverse agonist. In a still further aspect, the ADP-($P2Y_{12}$)-like receptor modulator is an antagonist. In a yet further aspect, the antagonist is selected from a thienopyridine, a cyclopentyltriazolopyrimidine, a nucleotide analog, and a nucleoside analog. In an even further aspect, the antagonist is a reversible antagonist. In a yet further aspect, the antagonist is an irreversible antagonist. In a still further aspect, the antagonist is $P2Y_{12}$ antagonist.

In a further aspect, the ADP-($P2Y_{12}$)-like receptor modulator is selected from clopidogrel, ticlopidine, prasugrel, ticagrelor, cangrelor, and elinogrel. In a yet further aspect, the ADP-($P2Y_{12}$)-like receptor modulator is selected from clopidogrel, prasugrel, and ticagrelor. In a still further aspect, the ADP-($P2Y_{12}$)-like receptor modulator is clopidogrel. In an even further aspect, the ADP-($P2Y_{12}$)-like receptor modulator is prasugrel. In a still further aspect, the ADP-($P2Y_{12}$)-like receptor modulator is ticagrelor.

In a further aspect, the ADP-($P2Y_{12}$)-like receptor modulator is a $P2Y_{12}$ modulator. In an even further aspect, the $P2Y_{12}$ modulator is selected from clopidogrel, ticlopidine, prasugrel, ticagrelor, cangrelor, and elinogrel. In a yet further aspect, $P2Y_{12}$ modulator is selected from clopidogrel, prasugrel, and ticagrelor. In a still further aspect, the $P2Y_{12}$ modulator is clopidogrel. In an even further aspect, the $P2Y_{12}$ modulator is prasugrel. In a still further aspect, $P2Y_{12}$ modulator is ticagrelor.

In a further aspect, the ADP-($P2Y_{12}$)-like receptor antagonist is selected from clopidogrel, ticlopidine, prasugrel, ticagrelor, cangrelor, and elinogrel. In a still further aspect, the ADP-($P2Y_{12}$)-like receptor antagonist is selected from clopidogrel, prasugrel, and ticagrelor. In a yet further aspect, the ADP-($P2Y_{12}$)-like receptor antagonist is clopidogrel. In an even further aspect, the ADP-($P2Y_{12}$)-like receptor antagonist is prasugrel. In a yet further aspect, the ADP-($P2Y_{12}$)-like receptor antagonist is ticagrelor.

In a further aspect, the $P2Y_{12}$ antagonist is selected from clopidogrel, ticlopidine, prasugrel, ticagrelor, cangrelor, and elinogrel. In a still further aspect, the $P2Y_{12}$ antagonist is selected from clopidogrel, prasugrel, and ticagrelor. In a yet further aspect, the $P2Y_{12}$ antagonist is clopidogrel. In an even further aspect, the $P2Y_{12}$ antagonist is prasugrel. In a yet further aspect, the $P2Y_{12}$ antagonist is ticagrelor. In a still further aspect, the antagonist is a selective $P2Y_{12}$ antagonist.

2. Manufacture of a Medicament

In one aspect, the invention relates to a method for the manufacture of a medicament for treating a diabetes insipidus disorder in a mammal comprising combining a therapeutically effective amount of a disclosed compound with a pharmaceutically acceptable carrier or diluent.

3. Use of Compounds

In one aspect, the invention relates to the use an ADP-($P2Y_{12}$)-like receptor modulator in the manufacture of a medicament for the therapeutic and/or prophylactic treatment of nephrogenic diabetes insipidus.

In various aspects, the invention relates to the use an ADP-($P2Y_{12}$)-like receptor modulator in the manufacture of an anti-diuretic agent in a package together with instructions for its use in the treatment of nephrogenic diabetes insipidus.

In a further aspect, the ADP-($P2Y_{12}$)-like receptor modulator of the use is a modulator of a receptor selected from $P2Y_{12}$, $P2Y_{13}$, $P2Y_{14}$, GPR34, GPR34-like, GPR82, GPR87, and GPR171. In a still further aspect, the ADP-($P2Y_{12}$)-like receptor modulator is a modulator of the $P2Y_{12}$ receptor. In a yet further aspect, the ADP-(P2Y$_{12}$)-like receptor modulator is an antagonist. In an even further aspect, the ADP-(P2Y$_{12}$)-like receptor modulator is an inhibitor.

In a further aspect, the ADP-(P2Y$_{12}$)-like receptor modulator of the use is selected from clopidogrel, ticlopidine, prasugrel, ticagrelor, cangrelor, and elinogrel. In a still further aspect, the ADP-(P2Y$_{12}$)-like receptor modulator is selected from clopidogrel, prasugrel, and ticagrelor. In a yet further aspect, the ADP-(P2Y$_{12}$)-like receptor modulator is clopidogrel. In an even further aspect, the ADP-(P2Y$_{12}$)-like receptor modulator is prasugrel. In a still further aspect, the ADP-(P2Y$_{12}$)-like receptor modulator is ticagrelor.

4. Kits

In one aspect, the invention relates to a kit comprising a lithium salt one or more of: a) at least one agent known to decrease ADP-(P2Y$_{12}$)-like receptor activity; b) at least one agent known to treat nephrogenic diabetes insipidus; c) instructions for treating a neurological disorder; d) instructions for a treating a psychiatric disorder; or e) instructions for treating nephrogenic diabetes insipidus.

In a further aspect, the lithium salt and the at least one agent of the kit are co-formulated. In a still further aspect, the lithium salt and the at least one agent of the kit are co-packaged. In a yet further aspect, the lithium salt of the kit is lithium carbonate.

In a further aspect, the at least one agent of the kit known to treat nephrogenic diabetes insipidus is selected from a thiazide, a nonsteroidal antiinflammatory agent, a prostaglandin inhibitor, and a potassium-sparing diuretic. In a still further aspect, the thiazide is selected from bendroflumethiazide, chlorothiazide, chlorthalidone, metolazone, indapamide, methyclothiazide, hydrochlorthiazide, and polythiazide. In a yet further aspect, the at least one agent known to treat nephrogenic diabetes insipidus is selected from amiloride, AVP, bendroflumethiazide, chlorothiazide, chlorthalidone, desmopressin, metolazone, indapamide, methyclothiazide, hydrochlorthiazide, and polythiazide.

In a further aspect, the instructions of the kit further provide that the lithium salt and the at least one agent are administered to a human. In a still further aspect, the instructions of the kit further provide that the lithium salt and the at least one agent are co-administered.

In a further aspect, the instructions of the kit further provide that lithium salt and the at least one agent are administered to a human diagnosed with a need for treatment of neurological or psychiatric disorder prior to the administering step. In a still further aspect, the neurological disorder is selected from acute brain injury and chronic neurodegenerative disease. In an even further aspect, the acute brain injury is selected from stroke, ischemia reperfusion injury, diffuse cerebral hypoxia, focal cerebral ischemia, cerebral infarction, and global cerebral ischemia. In a still further aspect, the chronic neurodegenerative disorder is selected from Alzheimer's disease, Parkinson's disease, and Huntington's disease. In a yet further aspect, the psychiatric disorder is bipolar disorder.

In a further aspect, the instructions further provide that lithium salt and the at least one agent are administered to a human diagnosed with a need for treatment of the nephrogenic diabetes insipidus prior to the administering step. In a still further aspect, the instructions further provide that the nephrogenic diabetes insipidus is acquired nephrogenic diabetes insipidus. In a yet further aspect, the acquired nephrogenic diabetes insipidus is induced by administration of a therapeutic agent. In an even further aspect, the therapeutic agent precedes the administration of the pharmaceutical composition.

In a further aspect, the therapeutic agent that induces the acquired nephrogenic diabetes insipidus is selected from acetohexamide, an aminoglycoside, amphotericin B, bumetanide, clozapine, colchicine, a corticosteroid, demeclocycline, ethacrynic acid, foscarnet, furosemide, gentamicin, glyburide, ifosfamide, a lithium salt, mannitol, methoxyflurane, propoxyphene, tolazamide, torsemide, and vinblastine. In a yet further aspect, the therapeutic agent that induces the acquired nephrogenic diabetes insipidus is a lithium salt. In an even further aspect, the lithium salt is lithium carbonate. In a still further aspect, the lithium salt is lithium citrate.

In a further aspect, the therapeutic agent that induces the acquired nephrogenic diabetes insipidus is a loop diuretic. In a still further aspect, the loop diuretic is selected from torsemide, furosemide, bumetanide, and ethacrynic acid.

In a further aspect, the acquired nephrogenic diabetes insipidus is induced by a pathophysiological condition. In a still further aspect, the pathophysiological condition is selected from chronic kidney failure, kidney disease, hypokalemia, hypercalcemia, sickle cell disease, and protein starvation.

In a further aspect, the acquired nephrogenic diabetes insipidus is induced by by a post-obstructive uropathy. In a still further aspect, the acquired nephrogenic diabetes insipidus is induced by pregnancy.

In a further aspect, the ADP-(P2Y$_{12}$)-like receptor modulator of the kit is a modulator of a receptor selected from P2Y$_{12}$, P2Y$_{13}$, P2Y$_{14}$, GPR34, GPR34-like, GPR82, GPR87, and GPR171. In a still further aspect, the ADP-(P2Y$_{12}$)-like receptor modulator is a P2Y$_{12}$ modulator. In a yet further aspect, the P2Y$_{12}$ modulator is selected from clopidogrel, ticlopidine, prasugrel, ticagrelor, cangrelor, and elinogrel. In an even further aspect, the P2Y$_{12}$ modulator is selected from clopidogrel, prasugrel, and ticagrelor. In a still further aspect, the P2Y$_{12}$ modulator is clopidogrel. In a yet further aspect, the P2Y$_{12}$ modulator is prasugrel. In an even further aspect, the P2Y$_{12}$ modulator is ticagrelor.

In a further aspect, the ADP-(P2Y$_{12}$)-like receptor modulator of the kit is selected from an antagonist, a negative allosteric modulator, and an inverse agonist. In a still further aspect, the ADP-(P2Y$_{12}$)-like receptor modulator of the kit is an antagonist. In a yet further aspect, the antagonist is selected from a thienopyridine, a cyclopentyltriazolopyrimidine, a nucleotide analog, and a nucleoside analog. In an even further aspect, antagonist is a reversible antagonist. In a still further aspect, the antagonist is an irreversible antagonist. In a yet further aspect, the antagonist is a selective P2Y$_{12}$ antagonist.

In a further aspect, the ADP-(P2Y$_{12}$)-like receptor modulator of the kit is selected from clopidogrel, ticlopidine, prasugrel, ticagrelor, cangrelor, and elinogrel. In a still further aspect, the ADP-(P2Y12)-like receptor modulator of the kit is selected from clopidogrel, prasugrel, and ticagrelor. In a yet further aspect, the ADP-(P2Y12)-like receptor modulator of the kit is clopidogrel. In an even further aspect, the ADP-(P2Y12)-like receptor modulator of the kit is prasugrel. In a still further aspect, the ADP-(P2Y12)-like receptor modulator of the kit is ticagrelor.

In a further aspect, the ADP-(P2Y$_{12}$)-like receptor modulator of the kit is P2Y$_{12}$ an antagonist. In an even further aspect, the P2Y$_{12}$ antagonist is selected from clopidogrel, ticlopidine, prasugrel, ticagrelor, cangrelor, and elinogrel. In a still further aspect, the P2Y$_{12}$ antagonist is selected from clopidogrel, prasugrel, and ticagrelor. In a yet further aspect, the $P2Y_{12}$ antagonist is clopidogrel. In an even further aspect, the $P2Y_{12}$ antagonist is prasugrel. In a still further aspect, the $P2Y_{12}$ antagonist is ticagrelor.

In a further aspect, the kit further comprises a $P2Y_2$ modulator.

In one aspect, the invention relates to a kit comprising a lithium salt one or more of: a) at least one agent selected from clopidogrel, ticlopidine, prasugrel, ticagrelor, cangrelor, and elinogrel; b) at least one agent known to treat nephrogenic diabetes insipidus; c) instructions for treating a neurological disorder; d) instructions for a treating a psychiatric disorder; or e) instructions for treating nephrogenic diabetes insipidus.

In a further aspect, the at least one agent is selected from clopidogrel, prasugrel, and ticagrelor. In a yet further aspect, the at least one agent is clopidogrel. In a still further aspect, the at least one agent is prasugrel. In an even further aspect, the at least one agent is ticagrelor. In a still further aspect, the at least one agent selected from clopidogrel, ticlopidine, prasugrel, ticagrelor, cangrelor, and elinogrel is a modulator of a receptor selected from $P2Y_{12}$, $P2Y_{13}$, $P2Y_{14}$, GPR34, GPR34-like, GPR82, GPR87, and GPR171. In a yet further aspect, the at least one agent selected from clopidogrel, ticlopidine, prasugrel, ticagrelor, cangrelor, and elinogrel is a $P2Y_{12}$ modulator. In an even further aspect, the at least one agent selected from clopidogrel, ticlopidine, prasugrel, ticagrelor, cangrelor, and elinogrel is a P2Y12 antagonist.

In a further aspect, the kit comprises a disclosed compound.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

5. Non-Medical Uses

Also provided are the uses of the disclosed compounds as pharmacological tools in the development and standardization of in vitro and in vivo test systems for the evaluation of the effects of ADP-($P2Y_{12}$)-like receptor modulators in laboratory animals such as cats, dogs, rabbits, monkeys, rats and mice, as part of the search for new therapeutic agents for the treatment of acquired nephrogenic diabetes insipidus. In a further aspect, provided are the uses of the disclosed compounds as pharmacological tools in the development and standardization of in vitro and in vivo test systems for the evaluation of the effects of $P2Y_{12}$ receptor modulators in laboratory animals such as cats, dogs, rabbits, monkeys, rats and mice, as part of the search for new therapeutic agents for the treatment of acquired nephrogenic diabetes insipidus.

J. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. Experimental Animals

Animal experiments: Male Sprague-Dawley rats were purchased from Charles River (Wilmington, Mass., USA), and Brattleboro mutant rats that lack AVP (HsdBlu:BRAT-Avpdi) were obtained from the Rat Resource & Research Center (RRRC), University of Missouri, Columbia, Mo., USA. Mice (B6D2 genetic background) were bred in-house. All animals had free access to drinking water and standard rodent chow during the experimental period of 2 weeks. Lithium-added chow (40 mmol Li/kg chow) was custom prepared (MP Biomedicals, Aurora, Ohio, USA). Clopidogrel bisulfate was administered orally by powdering and dissolving Plavix® tablets (Bristol-Myers Squibb, New York, N.Y., USA) in drinking water. The concentration of the drug in the drinking water was adjusted daily based on the water consumption of the animals the previous day. The clopidogrel dose used in Sprague-Dawley rats (20 mg/kg bw/day) was the same as used by other investigators (de La Crux et al, 2003; Graciano et al, 2008). In mice, clopidogrel was administered at a dose of 80 mg/kg bw/day. When compared with the human clinical dose of Plavix®, and adjusted to the Km factor (ratio of body surface area to body weight) of the species (man vs. rat or mouse) (Reagan-Shaw et al, 2007), the doses used in rats or mice were 2.5- and 5-fold higher, respectively. Toxicological evaluation of clopidogrel showed that doses as high as 165 mg/kg bw/day upto 4 weeks in rats were free from toxicity (Reist et al, 2000). A higher dose of clopidogrel (40 mg/kg bw/day) was used in Brattleboro rats to ensure an unequivocal outcome whether positive or negative. Twenty-four hour urine samples were collected by placing the animals in the appropriate metabolic cages designed for rats and mice. Blood and kidney tissues were collected at necropsy. Cortical, outer and inner medullary regions of the kidneys were dissected out and processed for laboratory assays.

Male Sprague-Dawley rats weighing 200-300 g and male or female B6D2 mice weighing about 30 g were used in these studies. Animals were housed in plastic shoebox cages with microisolater lid tops, with 12 h dark/light cycles, and under normal conditions of ambient temperature and humidity. All animals had free access to drinking water and standard rodent chow, unless restricted by the experimental manipulations. Animals were acclimated to the housing conditions at least for one week prior to commencement of experimental procedures. Lithium was administered orally by feeding the animals a lithium-added diet (40 mmol/kg chow) custom prepared by MP Biomedicals (Aurora, Ohio) for two weeks. Twenty-four hour urine samples were collected from at prior to the experimental procedures, and periodically during the experimental duration. For this, animals were placed in plastic metabolic cages (different ones for rats and mice), one animal per cage, with free access to food and drinking water. All animals were euthanized at the end of the experimental period by American Veterinary Association approved methods. Blood and tissue samples were collected at necropsy. Cortical and medullary regions of the kidneys were dissected out, flash frozen and then processed in the laboratory.

2. Blood, Tissue and Urine Analysis

Osmolalities of clear urine samples were measured by vapor pressure method (Wescor, Logan, Utah, USA). Microhematocrit was determined by centrifuging free-flowing blood collected in heparinized capillary tubes in a microhematocrit centrifuge (Clay Adams, Parsippany, N.J., USA). Urinary excretion of AVP was quantified by a commercial ELISA kit (Enzo Life Sciences, Farmingdale, N.Y., USA). Total nitrate/nitrite contents of urine samples were determined by a commercial kit (Cayman Chemical, Ann Arbor, Mich.).Na, Li and K levels in serum and/or urine were determined on EasyElectrolyte® (Medica Corp., Bedford, Mass., USA) or on AVL9180 Electrolyte Analyzer. Urinary excretion of PGE2 metabolite and cyclic AMP were determined by the use of commercial EIA kits (Cayman Chemical Co., Ann Arbor, Mich.). Based on serum and urine analysis, electrolyte-free clearance [CH2O(e)] was computed using the formula $C_{H2O}(e)=V\times((1-UNa+UK)/PNa)$, where V=urine volume, UNa and UK are urine Na and K, and PNa is plasma Na, respectively (Schrier 2006). Lithium levels in inner medullary tissue homogenates were assayed by Inductively Coupled Plasma-Mass Spectrometry (ICPMS) by Exova (Santa Fe Springs, Calif., USA), and were normalized to their respective protein contents. ICPMS has a detection limit of 0.06 ppm for Li, with recovery of 91% in spiked samples. Li was not detectable in the homogenization medium (0.5% SDS and 0.02% sodium azide in ultrapure water).

3. Computation of Electrolyte-Free Water Clearance

Electrolyte-free water clearance (EFWC) was computed using the formula:

$$C_{H2O}(e)=V\times((1-UNa)\pm(UK/PNa))$$

where V=urine volume, UNa and UK are urine Na and K, respectively, and PNa is plasma Na. A negative value for $C_{H2O}(e)$ indicates electrolyte-free water absorption, and a positive value for $C_{H2O}(e)$ indicates electrolyte-free water excretion (Schrier R W. In: Renal and Electrolyte Disorders. Lippincott Williams Wilkins, 2010, page 12).

4. Measurement of Inner Medullary Tissue Lithium Levels

Inner medullary tissue samples were homogenized in ultrapure water containing 0.5% sodium dodecyl sulfate (SDS) and 0.05% sodium azide. Lithium levels in the homogenate were determined by Inductively Coupled Plasma-Mass Spectrometry (ICPMS) by the Exova (Santa Fe Springs, Calif.). Measured lithium levels were normalized to the protein contents of the homogenates. ICPMS has a detection limit of 0.06 ppm for lithium, with a recovery of 93% or more in spiked samples. Lithium was not detectable in the homogenization medium.

5. Quantitative Real-Time RT-PCR Assay

Quantitative Real-Time RT-PCR was performed essentially as described previously (Zhang Y, et al. (2009) Am J Physiol Renal Physiol 296: F1194-F1201, 2009; Zhang Y, et al. (2010) Am J Physiol Renal Physiol 298: F634-F642, 2010; Zhang Y, et al. (2011) Am J Physiol Renal Physiol 300:F657-F668, 2011; Zhang et al. (2012) Am J Physiol Renal Physiol 302:F70-F77). Total RNA from tissue samples was isolated by the TRIzol method (Invitrogen, Carlsbad, Calif.), according to the manufacturer's recommendation, and traces of genomic DNA in the samples were removed. cDNA was synthesized by SuperScript Reverse Transcriptase II (Invitrogen, Carlsbad, Calif.). Real-time PCR amplifications were carried out on the cDNA samples in Applied Biosystems 7500 Real-Time PCR System (Foster City, Calif.) with AmpliTaq Gold. cDNA was amplified for 40 cycles using SYBR Green for detection. Expression of β-actin was used to normalize the expression levels of $P2Y_{12}$ receptor. The sequences of primer pairs used were as indicated in Table II below. The primers used to amplify $P2Y_{12}$ is based on the sequence accession NM_022800.1 and is modified from the primers described by Tozaki-Saitoh, et al. (2008, J Neurosci 28:4949-4956), and the anticipated amplification product is 75 bp. The primers used to amplify (3-Actin is based on the sequence accession NM_031144.2 and is as described previously by Zhang, et al. (2008, J Am J Physiol Renal Physiol 295:F1715-F1724), and the anticipated amplification product is 207 bp. Specificity of amplifications was verified by sequencing the PCR product for $P2Y_{12}$ receptor and then by blasting in the National Center for Biotechnology Information (NCBI) database.

TABLE II

| Primer | Sequence |
|---|---|
| $P2Y_{12}$ Forward | TAACCATTGACCGATACCTGAAGA (SEQ ID NO: 1) |
| $P2Y_{12}$ Reverse | ATCTTCGCACCCAAAAGATTGC (SEQ ID NO: 2) |
| β-Actin Forward | CACCCGCGAGTACAACCTTC (SEQ ID NO: 3) |
| β-Actin Reverse | CCCATACCCACCATCACACC (SEQ ID NO: 4) |

6. Western Blotting of Tissue Samples

Tissue samples were prepared and immnoblotted for semi-quantitative determination of protein abundances of $P2Y_{12}$ receptor, and β-actin by the methods described previously (Zhang et al, ibid, 2008, 2009, 2010). Whole tissue homogenates were prepared in the presence of protease inhibitors, and the concentrations of proteins in the homogenates were determined, and solubilized in Laemmli buffer.

Then the solubilized proteins were size fractionated on 12% SDS-polyacrylamide gels. Quality of tissue sample preparation and equality of protein loading were verified by staining parallel-run loading gels with Coomassie-blue (Gelcode Blue, Pierce Endogen, Rockford, Ill.). The size fractionated proteins were electrotransferred to nitrocellulose membranes, and blocked with buffer containing non-fat milk. Differences in protein loading were corrected by normalizing the band densities of the target proteins to that of β-actin (polyclonal antibody from Biolegend, San Diego, Calif., USA). After washing, the blocked membranes were incubated with rabbit polyclonal antibodies to either $P2Y_{12}$ receptor (AnaSpec, Fremont, Calif.) or aquaporin-2 (AQP2; Zhang et al, ibid, 2008) or AQP1 (commercial source) or β-actin (Biolegend, San Diego, Calif.). Non-specific binding was prevented by incubation of the membranes with goat serum. Generation and characterization of AQP2 antibody (GN-762) was described previously (Kishore et al, 2000; Zhang et al, 2008). When peptide block was tested, prior to its use on the membranes the $P2Y_{12}$ receptor antibody was pre-adsorbed by incubation with the blocking peptide as per the instructions of the supplier (AnaSpec, Fremont, Calif.). After washing off the primary antibodies, the nitrocellulose membranes were incubated with a peroxidase-conjugated secondary antibody to rabbit IgG (Dako North America, Carpinteria, Calif.). Chemiluminescence reaction was used to detect sites of antigen-antibody reactions (SuperSignal Substrate; Pierce Endogen, Rockford, Ill.), and captured on an X-ray film. Images were digitized and band densities were quantified by using Un-San-It software (Silk Scientific, Orem, Utah). The band densities of AQP2 were normalized by the band densities of β-actin. Mean values of relative band densities thus obtained for $P2Y_{12}$ receptor were expressed as percent of the mean values obtained in the control group of animals.

7. Statistical Analysis

All quantitative data are presented as mean±SE. Comparisons among the means of multiple groups were made by analysis of variance (ANOVA), followed by the assessment of statistical significance by Tukey-Kramer Multiple Comparison Test or Studen-Newman-Keuls Multiple Comparison Test. Differences between the means of two groups were determined by unpaired t test, or where applicable, by Mann-Whitney nonparametric test. P values less than 0.05 were considered significant. InStat® (GraphPad Software, Inc., La Jolla, Calif.) software was used for statistical processing of the data.

8. $P2Y_{12}$ Receptor mRNA and Protein are Expressed in the Rat Kidney

Figure 2:
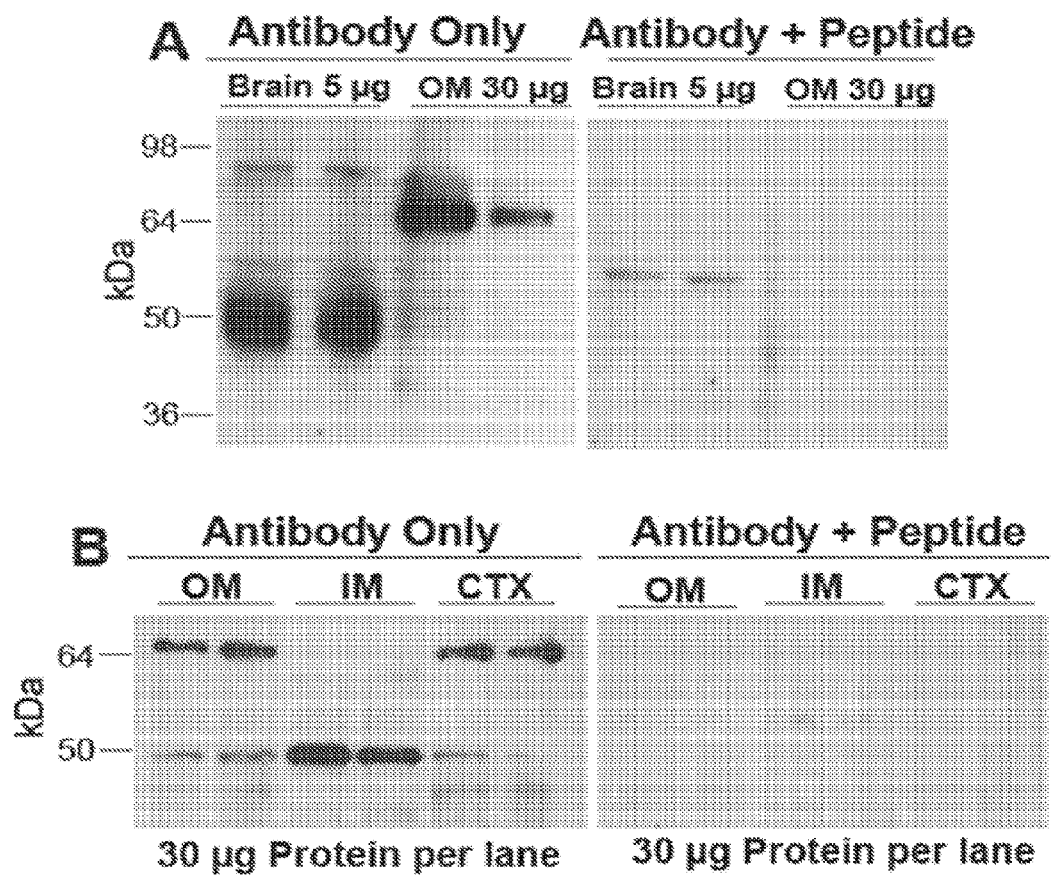
FIG. 2 shows representative data on the expression of $P2Y_{12}$-receptor protein in brain (Panel A) and kidney (Panel B) in rat. CTX—cortex. IM—inner medulla. OM—outer medulla.

Using real-time RT-PCR and gene-specific primer pairs, the relative expression of P2Y12 receptor mRNA in the kidney and different organs of Sprague-Dawley rats was determined (FIG. 1). The data in FIG. 1 show expression of $P2Y_{12}$ receptor mRNA in the brain, kidney and other organs of rat, relative to the expression of β-actin. Specificity of amplifications was confirmed by sequencing the PCR product and comparing the sequence obtained by BLAST comparison against NCBI databases. The highest expression was found in the brain, followed by the heart, and spleen. Surprisingly, quantifiable levels of expression were detected in the cortex, and outer and inner medullas of the kidney. The expression levels in the kidney are about 12-, 2.5- and 2-fold lower as compared to the brain, spleen and heart, respectively. In parallel, the levels of $P2Y_{12}$ receptor protein in brain and kidney were determined by immunoblot using a specific polyclonal antibody (AnaSpec, Fremont, Calif.). As shown in FIG. 2, the $P2Y_{12}$ receptor protein was detected in the kidney, albeit to a much lower level compared to the brain tissue. The data in Panel A of FIG. 2 show two specific bands in brain and kidney (OM—outer medulla). Both bands were ablated by pre-adsorption of the antibody with the blocking peptide. A distinct difference between the brain and kidney tissues in the amounts of protein loaded was observed. The data in Panel B of FIG. 2 show the relative abundance of the $P2Y_{12}$ bands in kidney outer medulla (OM), inner medulla (OM), and cortex (CTX) and their specificity. In both panels A and B, the two blots (antibody only and antibody+peptide) were exposed to the same X-ray film for the same duration of time. The two $P2Y_{12}$ bands detected (~48 kDa and ~70 kDa) appear to be specific for $P2Y_{12}$ receptor, because both were ablated by pre-adsorption of the antibody by the immunizing (blocking) peptide supplied by the manufacturer. Previously published data (Savi P, Zachayus J-L, et al., Proc Natl Acad Sci USA 103:11069-11074) suggests that the lower 48 kDa band corresponds to monomeric form of the receptor, whereas the upper 70 kDa band may be a modified form of the receptor protein, possibly a glycosylated form. Without wishing to be bound by a particular theory, the 70 kDa band does not seem to be a dimer, which occurs at a higher level as seen in the brain. The relative expression of these two proteins varied between the brain and different regions of the kidney.

9. Administration of Clopidogrel to Rats Increased Urinary Concentration

Clopidogrel bisulfate was given orally to a group of Sprague-Dawley rats (n=4) for 13 days by dissolving powdered Plavix® tablets (75 mg base; Bristol-Myers Squibb/Sanofi, Bridgeport, N.J.) in drinking water, so that the rats consumed at least 20 mg of clopidogrel bisulfate base per kg body weight per day. The concentration of the drug in the drinking water was adjusted daily based on the water consumption of the rats the previous day. Another group of rats (n=4) was given plain water and this group served as controls. Twenty-four hour water consumption and urine output in all rats were monitored at the beginning (day 0), at mid-point (days 6/7) and at the end (days 12/13) of the experimental period. Urinary excretion of AVP and PGE2 metabolite were determined by EIA. Renal tissue samples were processed by semi-quantitative immunoblotting for AQP2 and AQP1 water channel and P2Y12 receptor proteins. The results are shown in FIGS. 3 and 4.

Figure 3:
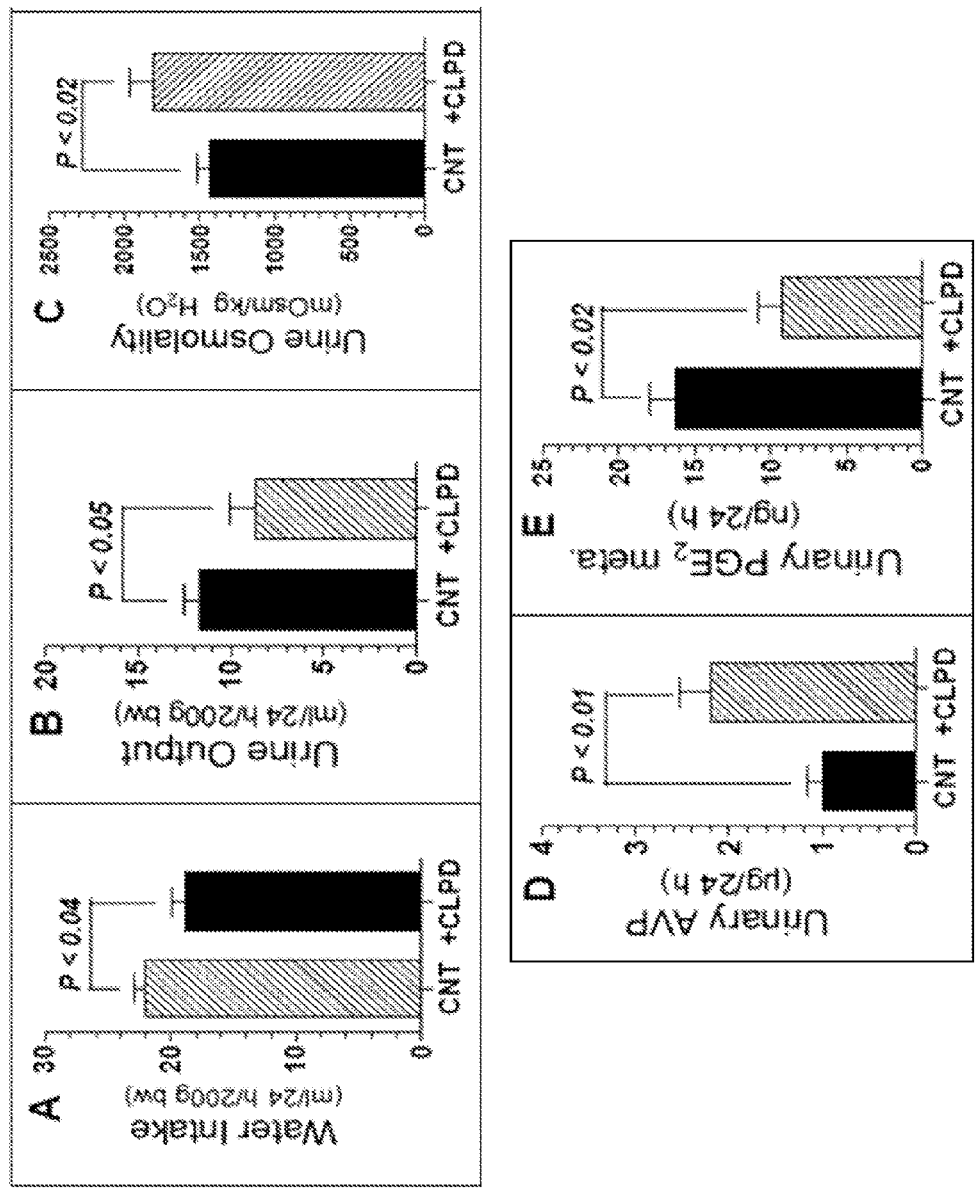
FIG. 3 shows representative data on the effect of administration of clopidogrel on water intake (Panel A), urine output (Panel B), urine osmolality (Panel C), urinary AVP (Panel D), and urinary PGE2 metabolite (Panel E) in rats. Clopidogrel was administered at a dose of 20 mg/kg body weight in drinking water for 13 days. CNT—control group, CLPD—clopidogrel group; mean±SE (n=4/group); P values by unpaired t test.

The data in FIG. 3 show the effect of clopidogrel in this study on water intake (Panel A), urine output (Panel B), urine osmolality (Panel C), urinary AVP (Panel D), and urinary PGE2 (Panel E). The data in FIG. 3 shows the mean±SE (n=4/group) and P values were determined by unpaired t test. Abbreviations used in FIG. 3 are as follows: AVP—arginine vasopressin; PGE2—prostaglandin E2; CNT—control group, and CLPD—clopidogrel group.

Figure 4:
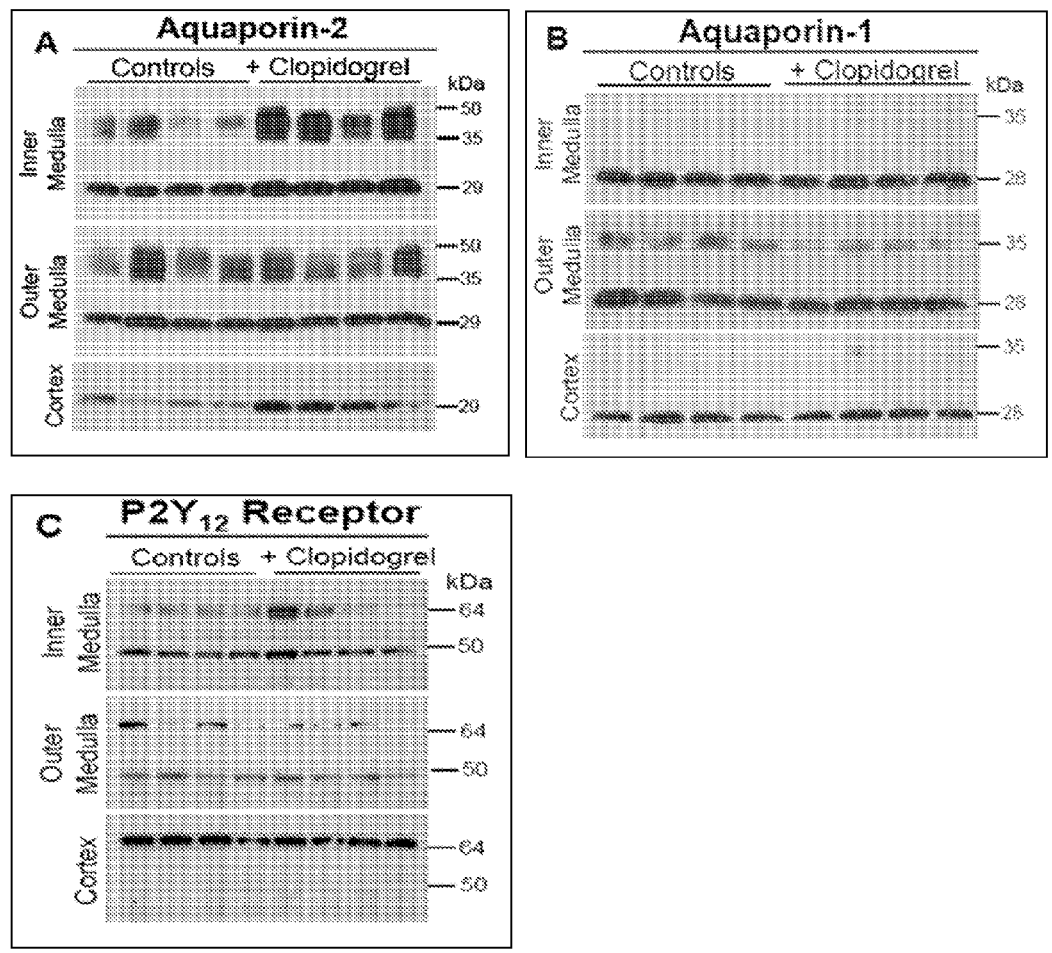
FIG. 4 shows representative data on the effect of administration of clopidogrel on the protein abundances of AQP2, AQP1 and $P2Y_{12}$ receptor in the kidney of rat.

The data in FIG. 4 show the effect of clopidogrel administration on the protein abundances of AQP2, AQP1 and $P2Y_{12}$ receptor in the kidney. The data (Panel A) suggest that clopidogrel significantly increased the AQP2 protein abundance in the inner medulla (1.9-fold; P<0.002), and cortex (2.7-fold; P<0.02), but not in the outer medulla (P=0.24). Clopidogrel did not appear to alter either the protein abundance of AQP1 water channel in the kidney (Panel B), or the protein abundance of P2Y12 receptor in the kidney (Panel C). Abbreviations used in FIG. 4 are as follows: AQP1—aquaporin 1 and AQP2—aquaporin 2.

10. Administration Clopidogrel Ameliorates Lithium-Induced Polyuria in Rats

The effect of administration of clopidogrel on lithium-induced polyuria in rats was determined. Groups of rats were administered either lithium-containing diet (40 mmol/kg chow; custom prepared by MP Biomedicals, Aurora, Ohio) or lithium-containing diet plus clopidogrel (20 mg per kg body weight per day in drinking water) for 13 days. Groups of rats that received either clopidogrel alone or no drug were included in the study. Results are shown in FIGS. 5 to 9.

Figure 5:
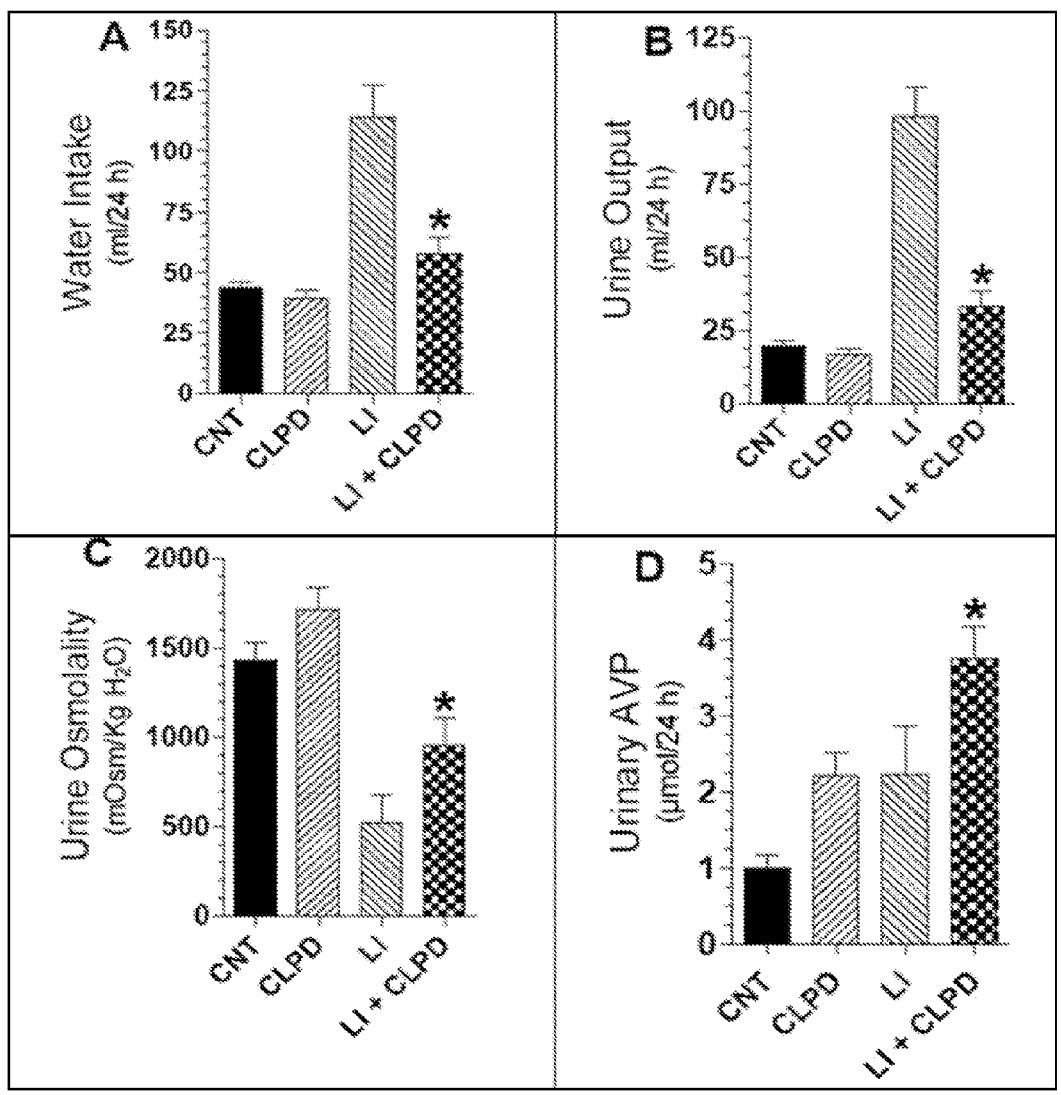
FIG. 5 shows representative data on the effect of clopidogrel on lithium-induced polyuria in rats. Groups of rats were fed lithium (Li)-added diet (40 mmol/kg chow) with or without addition of clopidogrel (CLPD; 20 mg/kg bw/day) to drinking water for 13 days. Groups of rats fed regular diet and received clopidogrel (CLPD) alone or no drug at all (CNT) were included. (Panel A) water intake, *P<0.001 vs. LI alone group; (Panel B) urine output; *P<0.001 vs. LI alone group; (Panel C) urine osmolality; *P<0.05 vs. LI alone group; and (Panel D) urinary AVP: *P<0.05 vs. LI or CLPD groups. CNT—control group, CLPD—clopidogrel-treated group; LI—lithium-treated group, LI+CLPD—clopidogrel- and lithium-treated group. Results are mean±SE (n=7 for Panels A to C; n=4 or 5 for Panel D); ANOVA followed by either Tukey Kramer Multiple Comparison Test or Bonferroni Test.

The data in FIG. 5 show the effect of clopidogrel on several parameters of lithium-induced polyuria in rats: (Panel A) water intake with *P<0.001 vs. LI alone group; (Panel B) urine output with *P<0.001 vs. LI alone group; (Panel C) urine osmolality with *P<0.05 vs. LI alone group; and (Panel D) urinary AVP with *P<0.05 vs. LI or CLPD groups. Abbreviations used in FIG. 5 are as follows: CNT—control group; CLPD—clopidogrel treated group; LI—lithium treated group; and LI+CLPD—lithium and clopidogrel treated group. Results shown are the mean±SE; n=7 for panels A to C; n=4 or 5 for panel D. Data were analyzed by ANOVA followed by either Tukey Kramer Multiple Comparison Test or Bonferroni Test.

Figure 6:
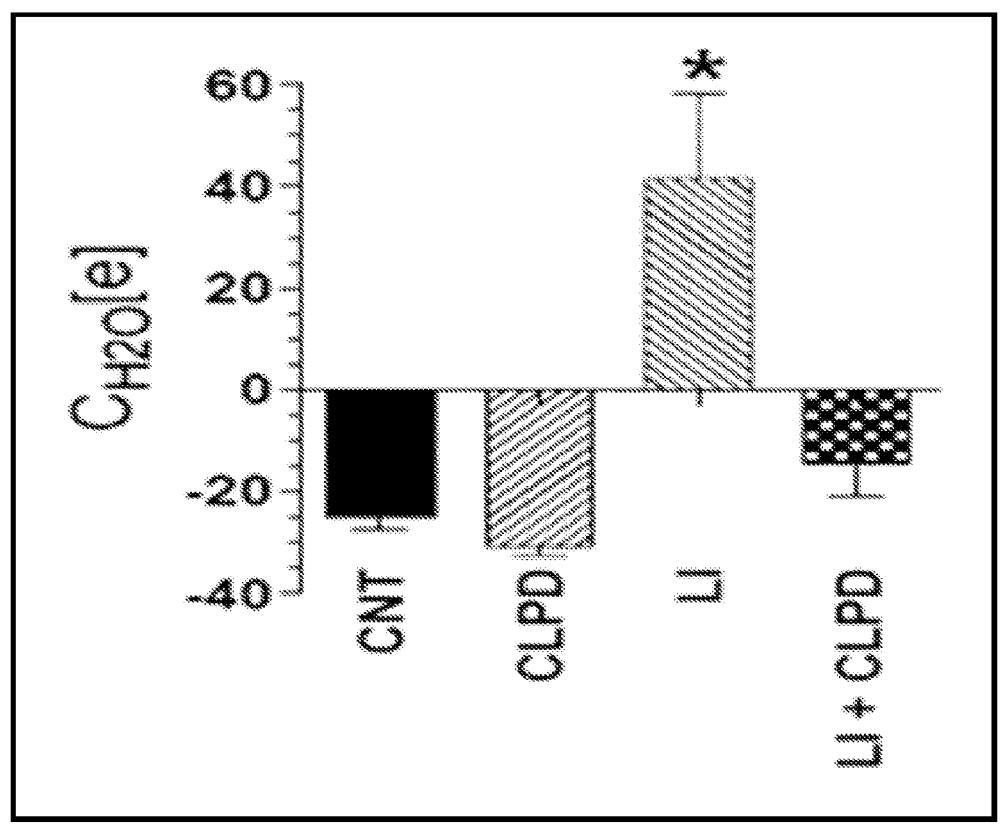
FIG. 6 shows representative data on the effect of clopidogrel on lithium-induced alterations in electrolyte-free water clearance ($C_{H2O}$[e]) in rats. LI or CLPD groups. CNT—control group, CLPD—clopidogrel-treated group; LI—lithium-treated group, LI+CLPD—clopidogrel- and lithium-treated group. *significantly different from all other groups.

The data shown in FIG. 6 are for the effect of clopidogrel on lithium-induced alterations in electrolyte-free water clearance ($C_{H_2O}(e)$), the computation of which is discussed above. In FIG. 6, * indicates the value is significantly different from all other groups.

Figure 7:
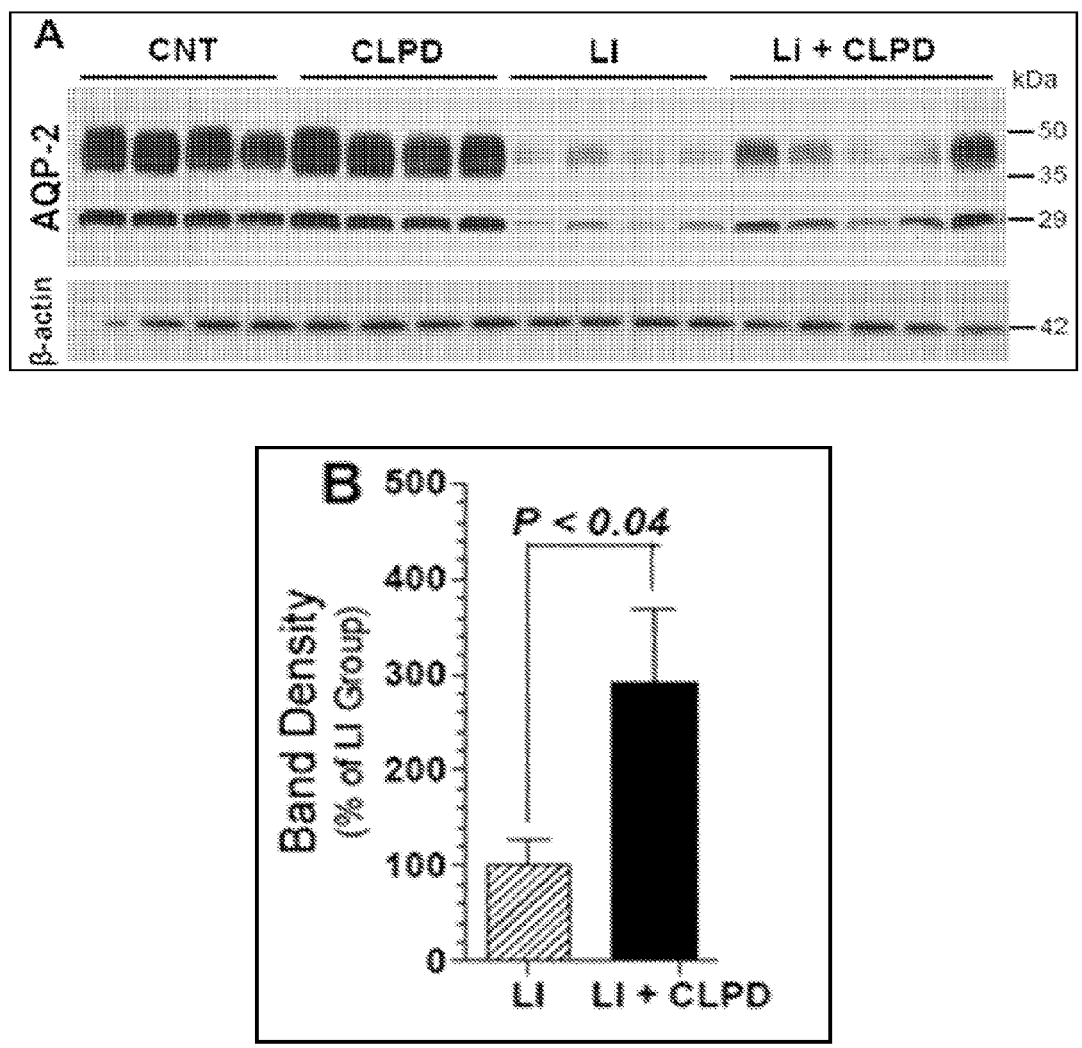
FIG. 7 shows representative data on the effect of clopidogrel on lithium-induced decrease in AQP2 in the inner medulla in rats. LI or CLPD groups. (Panel A) Immunoblots for AQP2 and β-actin protein bands; (Panel B) relative densitometry of bands in lithium alone and lithium+clopidogrel groups. CNT—control group, CLPD—clopidogrel-treated group; LI—lithium-treated group, LI+CLPD—clopidogrel- and lithium-treated group.

FIG. 7 shows the effect of clopidogrel on lithium-induced decrease in AQP2 protein in the inner medulla. The immunoblots for AQP2 and β-actin proteins are shown in Panel A. The AQP2 blot was deliberately over exposed to X-ray film to capture the very faint bands in LI alone group, thus the difference between the controls (CNT) and CLPD groups was negated due to pixel saturation. Relative densitometry of bands in lithium alone and lithium+clopidogrel groups is shown in Panel B, which quantitates the significant increase in AQP2 protein realized by treatment with clopidogrel.

Figure 8:
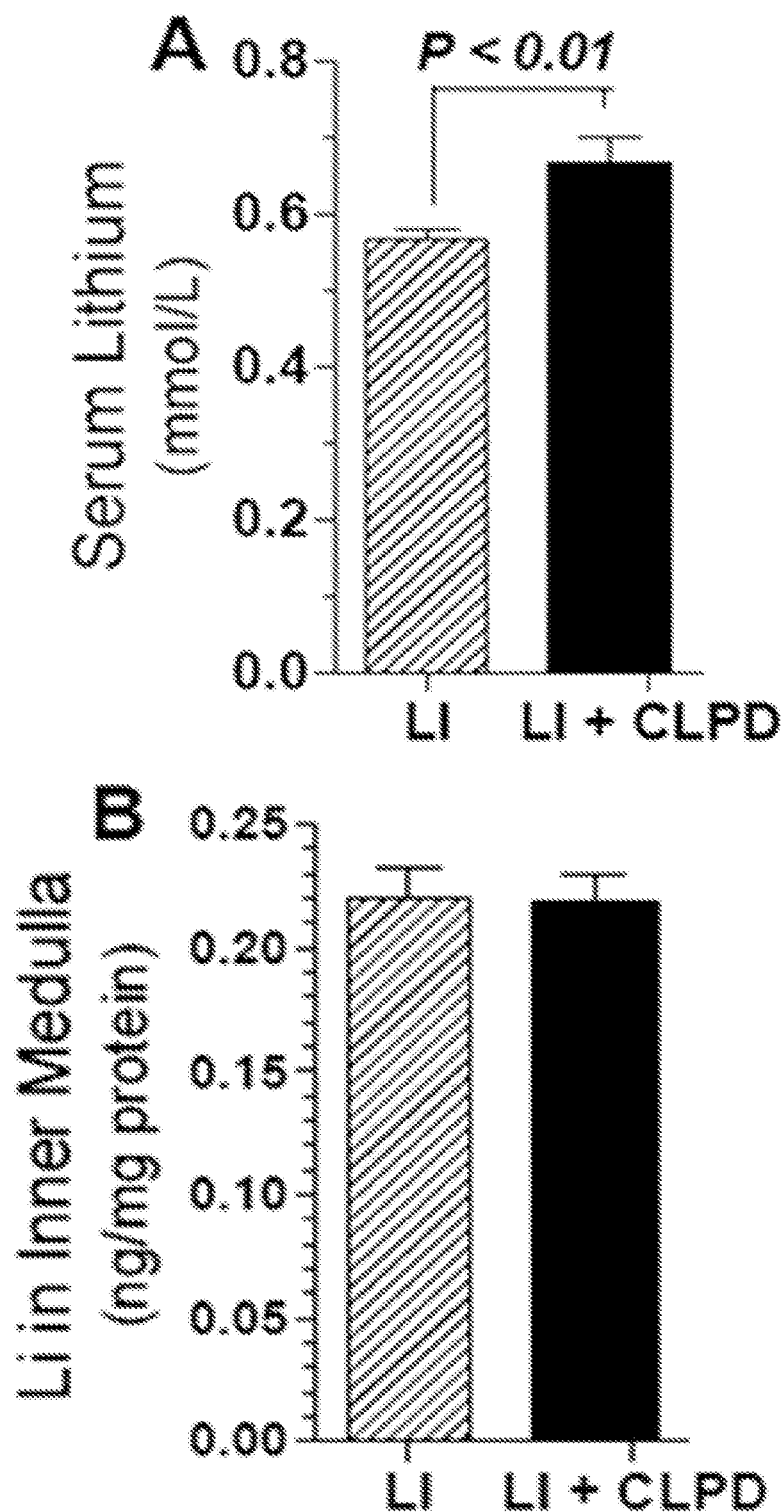
FIG. 8 shows representative data on the effect of clopidogrel on serum lithium levels (Panel A) and accumulation of lithium in the inner medulla (Panel B) of rats. Tissue lithium levels were quantified by Inductively-Coupled Plasma Mass Spectroscopy (ICPMS). n=4 or 5/group).

The data in FIG. 8 shows the effect of clopidogrel on serum lithium levels (Panel A) and the accumulation of lithium in the inner medulla (Panel B). Tissue lithium levels were quantified by Inductively-Coupled Plasma Mass Spectroscopy (ICPMS). Each group had n=4 or 5/group. The data show that the treatment with clopidogrel had a relatively small effect on serum lithium levels, but had no effect on the accumulation of lithium in the inner medulla.

As shown, clopidogrel significantly ameliorated lithium-induced polyuria. It should be noted that the dose of clopidogrel used in these studies (20 mg/kg/day) may require further optimization when translated to human in a clinical setting. Clopidogrel effectively reversed the lithium-induced solute-free water excretion (positive value), and when administered alone, modestly increased the solute-free water absorption (negative value). Elevated urinary AVP levels in lithium-treated rats are expected. Interestingly, it was observed that co-administration of clopidogrel augmented the lithium-induced urinary AVP levels. In parallel, it was observed that clopidogrel had a significant effect on the marked decrease of lithium-induced AQP2 protein abundance in the inner medulla, and without wishing to be bound by a particular theory, these data provide a molecular basis for the observed effect of clopidogrel on urinary variables analyzed. Finally, it is also clear that the observed effects of clopidogrel were not mediated by a reduction in blood levels or kidney medullary accumulation of lithium. In fact, the modest, yet significant increase in blood lithium level when administered with clopidogrel may be beneficial, as it may allow us to decrease the clinical dose of lithium, thus reducing its general toxicity as well. In summary, the studies show that co-administration of clopidogrel ameliorates lithium-induced polyuria.

11. Administration Clopidogrel Ameliorates Lithium-Induced Polyuria in Mice

Figure 9:
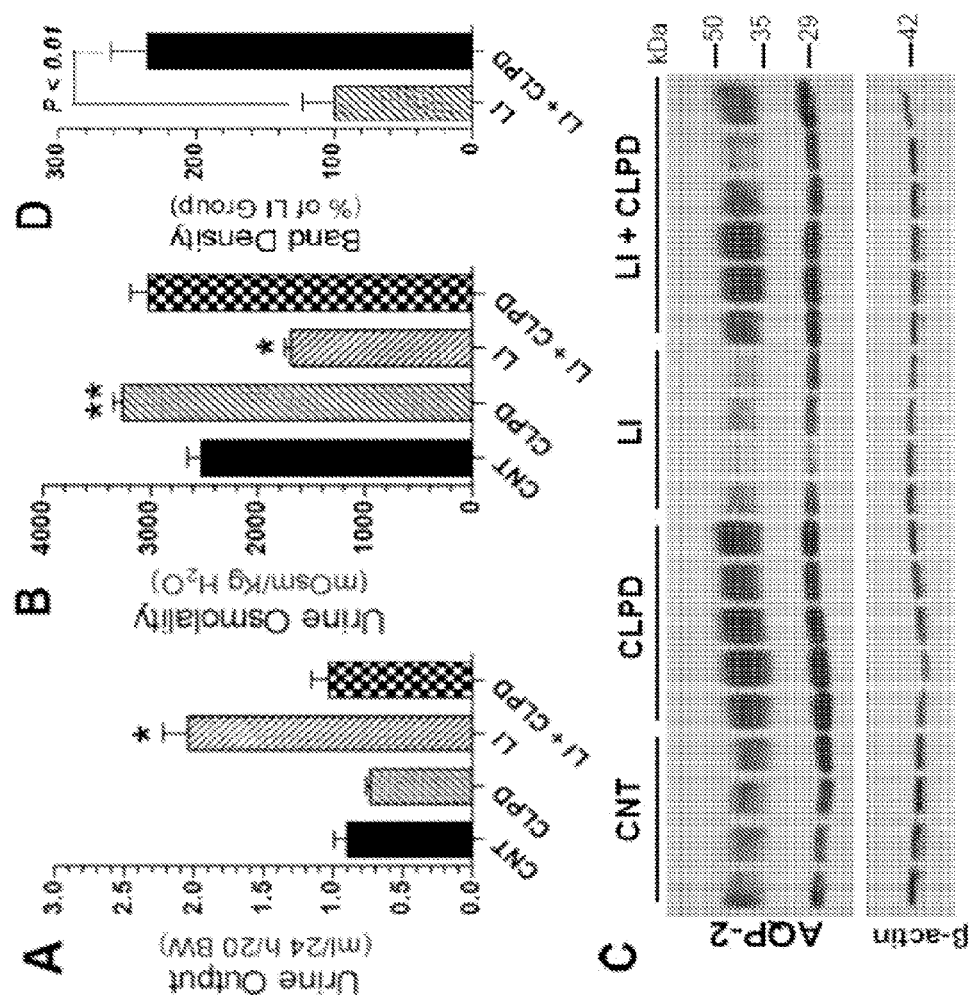
FIG. 9 shows that clopidogrel (CLPD) ameliorated Li (lithium)-induced NDI in mice. Groups of mice (B6D2 genetic background; n 5-7/group) were fed lithium(Li)-added diet (40 mmol/kg chow) with or without addition of clopidogrel (CLPD; 80 mg/kg bw/day) to drinking water for 14 days. Groups of mice fed regular diet and received clopidogrel (CLPD) alone or no drugs at all (CNT) were included. Urinary data obtained on the last two days were averaged. A, urine output; and B, urine osmolality, *significantly different from all other groups; **significantly different from the corresponding control (CNT) group. Panel C shows immunoblots of AQP2 and β-actin proteins, and D shows densitometry of AQP2 bands in LI and LI+CLPD groups relative to β-actin.

The effect of administration of clopidogrel on lithium-induced polyuria was determined in mice (B6D2 genetic background). Groups of mice were administered either a lithium-containing diet (40 mmol/kg chow; custom prepared by MP Biomedicals, Aurora, Ohio) or lithium-containing diet plus clopidogrel (80 mg per kg body weight per day in drinking water) for 14 days. Twenty-four urine samples were collected prior to the start of the treatment (day 0), on days 8 and 9, and days 13 and 14. The data plotted in the graphs represent the mean of the values obtained on the two consecutive days. Results are mean±SE; n=5 for LI alone group and n=6 for LI+CLPD group; ANOVA followed by Tukey Kramer Multiple Comparison Test. The results of this study are shown in FIG. 9.

The data show that administration of clopidogrel resulted in a significant decrease in water intake (Panel A, *P<0.05 or better vs. LI alone group) and urine output (Panel B, *P<0.001 vs. LI alone group). Consistent with these results, the data also show a significant increase in urine osmolality (Panel C, *P<0.001 vs. LI alone group). Thus, as shown in the FIG. 9, administration of clopidogrel completely blocked the development of lithium-induced polyuria and polydipsia in mice.

12. Prospective $P2Y_{12}$ Receptor Binding Assay

Generally agents useful in the disclosed methods display efficacy in assays of the $P2Y_{12}$ receptor. In vitro effects of the disclosed compounds heretofore are expected to be active as antagonists, inhibitors, or negative allosteric modulators of $P2Y_12$ in various in vitro assays known to the skilled person, such as a $P2Y_{12}$ receptor binding assay. These assays are typically conducted in using cells expressing a recombinant form of $P2Y_{12}$. For example, the ability of a test compound to bind to the $P2Y_{12}$ receptor was evaluated in a recombinant cell membrane binding assay. In this competitive binding assay, the test compound competes against a radiolabeled agonist for binding to the $P2Y_{12}$ receptor, expressed on the cell membrane. Inhibition of binding of the labeled material is measured and correlated to the amount and potency of the test compound. This binding assay is a modification of the procedure described by Takasaki, J. et. al, Mol. Pharmacol., 2001, Vol. 60, pg. 432. A membrane preparation can be prepared from Chinese Hamster Ovary (CHO) cells with recombinant expression of the human $P2Y_{12}$ receptor according to standard procedures as a source of $P2Y_{12}$.

An exemplary assay is as follows: Chinese Hamster Ovary (CHO) cells with recombinant expression of the human $P2Y_{12}$ receptor are cultured in 24 well cell-culture plates. Cells are washed three times with binding buffer (50 mM Tris pH 7.4, 100 mM NaCl, 1 mM EDTA, 0.5% BSA). The cells are then incubated with 0.5 ml per well binding buffer containing tritium-labeled 2-methyl-thio-adenosine 5'-diphosphate (2-methyl-S-ADP) (between about 100,000 and 300,000 dpm per well) and various concentrations of test compounds. After incubation at RT for 2 hours, cells are washed three times with binding buffer. Next the cells are solubilized by addition of 0.5 ml solubilization buffer (SDS, NaOH, and EDTA) and the content of each well is then transferred into beta-counter vials and 2.0 ml of Ultima Gold Scintillation liquid was added. After quantification of the cell-associated signal, extent of inhibition was calculated relative to maximal possible inhibition demonstrated by addition of excess of cold 2-methyl-S-ADP.

Alternatively, the antagonist, inhibitor, or negative allosteric modulator activity can be determined as follows herein. Briefly, to a 96-well microtiterplate the following are added: a) 24 µl of assay buffer (10 mM HEPES, 138 mM NaCl, 2.9 mM KCl, 12 mM NaHCO$_3$, 1 mM EDTA-Na, 0.1% BSA, pH 7.4); b) 1 µL compound in DMSO; c) 50 µL P2Y$_{12}$ CHO membrane (20 µg/ml) and after 15 min at RT; d) 25 µL of 1.61 nM $^{33}$P 2MeS-ADP (Perkin Elmer NEN custom synthesis, specific activity about 2100 Ci/mmol) in assay buffer.

After 20 min incubation at room temperature samples are transferred to 96-well microtiter filterplates (Millipore HTS GF/B), pre-wetted for 20 min with 300 µL of stop buffer (10 mM HEPES, 138 mM NaCl pH 7.4) and then filtered through completely with a Millipore plate vacuum. Next, wells are washed four times with 400 µl/well of stop buffer on a plate vacuum. The plate is disassembled and allowed to air dry overnight with the filter side up over night. The filter plates are snapped into adapter plates and 0.1 mL of Microscint 20 Scintillation Fluid (Perkin Elmer #6013621) is added to each well. The top of the filterplate is sealed with plastic plate covers. The sealed filterplate is incubated 2 hours at room temperature. A Microbeta Scintillation Counter is used to measure counts. The binding of compound is expressed as a % inhibition of specific binding, defined by subtraction of the background with 1 mM ADP. Compounds are diluted as 10 mM DMSO stocks and tested in a four-point, five-fold dilution series run in triplicate beginning at 10 µM, final concentration. Data are analyzed using a four-parameter curve fit with a fixed minimum and maximum experimentally defined as the average positive and negative controls on each plate.

13. Additional Experiments

Animal experiments: Male Sprague-Dawley rats were purchased from Charles River (Wilmington, Mass., USA), and Brattleboro mutant rats that lack AVP (HsdBlu:BRAT-Avp$^{di}$) were obtained from the Rat Resource & Research Center (RRRC), University of Missouri, Columbia, Mo., USA. Mice (B6D2 genetic background) were bred in-house. All animals had free access to drinking water and standard rodent chow during the experimental period of 2 weeks. Lithium-added chow (40 mmol Li/kg chow) was custom prepared (MP Biomedicals, Aurora, Ohio, USA). Clopidogrel bisulfate was administered orally by powdering and dissolving Plavix® tablets (Bristol-Myers Squibb, New York, N.Y., USA) in drinking water. The concentration of the drug in the drinking water was adjusted daily based on the water consumption of the animals the previous day. The clopidogrel dose used in Sprague-Dawley rats (20 mg/kg bw/day) was the same as used by other investigators (de La Crux et al, 2003; Graciano et al, 2008). In mice, clopidogrel was administered at a dose of 80 mg/kg bw/day. When compared with the human clinical dose of Plavix®, and adjusted to the K$_m$ factor (ratio of body surface area to body weight) of the species (man vs. rat or mouse) (Reagan-Shaw et al, 2007), the doses used in rats or mice were 2.5- and 5-fold higher, respectively. Toxicological evaluation of clopidogrel showed that doses as high as 165 mg/kg bw/day upto 4 weeks in rats were free from toxicity (Reist et al, 2000). A higher dose of clopidogrel (40 mg/kg bw/day) was used in Brattleboro rats to ensure an unequivocal outcome whether positive or negative. Twenty-four hour urine samples were collected by placing the animals in the appropriate metabolic cages designed for rats and mice. Blood and kidney tissues were collected at necropsy. Cortical, outer and inner medullary regions of the kidneys were dissected out and processed for laboratory assays.

Blood, urine and tissue analysis: Osmolalities of clear urine samples were measured by vapor pressure method (Wescor, Logan, Utah, USA). Microhematocrit was determined by centrifuging free-flowing blood collected in heparinized capillary tubes in a microhematocrit centrifuge (Clay Adams, Parsippany, N.J., USA). Urinary excretion of AVP was quantified by a commercial ELISA kit (Enzo Life Sciences, Farmingdale, N.Y., USA). Total nitrate/nitrite contents of urine samples were determined by a commercial kit (Cayman Chemical, Ann Arbor, Mich.).Na, Li and K levels in serum and/or urine were determined on EasyElectrolyte® (Medica Corp., Bedford, Mass., USA). Based on serum and urine analysis, electrolyte-free clearance [$C_{H2O}$(e)] was computed using the formula $C_{H2O}(e)=V((1-U_{Na}+U_K)/P_{Na})$, where V=urine volume, $U_{Na}$ and $U_K$ are urine Na and K, and $P_{Na}$ is plasma Na, respectively (Schrier 2006). Lithium levels in inner medullary tissue homogenates were assayed by Inductively Coupled Plasma-Mass Spectrometry (ICPMS) by Exova (Santa Fe Springs, Calif., USA), and were normalized to their respective protein contents. ICPMS has a detection limit of 0.06 ppm for Li, with recovery of 91% in spiked samples. Li was not detectable in the homogenization medium (0.5% SDS and 0.02% sodium azide in ultrapure water).

Real-Time RT-PCR Assay: This was performed essentially as described previously (Zhang et al, 2009, 2010, 2011, 2012). After extraction of total RNA and removal of traces of genomic DNA, cDNA was synthesized by SuperScript Reverse Transcriptase II (Invitrogen, Carlsbad, Calif., USA). Real-time PCR amplifications were carried out on cDNA samples in Applied Biosystems 7500 Real-time PCR System (Foster City, Calif., USA), with AmpliTaq Gold and SYBR Green for detection. The sequences of primer pairs used are:

```
P2Y12 receptor (NM_022800.1):
forward: (primer position: 494-517)
                                        (SEQ ID NO: 1)
TAACCATTGACCGATACCTGAAGA;

reverse: (primer position: 548-569)
                                        (SEQ ID NO: 2)
ATCTTCGCACCCAAAAGATTGC;

product size: 75 bp (modified from ref # Tozaki-
Saito et al, 2008)

β-actin: (NM_031144.2)
forward: (primer position: 18-37)
                                        (SEQ ID NO: 3)
CACCCGCGAGTACAACCTTC;

reverse: (primer position: 205-224)
                                        (SEQ ID NO: 4)
CCCATACCCACCATCACACC;

product size: 207 bp (from Zhang et al, 2010)
```

Specificity of the PCR amplifications was confirmed by sequencing the PCR product in the DNA Core Facility of the University of Utah, and then blasting in the National Center for Biotechnology Information (NCBI) database.

Immunoblotting: Processing of the kidney tissue samples and immunoblotting were done as described previously (Zhang et al, 2009, 2010, 2012). Differences in protein loading were corrected by normalizing the band densities of the target proteins to that of (3-actin (polyclonal antibody from Biolegend, San Diego, Calif., USA). Rabbit polyclonal antibody to $P2Y_{12}$ receptor and its blocking peptide were purchased from AnaSpec (Fremont, Calif., USA). Non-specific binding was prevented by incubation of the membranes with goat serum. Generation and characterization of AQP2 antibody (GN-762) was described previously (Kishore et al, 2000; Zhang et al, 2008).

Statistical Analysis: All quantitative data are expressed as mean±standard error (SE). Comparisons among the means of multiple groups were made by one-way analysis of variance (ANOVA), followed by the assessment of statistical significance by Tukey-Kramer Multiple Comparison Test or Student-Newman-Keuls Multiple Comparison Test. Differences between the means of two groups were determined by unpaired t test or where applicable, by Mann-Whitney nonparametric test. P values less than 0.05 were considered significant. GraphPad Instat® (GraphPad Software, Inc., La Jolla, Calif.) was used for statistical analysis.

Figure 10:
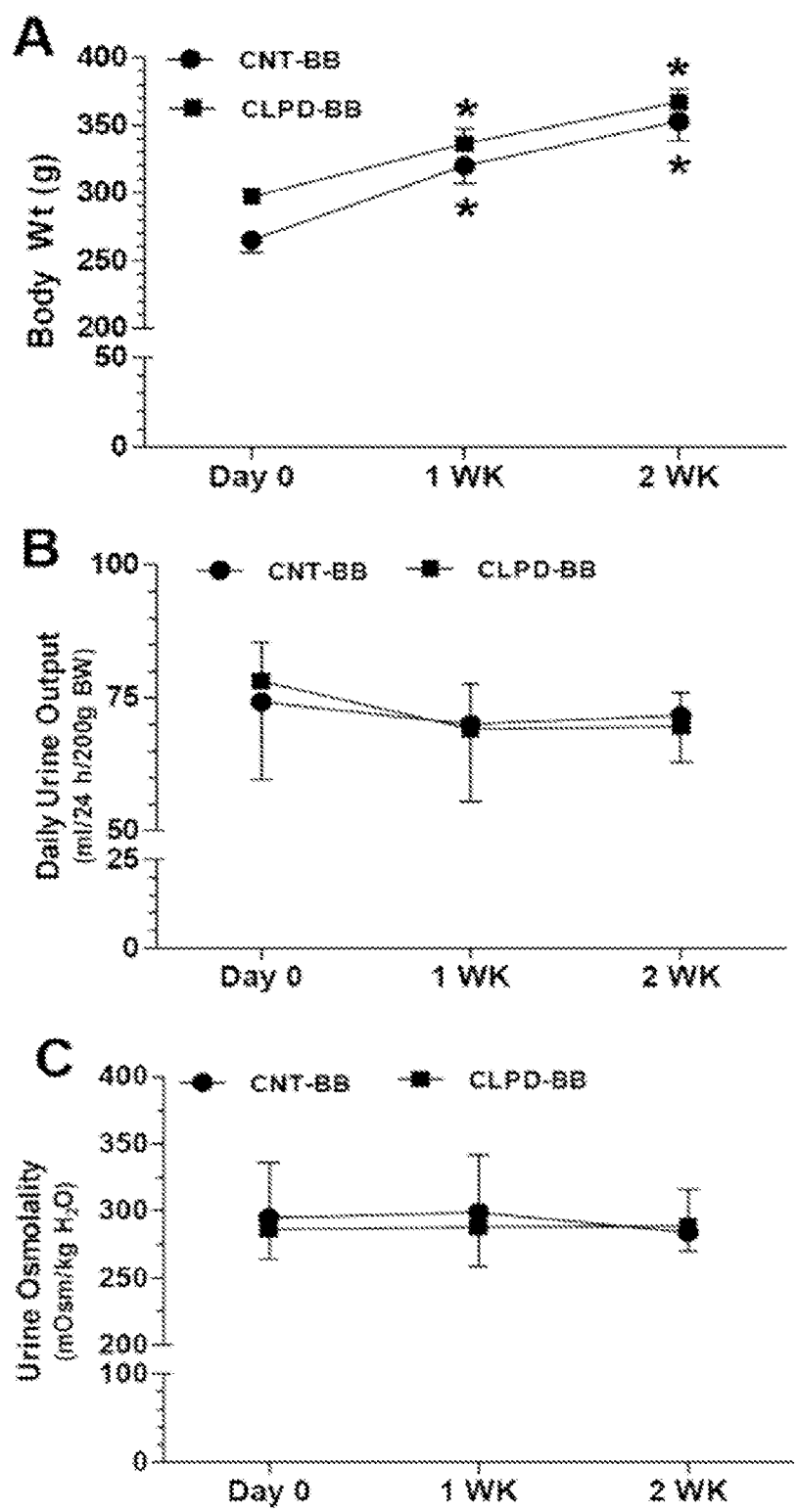
FIG. 10 shows the effect of clopidogrel (CLPD; 40 mg/kg bw/day) administration in drinking water for 2 weeks on body weight (A), urine output (B) and urine osmolality (C) in Brattleboro (CLPD-BB) rats as compared to control Brattleboro rats (CNT-BB). 1 WK is 1 week, & 2 WK is 2 weeks, N=4 per group. *significantly different from the corresponding day 0 values.

Since clopidogrel administration significantly increased urinary excretion of AVP, the role of AVP was further assessed in Brattlenoro mutant rats, which genetically lack AVP, and so cannot concentrate their urine. Clopidogrel (40 mg/kg bw/day) was administered for 2 weeks in drinking water to Brattleboro mutant rats that lack AVP. Clopidogrel did not increase the urinary concentrating ability in Brattleboro rats. Results can be seen in FIG. 10.

Figure 11:
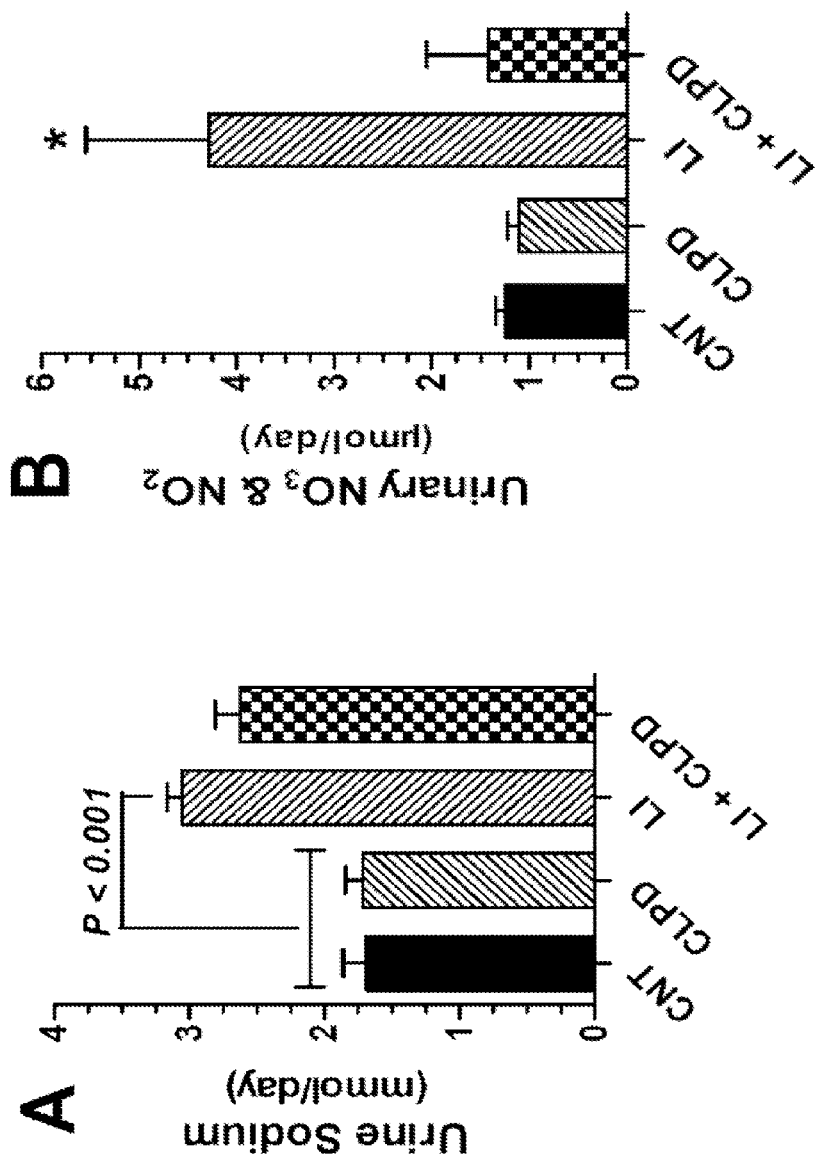
FIG. 11 shows data on the effect of clopidogrel (CLPD; 40 mg/kg bw/day) on lithium-induced alterations in rats. (Panel A) urinary sodium excretion, n=4-6/group. (Panel B) urinary total nitrates/nitrites excretion, *significantly different from all other groups, n=4-5/group. CNT is the control group; LI is the lithium-treated group; LI+CLPD is the clopidogrel and lithium-treated group.

Lithium-induced nephrogenic diabetes insipidus is associated with natriuresis (loss of sodium in the urine). Clopidogrel has a modest effect in ameliorating the lithium-induced natriuresis (FIG. 11, Panel A). Lithium-induced nephrogenic diabetes insipidus is associated with a significant increase in the urinary excretion of total nitrates (NO3) and nitrites (NO2), which is a reflection of the production of nitric oxide (NO) in by the kidney. Increased production of NO causes dysregulation of sodium transport by the kidney. Clopidogrel significantly ameliorated the lithium-induced increase in urinary NO3/NO2 (FIG. 12, Panel B).

Figure 12:
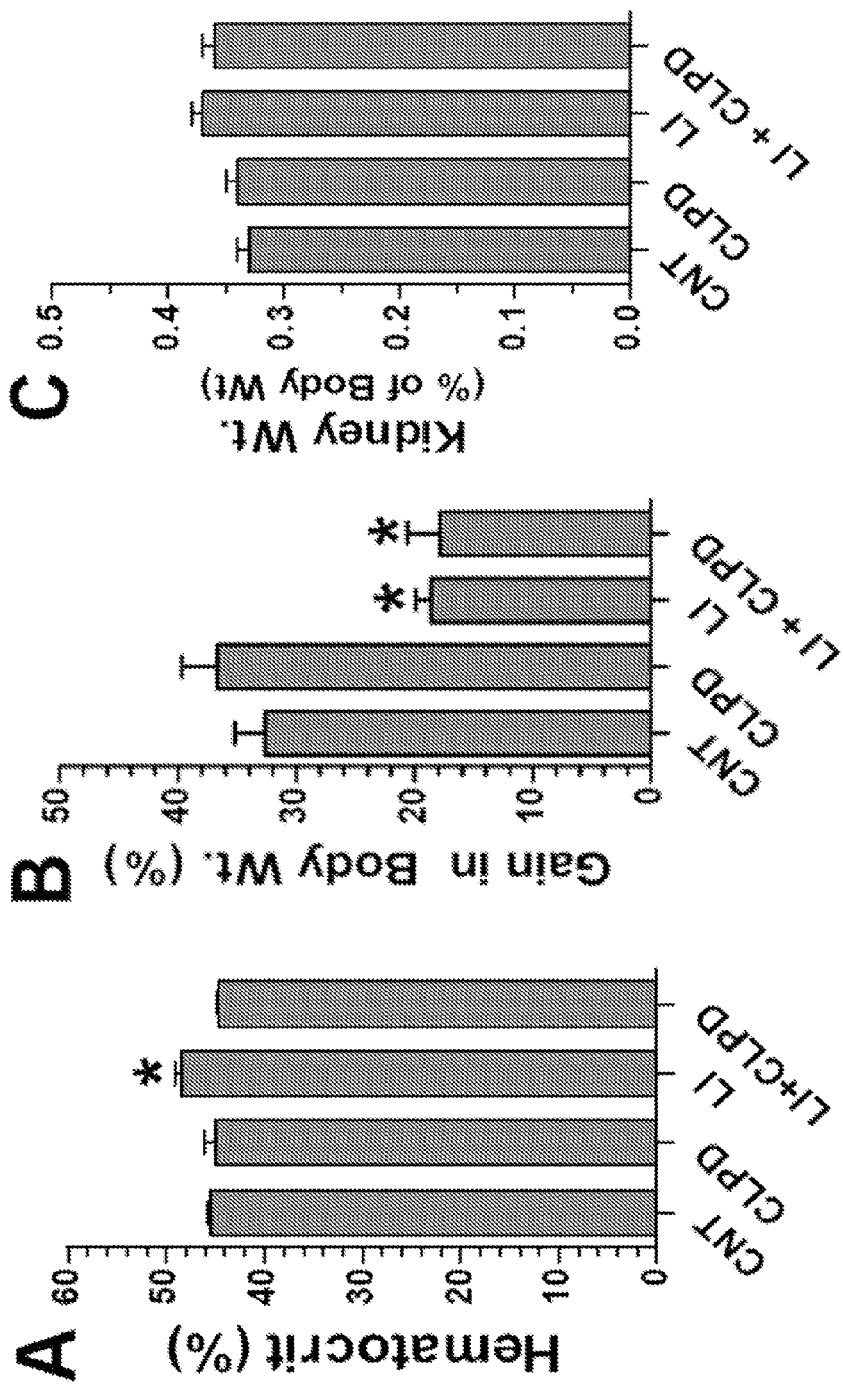
FIG. 12 shows data on the effect of clopidogrel (CLPD; 40 mg/kg bw/day) on LI (lithium)-induced alterations in rats. (Panel A) terminal hematocrit, *significantly different from all other groups, n=4-5/group. (Panel B) gain in body weight during the experimental period,*significantly different from control (CNT) and CLPD groups, n=4-6/group. (Panel C) kidney weight as percent of body weight, n=4-5/group.

Lithium treatment resulted in significant elevation of terminal hematocrit, which is a reflection of dehydration due to excessive loss of water in the urine (FIG. 12, Panel A). Clopidogrel treatment reversed the lithium-induced increase in hematocrit, suggesting that the animals are well hydrated (FIG. 12, Panel B) during the treatment period of 2 weeks, the rats gained body weight. This gain in body weight was significantly low in lithium-treated rats. Clopidogrel treatment did not ameliorate the low gain in the body weight due to lithium-treatment (FIG. 12, Panel C) despite the low gain in body weight in the lithium-treated rats (with or without added clopidogrel), the kidney weight as a percent of body weight did not change.

Administration of clopidogrel significantly prevented lithium-induced increase in urine output, decrease in urine osmolality and decrease in AQP2 protein abundance in the renal medulla in mice (FIG. 9). This indicates that there are no species differences in the observed effect of clopidogrel against lithium-induced nephrogenic diabetes insipidus.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for the treatment of nephrogenic diabetes insipidus in a mammal comprising the step of administering to the mammal an effective amount of a ADP-($P2Y_{12}$)-like receptor modulator, thereby treating nephrogenic diabetes insipidus in the mammal.

2. The method of claim 1, further comprising the step of administering a lithium salt.

3. The method of claim 1, wherein the mammal has been diagnosed with a need for treatment of a neurological disorder.

4. The method of claim 3, wherein the mammal is administered a lithium salt to treat the neurological disorder.

5. The method of claim 1, wherein the nephrogenic diabetes insipidus is acquired nephrogenic diabetes insipidus.

6. The method of claim 5, wherein the acquired nephrogenic diabetes insipidus is induced by administration of a therapeutic agent.

7. The method of claim 6, wherein the administration of the therapeutic agent precedes the administration of the ADP-($P2Y_{12}$)-like receptor modulator.

8. The method of claim 6, wherein the therapeutic agent is selected from acetohexamide, an aminoglycoside, amphotericin B, bumetanide, clozapine, colchicine, a corticosteroid, demeclocycline, ethacrynic acid, foscarnet, furosemide, gentamicin, glyburide, ifosfamide, a lithium salt, mannitol, methoxyflurane, propoxyphene, tolazamide, torsemide, and vinblastine.

9. The method of claim 8, wherein the therapeutic agent is selected from clozapine, foscarnet, and a lithium salt.

10. The method of claim 5, wherein the acquired nephrogenic diabetes insipidus is induced by a pathophysiological condition.

11. The method of claim 10, wherein the pathophysiological condition is selected from amyloidosis, analgesic nephropathy, chronic hypercalcemia, chronic kidney failure, hypokalemia, hypercalcemia, kidney disease, multiple myeloma, polycystic kidney disease, protein starvation, pyelonephritis, sarcoidosis, and sickle cell disease.

12. The method of claim 1, wherein the ADP-($P2Y_{12}$)-like receptor modulator is a modulator of a receptor selected from $P2Y_{12}$, $P2Y_{13}$, $P2Y_{14}$, GPR34, GPR34-like, GPR82, GPR87, and GPR171.

13. The method of claim 1, wherein the ADP-($P2Y_{12}$)-like receptor modulator is selected from clopidogrel, ticlopidine, prasugrel, ticagrelor, cangrelor, and elinogrel.

14. The method of claim 1, further comprising co-administration of a $P2Y_2$ modulator with the ADP-($P2Y_{12}$)-like receptor modulator.

15. The method of claim 14, wherein the ADP-($P2Y_{12}$)-like receptor modulator is a $P2Y_{12}$ modulator.

16. A method of co-treatment of nephrogenic diabetes insipidus and a neurological or psychiatric disorder comprising the step of co-administering to the mammal an effective amount of a ADP-($P2Y_{12}$)-like receptor modulator and an effective amount of a lithium salt, thereby treating, respectively, the nephrogenic diabetes insipidus and the neurological or psychiatric disorder.

17. The method of claim 16, wherein the nephrogenic diabetes insipidus is acquired nephrogenic diabetes insipidus.

18. The method of claim 16, wherein the ADP-($P2Y_{12}$)-like receptor modulator is a modulator of a receptor selected from $P2Y_{12}$, $P2Y_{13}$, $P2Y_{14}$, GPR34, GPR34-like, GPR82, GPR87, and GPR171.

19. The method of claim 18, wherein the $P2Y_{12}$ modulator is selected from clopidogrel, ticlopidine, prasugrel, ticagrelor, cangrelor, and elinogrel.

20. A method for treating age-related defects in urinary concentration in a mammal, comprising the step of administering to the mammal an effective amount of a ADP-(P2Y12)-like receptor modulator, thereby increasing urinary concentration in the mammal.

21. The method of claim 20, wherein the ADP (P2Y12)-like receptor modulator is clopidogrel.

* * * * *